(12) United States Patent
Parker et al.

(10) Patent No.: US 10,997,871 B2
(45) Date of Patent: May 4, 2021

(54) CONTRACTILE FUNCTION MEASURING DEVICES, SYSTEMS, AND METHODS OF USE THEREOF

(71) Applicant: President and Fellows of Harvard College, Cambridge, MA (US)

(72) Inventors: Kevin Kit Parker, Cambridge, MA (US); Sung-Jin Park, Lexington, MA (US); Patrick Healy Campbell, Marlborough, MA (US); Johan Ulrik Lind, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 377 days.

(21) Appl. No.: 15/514,011

(22) PCT Filed: Sep. 24, 2015

(86) PCT No.: PCT/US2015/051818
§ 371 (c)(1),
(2) Date: Mar. 24, 2017

(87) PCT Pub. No.: WO2016/069142
PCT Pub. Date: May 6, 2016

(65) Prior Publication Data
US 2018/0357927 A1 Dec. 13, 2018

Related U.S. Application Data

(60) Provisional application No. 62/054,627, filed on Sep. 24, 2014.

(51) Int. Cl.
| | | |
|---|---|---|
| *G09B 23/28* | (2006.01) | |
| *C12M 3/00* | (2006.01) | |
| *C12M 1/34* | (2006.01) | |
| *C12M 1/00* | (2006.01) | |
| *G01N 3/32* | (2006.01) | |
| *C12N 5/077* | (2010.01) | |
| *C12M 1/12* | (2006.01) | |
| *G01N 33/50* | (2006.01) | |

(52) U.S. Cl.
CPC ............ *G09B 23/28* (2013.01); *C12M 21/08* (2013.01); *C12M 25/02* (2013.01); *C12M 31/10* (2013.01); *C12M 41/46* (2013.01); *C12N 5/0657* (2013.01); *G01N 3/32* (2013.01); *G01N 33/5091* (2013.01); *G01N 2203/0089* (2013.01)

(58) Field of Classification Search
CPC ..... C12N 5/0657; C12M 21/08; C12M 41/46; C12M 31/10; C12M 25/02; G01N 3/32; G01N 33/5091; G01N 2203/0089; G09B 23/28
See application file for complete search history.

(56) References Cited

U.S. PATENT DOCUMENTS

| | | |
|---|---|---|
| 7,043,292 B2 | 5/2006 | Tarjan et al. |
| 8,492,150 B2 | 7/2013 | Parker et al. |
| 8,748,181 B2 | 6/2014 | Kuo et al. |
| 8,999,378 B2 | 4/2015 | Parker et al. |
| 9,012,172 B2 | 4/2015 | Parker et al. |
| 9,068,168 B2 | 6/2015 | Feinberg et al. |
| 9,383,350 B2 | 7/2016 | Parker et al. |
| 2003/0059103 A1 | 3/2003 | Shiomi et al. |
| 2004/0009566 A1 | 1/2004 | Okano et al. |
| 2004/0078090 A1 | 4/2004 | Binette et al. |
| 2004/0101819 A1 | 5/2004 | Montemagno et al. |
| 2005/0080402 A1 | 4/2005 | Santamore et al. |
| 2005/0085847 A1 | 4/2005 | Galdonik et al. |
| 2006/0003439 A1 | 1/2006 | Ismagiloy et al. |
| 2007/0060815 A1 | 3/2007 | Martin et al. |
| 2009/0054954 A1 | 2/2009 | Foley et al. |
| 2010/0041972 A1 | 2/2010 | Mason |
| 2010/0196432 A1 | 8/2010 | Feinberg et al. |
| 2010/0305460 A1 | 12/2010 | Pinter et al. |
| 2011/0189719 A1 | 8/2011 | Kuo et al. |
| 2011/0250585 A1 | 10/2011 | Ingber et al. |
| 2012/0134570 A1 | 5/2012 | Trumbull et al. |
| 2012/0135448 A1 | 5/2012 | Parker et al. |
| 2012/0142556 A1 | 6/2012 | Parker et al. |
| 2013/0046134 A1 | 2/2013 | Parker et al. |
| 2013/0289675 A1 | 10/2013 | Deisseroth et al. |
| 2013/0312638 A1 | 11/2013 | Parker et al. |
| 2013/0330378 A1 | 12/2013 | Parker et al. |
| 2014/0235826 A1 | 8/2014 | Deisseroth et al. |
| 2014/0236267 A1 | 8/2014 | Parker |

(Continued)

FOREIGN PATENT DOCUMENTS

| | | |
|---|---|---|
| WO | WO-2012/131360 A2 | 10/2012 |
| WO | WO-2013/086512 A2 | 6/2013 |

(Continued)

OTHER PUBLICATIONS

Denyer et al. "Preliminary study on the suitability of a pharmacological bio-assay based on cardiac myocytes cultured over microfabricated microelectrode arrays" (1998), Cellular Engineering, vol. 36: 638-644. (Year: 1998).*
International Search Report for Application No. PCT/US2015/051818, dated Jun. 2, 2016. 4 pages.
International Preliminary Report on Patentability for Application No. PCT/US2015/051818, dated Apr. 6, 2017. 8 pages.
Alford et al., "Biohybrid thin films for measuring contractility in engineered cardiovascular muscle" Biomaterials 31, May 2010, 3613-3621.
Badrossamay, M.R. et al. "Nanofiber assembly by rotary jet-spinning." Nano Letters, May 2010;10(6):2257-2261.

(Continued)

*Primary Examiner* — Teresa E Knight
(74) *Attorney, Agent, or Firm* — McCarter & English, LLP; Maria Laccotripe Zacharakis; Deborah L. Nagle

(57) ABSTRACT

Exemplary embodiments provide systems, devices and methods for simultaneously measuring mechanical and electrophysiological tissue responses (e.g., contractile function, or the like).

10 Claims, 47 Drawing Sheets

(56) References Cited

U.S. PATENT DOCUMENTS

| | | |
|---|---|---|
| 2014/0322515 A1 | 10/2014 | Parker et al. |
| 2015/0182679 A1 | 7/2015 | Parker et al. |
| 2015/0253307 A1 | 9/2015 | Parker et al. |
| 2015/0354094 A1 | 12/2015 | Parker et al. |
| 2016/0003806 A1 | 1/2016 | Parker et al. |
| 2017/0016875 A1 | 1/2017 | Parker et al. |
| 2018/0372725 A1 | 12/2018 | Parker et al. |

FOREIGN PATENT DOCUMENTS

| | | |
|---|---|---|
| WO | WO-2013/115896 A2 | 8/2013 |
| WO | WO-2016/007879 A1 | 1/2016 |
| WO | WO-2016/069142 A2 | 5/2016 |
| WO | WO-2016/191179 A1 | 12/2016 |
| WO | WO-2017/027390 A1 | 2/2017 |
| WO | WO-2017/087759 A1 | 5/2017 |
| WO | WO-2018/027105 A1 | 2/2018 |

OTHER PUBLICATIONS

Bray et al., "Sarcomere Alignment is Regulated by Myocyte Shape" Cell Motility and the Cytoskeleton, Aug. 2008, 65(8), pp. 641-651.
Bursac et al., "Cardiomyocyte cultures with controlled macroscopic anisotropy." Circulation Rearch, Dec. 2002, vol. 91, pp. e45-e54.
Grosberg et al., "Ensembles of engineered cardiac tissues for physiological and pharmacological study: Heart on a chip." Lab Chip, Nov. 2011, vol. 11, p. 4165.
Lehnert et al., "Cell behavior on micropatterned substrata: limits of extracellular matrix geometry for spreading and adhesion."Journal of Cell Science, Jan. 2004, vol. 117 (1), pp. 41-52.
Mao et al., "Capillary isoelectric focusing with whole column imaging detection for analysis of proteins and peptides," J. Biochem. Biophys. Methods, Feb. 1999, 39:93-110.
Park et al., "Real-Time Measurement of the Contractile Forces of Self-Organized Cardiomyocytes on Hybrid Biopolymer Microcantilevers," Anal. Chem. Oct. 2005, 77:6571-6580.
Parker et al., "Extracellular matrix, mechanotransduction and structural hierarchies in heart tissue engineering." Phil Trans R. Soc B, Epub, Jun. 22, 2007, vol. 362, pp. 1267-1279.
Spring, Kenneth R. "Electronic Imaging in Neuroscience," Curr. Protoc. Neurosci. May 2002, 2.4.1-2.4.9.
Xi et al., "Development of a Self-Assembled Muscle-Powered Piezoelectric Microgenerator", NSTI-Nanotech, 2004, vol. 1, pp. 3-6. (The month of publication is not available; however, the year of publication is sufficiently earlier than the effective U.S. filing date and any foreign priority date so that the particular month of publication is not in issue.).
Yang et al., "Fabrication of well-defined PLGA scaffolds using novel microembossing and carbon dioxide bonding," Biomaterials, Sep. 2005, vol. 26, pp. 2585-2594.
International Search Report and Written Opinion from PCT/US2015/016395, dated Jan. 6, 2016.
International Search Report and Written Opinion from PCT/US2015/051818 dated Jun. 2, 2016.
U.S. Appl. No. 12/443,890, filed Apr. 8, 2010, US 20100196432, Abandoned.
U.S. Appl. No. 12/223,560 U.S. Pat. No. 8,492,150, filed Feb. 25, 2009, US 20090317852, Granted.
U.S. Appl. No. 13/922,432 U.S. Pat. No. 9,383,350, filed Jun. 20, 2013, US 20140004553, Granted.
U.S. Appl. No. 12/680,277 U.S. Pat. No. 9,068,168, filed Sep. 1, 2010, US 20100330644, Granted.
U.S. Appl. No. 12/994,187 U.S. Pat. No. 8,748,181, filed Mar. 17, 2011, US 20110189719, Granted.
U.S. Appl. No. 13/120,003 U.S. Pat. No. 8,999,378, filed Jun. 2, 2011, US 20120029416, Granted.
U.S. Appl. No. 13/878,383, filed Aug. 16, 2013, US 20130330378, Abandoned.
U.S. Appl. No. 13/318,227 U.S. Pat. No. 9,012,172, filed Feb. 21, 2012, US 20120142556, Granted.
U.S. Appl. No. 14/642,906, filed Mar. 10, 2015, US 20160003806, Published.
U.S. Appl. No. 13/320,031, filed Jan. 30, 2012, US 20120135448, Granted.
U.S. Appl. No. 15/203,924, filed Jul. 7, 2016, Abandoned.
U.S. Appl. No. 13/580,191, filed Oct. 31, 2012, US 20130046134, Abandoned.
U.S. Appl. No. 13/808,411, filed Jan. 4, 2013, Abandoned.
U.S. Appl. No. 14/261,693, filed Apr. 25, 2014, US 20140236267, Published.
U.S. Appl. No. 13/988,088, filed Aug. 5, 2013, US 20130312638, Abandoned.
U.S. Appl. No. 14/362,287, filed Jun. 2, 2014, US 20140342394, Published.
U.S. Appl. No. 14/359,005, filed May 16, 2014, US 20140322515, Published.
U.S. Appl. No. 14/415,945, filed Jan. 20, 2015, US 20150182679, Allowed.
U.S. Appl. No. 14/429,826, filed Mar. 20, 2015, US 20150253307, Abandoned.
U.S. Appl. No. 15/869,228, filed Jan. 12, 2018, US 20180372725, Published.
U.S. Appl. No. 14/763,620, filed Jul. 27, 2015, US 20150354094, Published.
U.S. Appl. No. 15/116,258, filed Aug. 3, 2016, US 20170016875, Published.
PCT/US2015/039983, Jul. 10, 2015, WO 2016007879, Published.
PCT/US2016/033168, May 19, 2016, WO 2016191179, Published.
PCT/US2016/045813, Aug. 5, 2016, WO 2017027390, Published.
PCT/US2016/062693, Nov. 18, 2016, WO 2017087759, Published.
PCT/US2017/045442, Aug. 4, 2017, WO 2018027105, Published.
PCT/US2019/016572, Feb. 5, 2019, Pending.

* cited by examiner

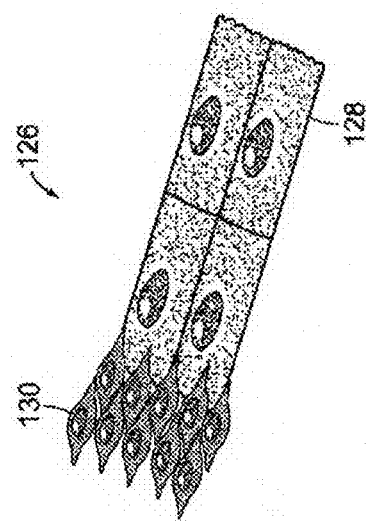
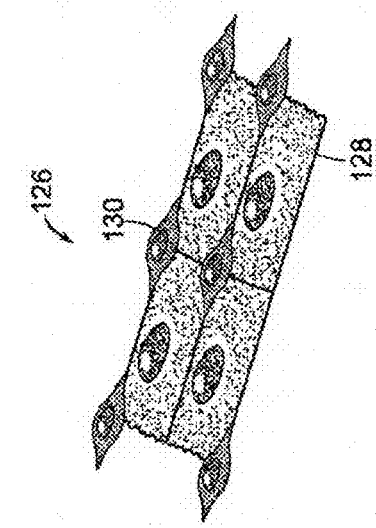
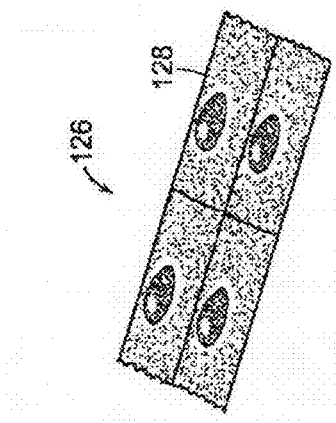
FIG. 3C
FIG. 3B
FIG. 3A

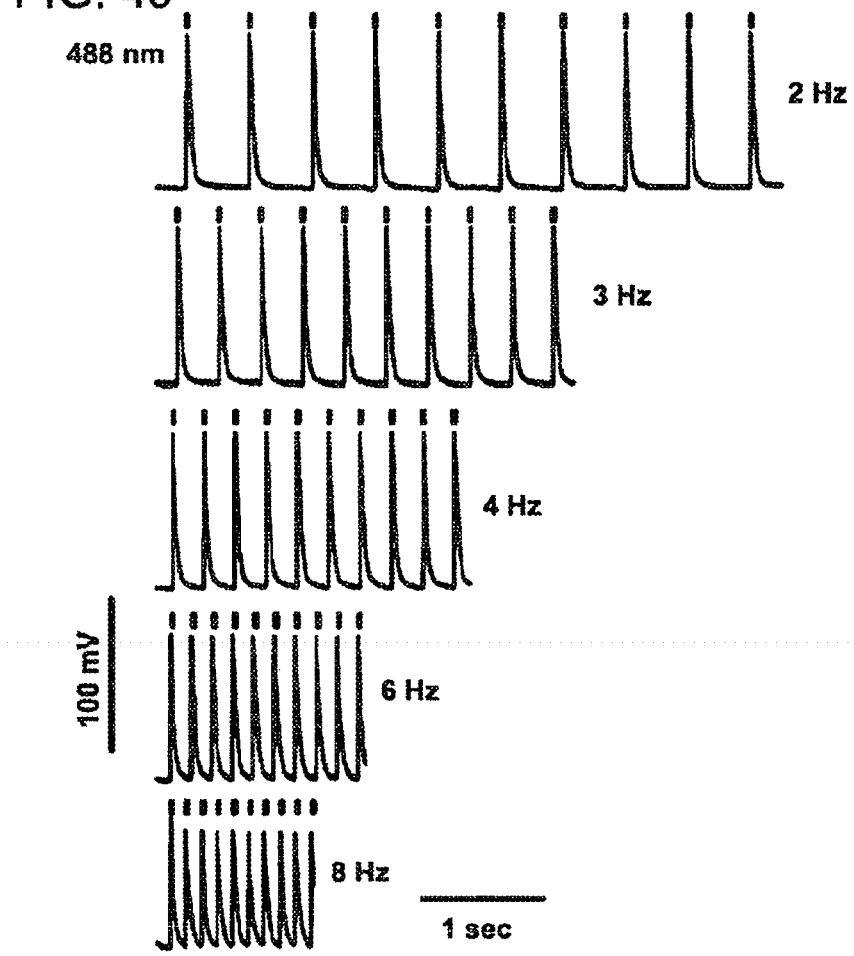
FIG. 49
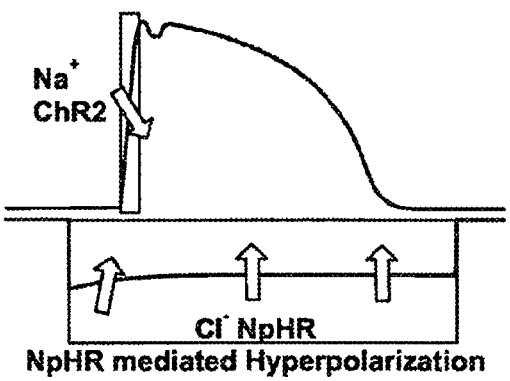
FIG. 50 ChR2 mediated Action Potential

 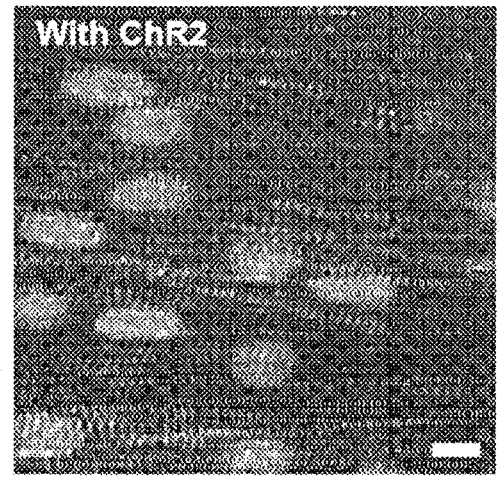
FIG. 57  FIG. 58
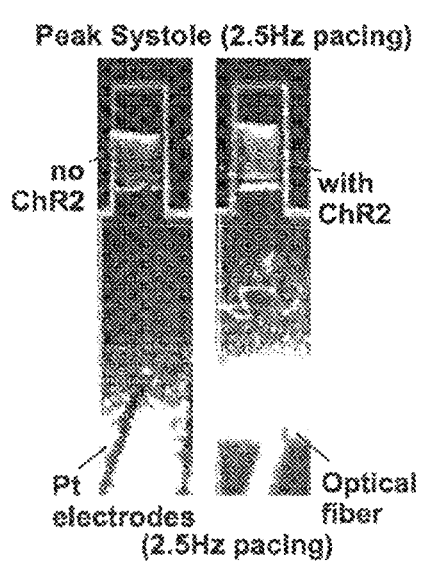 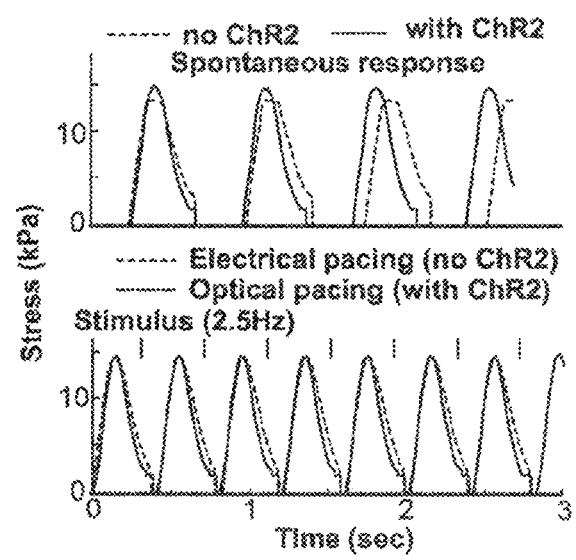
FIG. 59  FIG. 60

CONTRACTILE FUNCTION MEASURING DEVICES, SYSTEMS, AND METHODS OF USE THEREOF

RELATED APPLICATIONS

This application is a 35 U.S.C. § 371 national stage filing of International Application No. PCT/US2015/051818, filed on Sep. 24, 2015, which in turn claims the benefit of commonly assigned U.S. Provisional Patent Application No. 62/054,627, entitled "Optogenetic Cardiac Rhythm Modulation Tissue Structures, Systems, and Methods of Use Thereof", filed on Sep. 24, 2014. The entire contents of each of the foregoing applications are incorporated herein by reference.

GOVERNMENT SUPPORT

This invention was made with government support under grant numbers U01HL100408 and UH3TR000522, awarded by the National Institutes of Health (NIH), and under grant number W911NF-12-2-0036, awarded by the Defense Advanced Research Projects Agency (DARPA). Accordingly, the government has certain rights in the invention.

BACKGROUND

Identification and evaluation of new therapeutic agents or identification of suspect disease associated targets typically employ animal models which are expensive, time consuming, require skilled animal-trained staff and utilize large numbers of animals. Because many therapeutic agents are frequency-dependent, in vitro cardiotoxicity alternatives need to measure frequency-dependent mechanical and electrophysiological therapeutic agent responses of tissue, e.g., cardiac tissue, or the like. As an example, many anti-arrhythmia drugs are known to be use-dependent (e.g., frequency-dependent). As a further example, calcium handling activities (e.g., SERCA2 calcium pump activity) are frequency-dependent.

Conventional in vitro assays generally utilize electrical stimulation for testing responses of tissue. For example, frequency-dependent drug response has been measured by sweeping frequencies with a single electrical stimulator in cardiac tissue. However, high-pacing frequency can generate arrhythmia, resulting in damage to the tissue. Thus, alternative in vitro assays utilize multiple electrical stimulators with multiple frequencies (See, e.g., Huang, C. et al., "Characterization of voltage-gated sodium-channel blockers by electrical stimulation and fluorescence detection of member potential", *Nature Biotechnology*, Vol. 24, pp. 439-446 (2006)). However, each electrical stimulator necessitates an isolated chamber due to interference produced between electrical fields generated with multiple electrodes in a single chamber.

Accordingly, there is a need in the art for improved systems, devices and methods for simultaneously measuring mechanical and electrophysiological tissue responses with reduced negative effects on the tissue.

SUMMARY

The present invention provides systems, devices and methods for simultaneously measuring mechanical and electrophysiological tissue responses (e.g., contractile function, or the like).

The present invention is based, at least in part, on the discovery of in vitro systems and methods of use of such systems for the identification of compounds that modulate cardiac arrhythmia and defibrillation. Specifically, the exemplary system includes an anisotropic photosensitive cardiac rhythm modulation tissue structure, a computer-controlled light source adapted to provide photostimulation to at least a first portion and a second portion of the photosensitive cardiac rhythm modulation tissue structure, and a sensor array. The system also includes a computing device including computer-executable instructions for illuminating the first portion and the second portion of the tissue structure in a predetermined spatiotemporal pattern that employs cross-stimulation using the computer-controlled light source.

Photosensitive cardiac rhythm modulation tissue structures include cardiomyocytes transfected with a gene encoding a light-sensitive ion channel the protein product of which is functionally integrated in the cell membrane of a cardiac tissue structure. By stimulating the tissue structure with specific wavelengths of light and/or specific wavelengths of light and specific optical pacing frequencies, the mechanical contraction of the tissue can be controlled to mimic normal tissue or diseased tissue, e.g., arrhythmic tissue. Combining the photosensitive cardiac rhythm modulation tissue structures with calcium and/or voltage sensitive dyes, permits the simultaneous measurement of mechanical activities and electrophysiological activities.

Methods to prepare suitable photosensitive cardiac rhythm modulation tissues and structures for use in the claimed systems and methods, as well as methods to evaluate the activity of photosensitive cardiac rhythm modulation tissues and structures are described in, for example, U.S. Pat. No. 8,492,150, and U.S. Patent Publication Nos. 2012/0142556 and 2014/0236267, and PCT Publication Nos. WO 2010/127280 and WO 2013/086512, the entire contents of each of which are incorporated herein by reference.

In accordance with one exemplary embodiment, a method to generate an in vitro model of cardiac arrhythmia and defibrillation is provided. The method includes providing a tissue structure (e.g., an anisotropic photosensitive cardiac rhythm modulation tissue structure, or the like) and a light source adapted to provide photostimulation to the tissue structure. The method includes illuminating the tissue structure with a suitable wavelength of light in a predetermined spatiotemporal pattern of light. In some embodiments, the wavelength can be, e.g., between approximately 400 nm and approximately 600 nm, between approximately 425 nm and approximately 575 nm, between approximately 450 nm and approximately 550 nm, between approximately 475 nm and approximately 525 nm, between approximately 400 nm and approximately 550 nm, between approximately 400 nm and approximately 500 nm, between approximately 400 nm and approximately 450 nm, between approximately 450 nm and approximately 600 nm, between approximately 500 nm and approximately 600 nm, between approximately 550 nm and approximately 600 nm, between approximately 400 nm and approximately 590 nm, between approximately 400 nm and approximately 470 nm, between approximately 460 nm and approximately 650 nm, approximately 400 nm, approximately 450 nm, approximately 500 nm, approximately 550 nm, approximately 600 nm, or the like. In some embodiments, the spatiotemporal pattern of light can be a cross field stimulation including a combination of stimulation pulses from 470 nm blue light and from 590 nm yellow light with a time interval. For example, 470 nm blue light patterns can stimulate channelrhodopsin (ChR2) to induce activation of tissue, while 590 nm yellow light can stimulate halorhodposin (NpHR) to induce hyperpolarization of tissue.

The tissue structure can include a flexible polymer layer and/or a hydrogel layer, and a population of isolated pacing cells expressing a photosensitive membrane transport mechanism seeded on the flexible polymer layer and/or the hydrogel layer in a predetermined pattern. The cells can form a tissue structure which can perform a contractile function. An in vitro model of cardiac arrhythmia and defibrillation can thereby be generated.

In accordance with another exemplary embodiment, a method for identifying a compound that modulates cardiac arrhythmia and defibrillation is provided. The method includes providing a tissue structure (e.g., an anisotropic photosensitive cardiac rhythm modulation tissue structure, or the like), and a light source adapted to provide photostimulation to the tissue structure. The method includes illuminating the tissue structure with a suitable wavelength of light in a predetermined spatiotemporal pattern of light. The tissue structure can include a flexible polymer layer and/or a hydrogel layer, and a population of isolated pacing cells expressing a photosensitive membrane transport mechanism seeded on the flexible polymer layer and/or the hydrogel layer in a predetermined pattern. The cells can form a tissue structure which can perform a contractile function. The method includes contacting the model with a test compound. The method includes evaluating the activity of the tissue structure in response to the test compound, thereby identifying a compound that modulates cardiac arrhythmia and defibrillation.

In one embodiment, illuminating the tissue structure with a suitable wavelength of light in a predetermined spatiotemporal pattern can include illuminating the tissue structure in accordance with a cross-field stimulation protocol inducing a spiral wave pattern of contraction.

In one embodiment, illuminating the tissue structure with a suitable wavelength of light in a predetermined spatiotemporal pattern can include illuminating a first portion of the tissue structure with a first set of optical pulses at a substantially constant frequency. In some embodiments, the frequency can be, e.g., between approximately 0.5 Hz and approximately 4 Hz, between approximately 1 Hz and approximately 3.5 Hz, between approximately 1.5 Hz and approximately 3 Hz, between approximately 2 Hz and approximately 2.5 Hz, between approximately 1 Hz and approximately 4 Hz, between approximately 1.5 Hz and approximately 4 Hz, between approximately 2 Hz and approximately 4 Hz, between approximately 2.5 Hz and approximately 4 Hz, between approximately 3 Hz and approximately 4 Hz, between approximately 3.5 Hz and approximately 4 Hz, between approximately 0.5 Hz and approximately 3 Hz, approximately 0.5 Hz, approximately 1 Hz, approximately 1.5 Hz, approximately 2 Hz, approximately 2.5 Hz, approximately 3 Hz, approximately 3.5 Hz, approximately 4 Hz, or the like. In some embodiments, the physiological relevant frequency can be approximately 1.5 Hz. In some embodiments, the frequency can be between approximately 1 Hz and approximately 4 Hz for non-human (e.g., rat) cardiac tissue. In some embodiments, the frequency can be between approximately 0.5 Hz and approximately 3 Hz for human cardiac tissue.

The method can include illuminating a second portion of the tissue structure with an additional optical pulse for cross-field stimulation. A temporal interval between a pulse in the first set of optical pulses and the additional optical pulse can result in a spiral wave pattern of contraction. The temporal interval can be a function of a first stimulation pacing frequency and/or the tissue type (e.g., rat or human). In some embodiments, the temporal interval can be, e.g., between approximately 100 msec and approximately 500 msec, between approximately 150 msec and approximately 450 msec, between approximately 200 msec and approximately 400 msec, between approximately 250 msec and approximately 350 msec, approximately 300 msec, or the like, for a first stimulation pacing frequency of approximately 1.5 Hz with neonatal rat ventricular myocytes (NRVM).

In some embodiments, the temporal interval can be greater for human cardiac tissue than for rat cardiac tissue at the substantially same pacing frequencies. In some embodiments, the temporal interval can be, e.g., between approximately 200 msec and approximately 667 msec, between approximately 250 msec and approximately 650 msec, between approximately 300 msec and approximately 600 msec, between approximately 350 msec and approximately 550 msec, between approximately 400 msec and approximately 500 msec, approximately 450 msec, or the like, for a first stimulation pacing frequency of approximately 1.5 Hz with human cardiac tissue.

In some embodiments, the temporal interval can be shorter for increased stimulation pacing frequencies. In some embodiments, the temporal interval can be, e.g., between approximately 50 msec and approximately 400 msec, between approximately 100 msec and approximately 350 msec, between approximately 150 msec and approximately 300 msec, between approximately 200 msec and approximately 250 msec, or the like, for a first stimulation pacing frequency of approximately 2 Hz with human cardiac tissue.

In some embodiments, the temporal interval can be, e.g., between approximately 0 msec and approximately 1,000 msec, between approximately 50 msec and approximately 950 msec, between approximately 100 msec and approximately 900 msec, between approximately 150 msec and approximately 850 msec, between approximately 200 msec and approximately 800 msec, between approximately 250 msec and approximately 750 msec, between approximately 300 msec and approximately 700 msec, between approximately 350 msec and approximately 650 msec, between approximately 400 msec and approximately 600 msec, between approximately 450 msec and approximately 550 msec, approximately 500 msec, or the like, for a variety of stimulation pacing frequencies for different tissues.

In one embodiment, illuminating the tissue structure with a suitable wavelength of light in a predetermined spatiotemporal pattern can include illuminating the tissue structure with one or more optical pulses that results in degradation of the spiral wave pattern of contraction and reestablishment of a single wave front of contraction.

In one embodiment, illuminating a first portion of the tissue structure with a first set of optical pulses at a substantially constant frequency can include illuminating a first portion of the tissue structure along a line at or near an edge of the tissue structure.

In one embodiment, illuminating the tissue structure with a suitable wavelength of light in a predetermined spatiotemporal pattern can include illuminating a first portion of the tissue structure along a line with a first set of optical pulses at a substantially constant frequency. The method can include illuminating a second portion of the tissue structure with a first additional optical pulse for cross-field stimulation with a first temporal interval between a pulse in the first set of optical pulses and the first additional optical pulse. In some embodiments, an optical pulse temporal width of a first stimulation and a second stimulation pulse (S1 and S2, respectively) can be approximately 10 msec. In some embodiments, the pulse width can be, e.g., between approximately 1 femtosec and approximately 1,000 msec, between approximately 1 femtosec and approximately 900 msec, between approximately 1 femtosec and approximately 800 msec, between approximately 1 femtosec and approximately 700 msec, between approximately 1 femtosec and approximately 600 msec, between approximately 1 femtosec and approximately 500 msec, between approximately 1 femtosec and approximately 400 msec, between approximately 1 femtosec and approximately 300 msec, between approximately 1 femtosec and approximately 200 msec, between approximately 1 femtosec and approximately 100 msec, between approximately 1 femtosec and approximately 50 msec, between approximately 1 femtosec and approximately 1 msec, or the like. As noted above, in some embodiments, the first temporal interval can be between approximately 0 msec and approximately 1,000 msec. The method can include illuminating the second portion of the tissue structure with a second additional optical pulse for cross-field stimulation with a second temporal interval between a pulse in the first set of optical pulses and the first additional optical pulse. As noted above, in some embodiments, the second temporal interval can be between approximately 0 msec and approximately 1,000 msec.

In one embodiment, illuminating the tissue structure with a suitable wavelength of light can include illuminating a first portion of the tissue structure along a line with sets of optical pulses at a substantially constant frequency. The method can include illuminating a second portion of the tissue structure with additional optical pulses for cross-field stimulation. A temporal interval between a pulse in the sets of optical pulses and a subsequent additional optical pulse can vary for each additional subsequent additional optical pulse.

In one embodiment, the methods can include determining a temporal interval vulnerability window based on whether each additional optical pulse resulted in a spiral wave pattern of contraction.

In one embodiment, the anisotropic photosensitive cardiac rhythm modulation tissue structure can include one or both of a calcium-sensitive dye and a voltage-sensitive dye.

In one embodiment, the methods can include adding one or both of a calcium-sensitive dye and a voltage-sensitive dye to the provided anisotropic photosensitive cardiac rhythm modulation tissue structure.

In accordance with another exemplary embodiment, a system for in vitro modeling of cardiac arrhythmia and defibrillation is provided. The system can include a tissue structure (e.g., an anisotropic photosensitive cardiac rhythm modulation tissue structure, or the like). The system can include a computer-controlled light source adapted to provide photostimulation to at least a first portion and a second portion of the tissue structure. The system can include a sensor array. The system can include a computing device including computer-executable instructions for illuminating the first portion and the second portion of the tissue structure in a predetermined spatiotemporal pattern that employs cross-stimulation using the computer-controlled light source.

In one embodiment, the computer-executable instructions can include instructions for illuminating the tissue structure in accordance with a cross-field stimulation protocol inducing a spiral wave pattern of contraction.

In one embodiment, the computer-executable instructions can include instructions for illuminating the first portion of the tissue structure with a first set of optical pulses at a substantially constant frequency. The computer-executable instructions can further include instructions for illuminating the second portion of the tissue structure with an additional optical pulse for cross-field stimulation. A temporal interval between a pulse in the first set of optical pulses and the additional optical pulse can result in a spiral wave pattern of contraction.

In one embodiment, the first portion of the tissue structure can be along a line at or near an edge of the tissue structure.

In one embodiment, the computer-executable instructions can include instructions for illuminating the first portion of the tissue structure along a line with a first set of optical pulses at a substantially constant frequency. The computer-executable instructions can include instructions for illuminating the second portion of the tissue structure with a first additional optical pulse for cross-field stimulation with a first temporal interval between a pulse in the first set of optical pulses and the first additional optical pulse. The computer-executable instructions can include instructions for illuminating the second portion of the tissue structure with a second additional optical pulse for cross-field stimulation with a second temporal interval between a pulse in the first set of optical pulses and the first additional optical pulse.

In one embodiment, the computer-executable instructions can include instructions for illuminating the first portion of the tissue structure along a line with sets of optical pulses at a substantially constant frequency. The computer-executable instructions can include instructions for illuminating the second portion of the tissue structure with additional optical pulses for cross-field stimulation. A temporal interval between a pulse in the sets of optical pulses and a subsequent additional optical pulse can vary for each subsequent additional optical pulse.

In accordance with another exemplary embodiment, a device for measuring a contractile function is provided. The device can include a support structure configured to support a tissue structure thereon. The device can include a mechanical sensor system configured to measure a mechanical activity associated with contraction of the tissue structure. The device can include an electrophysiological sensor system configured to measure an electrophysiological activity associated with contraction of the tissue structure simultaneously to measurement of the mechanical activity by the mechanical sensor system.

In one embodiment, the tissue structure can include at least one of a flexible polymer layer or a hydrogel layer, and a population of isolated muscle cells (e.g., pacing cells, or the like) expressing a photosensitive membrane transport mechanism seeded on at least one of the flexible polymer layer or the hydrogel layer in a predetermined pattern.

In one embodiment, the tissue structure can be an anisotropic muscle tissue structure. In one embodiment, the tissue structure can be a muscle thin film structure as described in, for example, U.S. Pat. No. 8,492,150, and U.S. Patent Publication Nos. 2012/0142556 and 2014/0236267, and PCT Publication Nos. WO 2010/127280 and WO 2013/086512, the entire contents of each of which are incorporated herein by reference. In one embodiment, the tissue structure can be an anisotropic photosensitive cardiac rhythm modulation tissue structure.

In one embodiment, the anisotropic muscle tissue structure can include cardiomyocytes. In one embodiment, the tissue structure can include an expression construct expressing an optogenetic gene.

In one embodiment, the device can include a light source adapted to provide photostimulation to the tissue structure. The photostimulation can result in contractile function of the tissue structure.

In one embodiment, the light source can provide photostimulation to the tissue structure at specific wavelengths of light and specific optical pacing frequencies to control contraction of the tissue structure to mimic normal tissue or diseased tissue. In some embodiments, healthy tissue (e.g., rat cardiac tissue) can respond to optical pacing frequencies of, e.g., between approximately 1 Hz and approximately 4 Hz, between approximately 1.5 Hz and approximately 3.5 Hz, between approximately 2 Hz and approximately 3 Hz, approximately 2.5 Hz, or the like. In some embodiments, diseased tissue (e.g., tissue having arrhythmia) cannot respond to low pacing frequencies between approximately 1 Hz and approximately 2 Hz and, therefore, pacing frequencies, e.g., between approximately 2 Hz and approximately 4 Hz, between approximately 2.5 Hz and approximately 3.5 Hz, approximately 3 Hz, or the like, can be used. In some embodiments, the light wavelengths can be approximately 470 nm for ChR2 stimulation and approximately 590 nm for chimeric channelrhodopsin (C1V1) or NpHR.

In one embodiment, the light source can provide photostimulation to the tissue structure in a predetermined spatiotemporal pattern of light.

In one embodiment, the mechanical sensor system can be at least one of a bright field microscopy system or a dark field microscopy system. In one embodiment, the mechanical sensor system can optically measure movement during contraction of the tissue structure and determines stress of the tissue structure during contraction. In one embodiment, the mechanical sensor system can include an electrical sensor. The electrical sensor can measure a stress of the tissue structure during contraction. In one embodiment, the electrical sensor can measure at least one of a change in electrical resistance, a change in electrical current, a change in inductance, combinations thereof, or the like, due to the stress of the tissue structure during contraction.

In one embodiment, the electrical sensor can include at least one of a strain gage, a piezoresistive sensor, a piezoelectrical sensor, a magnetic sensor, combinations thereof, or the like. In one embodiment, the electrophysiological sensor system can optically measure an intensity or spectrum of a synthetic indicator or a genetically encoded fluorescent protein indicator due to change in membrane voltage and in ion concentration of tissue in the tissue structure. In one embodiment, the synthetic indicator and the genetically encoded fluorescent protein indicator can be a voltage indicator, a calcium indicator, an ion indicator, combinations thereof, or the like.

In one embodiment, the mechanical sensor system and the electrophysiological sensor system can define an optical mapping system including dark field microscopy for simultaneous contractility and calcium transient measurement. The system can include a long wavelength intracellular calcium indicator for calcium transient imaging and an infrared light-emitting diode light source for dark field illumination. The long wavelength intracellular calcium indicator and the infrared light-emitting diode light source can prevent overlap of excitation light wavelengths of calcium transients and contractility measurements with excitation of light sensitive ion channels.

In one embodiment, the mechanical sensor system and the electrophysiological sensor system can include optical measurement systems.

In one embodiment, the mechanical sensor system and the electrophysiological sensor system can include electrical measurement systems.

In one embodiment, the mechanical sensor system can include an optical measurement system and the electrophysiological sensor system can include an electrical measurement system.

In one embodiment, the mechanical sensor system can include an electrical measurement system and the electrophysiological sensor system can include an optical measurement system.

In accordance with another exemplary embodiment, a method of measuring a contractile function is provided. The method includes providing a device for measuring a contractile function. The device can include a support structure, a mechanical sensor system, and an electrophysiological sensor system. The method includes positioning a tissue structure on the support structure. The method includes stimulating the tissue structure to cause contractile function of the tissue structure. The method includes simultaneously measuring a mechanical activity associated with contraction of the tissue structure with the mechanical sensor system and an electrophysiological activity associated with contraction of the tissue structure with the electrophysiological sensor system.

In one embodiment, the tissue structure can include at least one of a flexible polymer layer or a hydrogel layer, and a population of isolated muscle cells expressing a photosensitive membrane transport mechanism seeded on at least one of the flexible polymer layer or the hydrogel layer in a predetermined pattern.

In one embodiment, the tissue structure can be an anisotropic muscle tissue structure.

In one embodiment, the method can include stimulating the tissue structure with a light source providing photostimulation to the tissue structure, the photostimulation resulting in the contractile function of the tissue structure.

In one embodiment, the method can include providing photostimulation to the tissue structure at specific wavelengths of light and specific optical pacing frequencies to control contraction of the tissue structure to mimic normal tissue or diseased tissue.

In one embodiment, the method can include providing photostimulation to the tissue structure in a predetermined spatiotemporal pattern of light with the light source. Providing photostimulation to the tissue structure in the predetermined spatiotemporal pattern of light with the light source can include illuminating a first portion of the tissue structure with a first set of optical pulses at a substantially constant frequency. Providing photostimulation to the tissue structure in the predetermined spatiotemporal pattern of light with the light source can include illuminating a second portion of the tissue structure with an additional optical pulse for cross-field stimulation, a temporal interval between a pulse in the first set of optical pulses and the additional optical pulse resulting in a spiral wave pattern of contraction.

In one embodiment, the method can include illuminating the tissue structure with one or more optical pulses that result in degradation of the spiral wave pattern of contraction and reestablishment of a single wave front of contraction.

In one embodiment, illuminating the first portion of the tissue structure with the first set of optical pulses at the substantially constant frequency can include illuminating the first portion of the tissue structure along a line at or near an edge of the tissue structure.

In one embodiment, providing photostimulation to the tissue structure in a predetermined spatiotemporal pattern of light with the light source can include illuminating the first portion of the tissue structure along a line with a first set of optical pulses at a substantially constant frequency. In one embodiment, providing photostimulation to the tissue structure in the predetermined spatiotemporal pattern of light with the light source can include illuminating a second portion of the tissue structure with a first additional optical pulse for cross-field stimulation with a first temporal interval between a pulse in the first set of optical pulses and the first additional optical pulse. In one embodiment, providing photostimulation to the tissue structure in a predetermined spatiotemporal pattern of light with the light source can include illuminating the second portion of the tissue structure with a second additional optical pulse for cross-field stimulation with a second temporal interval between a pulse in the first set of optical pulses and the first additional optical pulse.

In one embodiment, the method can include determining a temporal interval vulnerability window based on whether each additional optical pulse resulted in a spiral wave pattern of contraction.

In one embodiment, providing photostimulation to the tissue structure in the predetermined spatiotemporal pattern of light with the light source can include illuminating a first portion of the tissue structure along a line with sets of optical pulses at a substantially constant frequency. In one embodiment, providing photostimulation to the tissue structure in the predetermined spatiotemporal pattern of light with the light source can include illuminating a second portion of the tissue structure with additional optical pulses for cross-field stimulation. A temporal interval between a pulse in the sets of optical pulses and the subsequent additional optical pulse can vary for each subsequent additional optical pulse.

In one embodiment, the method can include adding at least one of a calcium-sensitive dye or a voltage-sensitive dye to the tissue structure.

In one embodiment, the method can include optically measuring movement during contraction of the tissue structure and determining stress of the tissue structure during contraction with the mechanical sensor system.

In one embodiment, the method can include optically measuring an intensity or spectrum of a synthetic indicator or a genetically encoded fluorescent protein indicator due to change in membrane voltage and in ion concentration of tissue in the tissue structure with the electrophysiological sensor system.

In accordance with another exemplary embodiment, a method of measuring a contractile function is provided. The method includes providing a tissue structure and stimulating the tissue structure to cause contractile function of the tissue structure. The method includes simultaneously measuring a mechanical activity associated with contraction of the tissue structure with a mechanical sensor system and an electrophysiological activity associated with contraction of the tissue structure with an electrophysiological sensor system.

In one embodiment, the method can include stimulating the tissue structure with a light source providing photostimulation to the tissue structure.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIGS. 3A-C illustrate exemplary muscle tissues or complexes in accordance with exemplary embodiments of the present disclosure.

FIG. 49 illustrates light elicited action potentials and cell contraction through a ChR2-mediated inward current in accordance with embodiments of the present disclosure.

FIG. 50 illustrates hyperpolarization of a tissue structure through a NpHR-mediated outward current in accordance with embodiments of the present disclosure.

FIG. 57 illustrates a morphology of native tissue without ChR2 in accordance with embodiments of the present disclosure.

FIG. 58 illustrates a morphology of tissue with ChR2 in accordance with embodiments of the present disclosure.

FIG. 59 illustrates a peak systole for native tissue without ChR2 and tissue with ChR2 in accordance with embodiments of the present disclosure.

FIG. 60 illustrates stress for native tissue without ChR2 and tissue with ChR2 in accordance with embodiments of the present disclosure.

DETAILED DESCRIPTION

Figure 1:
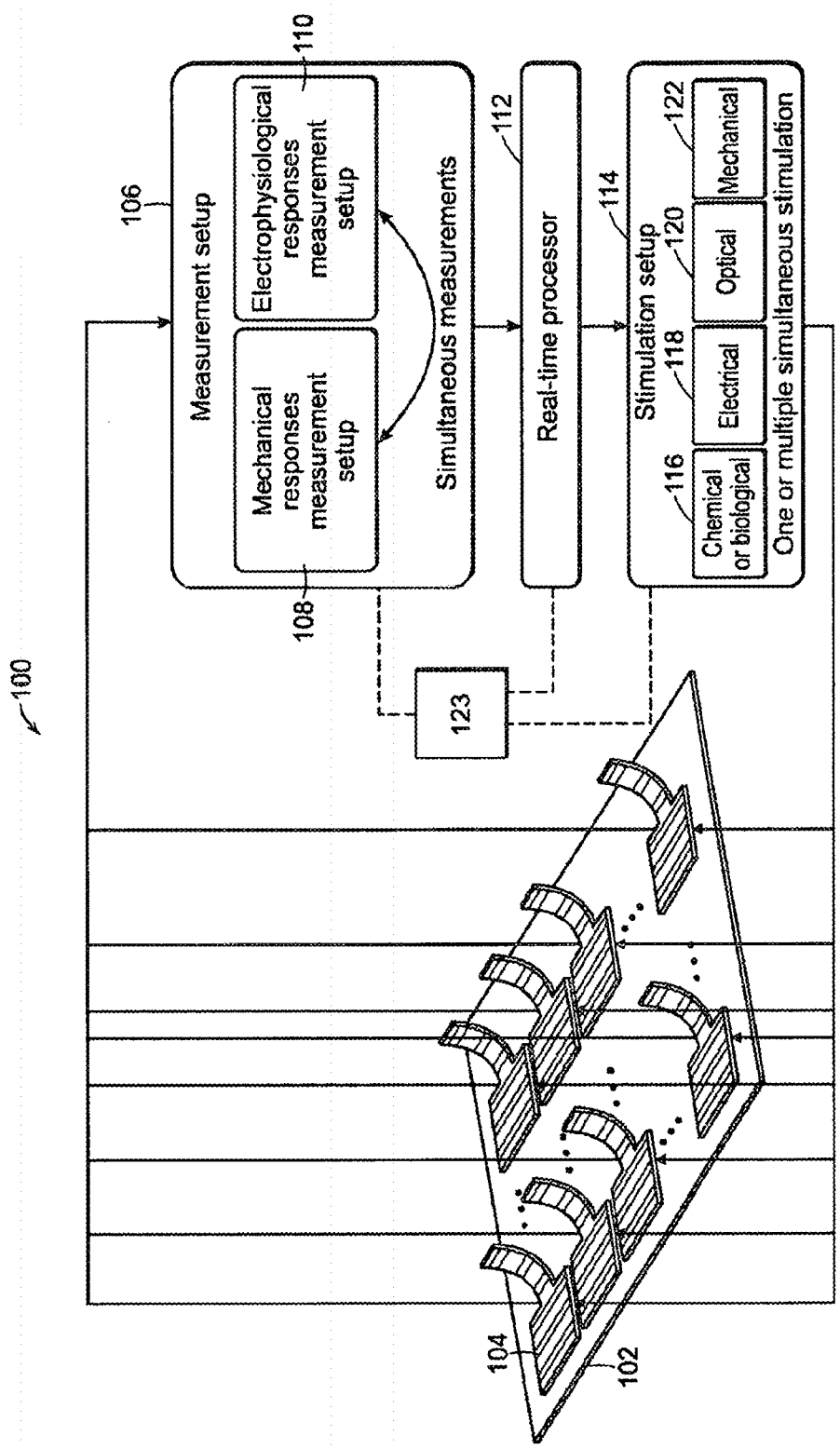
FIG. 1 illustrates an exemplary contractile function measuring system in accordance with exemplary embodiments of the present disclosure.

Although devices and methods for in vitro testing of tissue response have been previously employed (see, e.g., U.S. Pat. No. 8,492,150, and U.S. Patent Publication Nos. 2012/0142556 and 2014/0236267, and PCT Publication Nos. WO 2010/127280 and WO 2013/086512), improved systems, devices and methods for simultaneously measuring mechanical and electrophysiological tissue responses are still lacking in the industry.

Accordingly, the present invention solves this problem by providing systems, devices and methods for measuring a contractile function of a tissue structure that generally include a mechanical sensor system and an electrophysiological sensor system configured to simultaneously measure mechanical and electrophysiological activities, respectively, associated with contraction of the tissues structure. In particular, exemplary embodiments provide for a high throughput (e.g., high speed processing) and high content in vitro testing of tissue structures. Simultaneous measurement of the mechanical and electrophysiological activities allows for more accurate and efficient testing of tissue responses.

The exemplary embodiments provide an improved picture of both efficacy and toxicity of therapeutic agents (e.g., chemical and/or biological compounds, drugs, or the like) for various tissue structures (e.g., muscle tissues, or the like), thereby minimizing or preventing false positives and false negatives in the drug screening process.

In some embodiments, the tissue structure can be a muscle thin film structure. Muscle thin films recapitulate the anisotropic two-dimensional architecture of muscular tissue in vitro and allow a study of tissue functionality and response to therapeutic agents. However, it should be understood that any type of tissue structures can be tested with the exemplary embodiments. The exemplary embodiments allow for simultaneous measurement of mechanical and electrophysiological responses for muscle thin films in a single chip. Testing of muscle thin films in a single chip (e.g., a single chamber) provides for a practical, accurate and efficient measurement system.

The exemplary embodiments provide for a high content measurement system. In particular, the exemplary embodiments allow for simultaneous measurement of two properties (e.g., mechanical and electrophysiological) and provide a correlation or coupling between the two properties. For example, the electro-mechanical window that results in a time delay between the electrical and mechanical systole can be a parameter to evaluate proarrhythmia risk of therapeutic agents. Such measurements are possible in the single chamber, simultaneous measurement system.

The exemplary embodiments provide for a high throughput or high speed processing of the tissue structures. The high throughput saves chip area and allows a larger number of tissue structures to be integrated in the same chip size. The high speed of processing due to simultaneous measurement of the mechanical and electrophysiological properties reduces the measurement time of the tissue responses. The exemplary embodiments reduce costs of fabricating such systems due to the smaller chip size and simpler fabrication. For example, optical and/or electrical components can be used to fabricate a single chamber system rather than fabricating two or more separate chambers for separately testing the mechanical and electrophysiological properties.

The exemplary embodiments allow for continuous (or substantially continuous) measurement of two properties of the tissue structure with two separate measurements. The continuous measurement capability creates the ability to conduct chronic experiments in a nonstop manner (e.g., without interruptions).

The exemplary embodiments allow for simultaneous measurement of both mechanical and electrophysiological even if the muscle tissue is in an abnormal state (transient or dynamic), such as muscle tissues with conduction block, alternan, or arrhythmia, in an accurate manner. In particular, conventional measurement systems measure mechanical and electrophysiological properties of tissue responses in two separate chambers at different times, Response of muscle tissue in the pathological state is transient. Therefore, it is difficult to generate the same response with muscle tissue in the pathological state at the two different testing times, making it impossible to measure the irreproducible mechanical and electrophysiological responses of muscle tissue at different times in an accurate manner. The exemplary embodiments solve this issue by allowing for simultaneous measurement of the mechanical and electrophysiological properties during the same testing process.

The exemplary embodiments can be integrated with alternative or additional components to improve the throughput further. In one embodiment, the exemplary embodiments can include a fluidic system (e.g., micro, milli, or the like) providing drug concentrations with multiple microfluidic channels, resulting in a dose-dependent response. In one embodiment, the exemplary embodiments can include optogenetic techniques, such as providing multiple frequencies of drug administration with optogenetic techniques, resulting in a frequency-dependent response. In one embodiment, the exemplary embodiments can include multiple muscle tissues and/or muscle complexes) in the same platform, resulting in responses of various tissues from a single chip. In one embodiment, the exemplary embodiments can include substrates having varying stiffness levels.

The exemplary embodiments can include optical stimulation and/or temperature and $CO_2$ control for chronic exposure to a therapeutic agent or pacing. For example, the exemplary embodiments can be implemented for chronic stimulation of pharmaceutical agents or optical/electrical stimulation for maturity of stem-cell derived cardiomyocytes. The exemplary embodiments can implement optogenetic techniques to selectively stimulate specific cells among a heterogeneous population of tissues on a muscle thin film assay.

With reference to FIG. 1, a diagrammatic view of an exemplary contractile function measuring system 100 (hereinafter "system 100") is provided. The system 100 can include one or more chips or platforms 102 configured to support one or more tissue structures 104 thereon. For example, the tissue structure 104 can be a muscle thin film tissue structure. The tissue structure 104 can be a muscle tissue or tissue complex including at least one type of muscle cell cultured on a flexible polymer or hydrogel layer. In some embodiments, the muscle type can be cardiac muscle, skeletal muscle, smooth muscle, neuromuscular muscle, or the like. One end of the flexible polymer layer of the tissue structure 104 can be secured to the platform 102. As shown in FIG. 1, multiple tissue structure 104 can be mounted to a single platform 102.

The system 100 can include a measurement system 106 communicatively connected to the platform 102. The measurement system 106 can include a mechanical sensor system 108 and an electrophysiological sensor system 110 configured to simultaneously measure the mechanical and electrophysiological properties or activities associated with responses of the same tissue structures 104. Simultaneous or pseudo-simultaneous measurement of the electrophysiological and mechanical properties allows for high content screening at the tissue level and measurement of the electro-mechanical drug response (e.g., the electro-mechanical window). The system 100 can include a processor 112 (e.g., a real-time processor) communicatively connected to the measurement system 106 in a wired and/or wireless manner. The processor 112 can include computer-executable instructions therein for actuating and regulating the implementation of components of the measurement system 106.

The system 100 can include a stimulation system 114 communicatively connected to the measurement system 106 and/or the processor 112 in a wired and/or wireless manner. The stimulation system 114 can send and/or receive computer-executable instructions to/from the processor 112 for sending one or more stimuli to the tissue structures 104. In particular, the stimulation system 114 can be connected to the platform 102 such that the desired stimulations of the tissue structures 104 can be achieved upon actuation by the processor 112. In some embodiments, the stimulation system 114 can include a chemical/biological engine 116, an electrical engine 118, an optical engine 120 and a mechanical engine 122. Each engine 116-122 can be actuated by the processor 112 to impart the respective stimulation to the tissue structure 104. In one embodiment, the processor 112 can actuate a single engine from the engines 116-122 at each time. In one embodiment, the processor 112 can actuate two or more engines 116-122 at each time. In one embodiment, the processor 112 can actuate two or more engines 116-122 in a patterned and/or sequential manner.

After a stimuli is sent to a tissue structure 104, the measurement system 106 can simultaneously measure the mechanical and electrophysiological response of the same tissue structure 104. The system 100 can include a graphical user interface (GUI) 123 through which the processor 112 can display the data gathered by the measurement system 106. The system 100 can further include input/output devices (e.g., a keyboard, a mouse, or the like) for inputting instructions into the processor 112 through the GUI 123. The GUI 123 can be communicatively connected to the measurement system 106, the processor 112 and/or the stimulation system 114.

Figure 2:
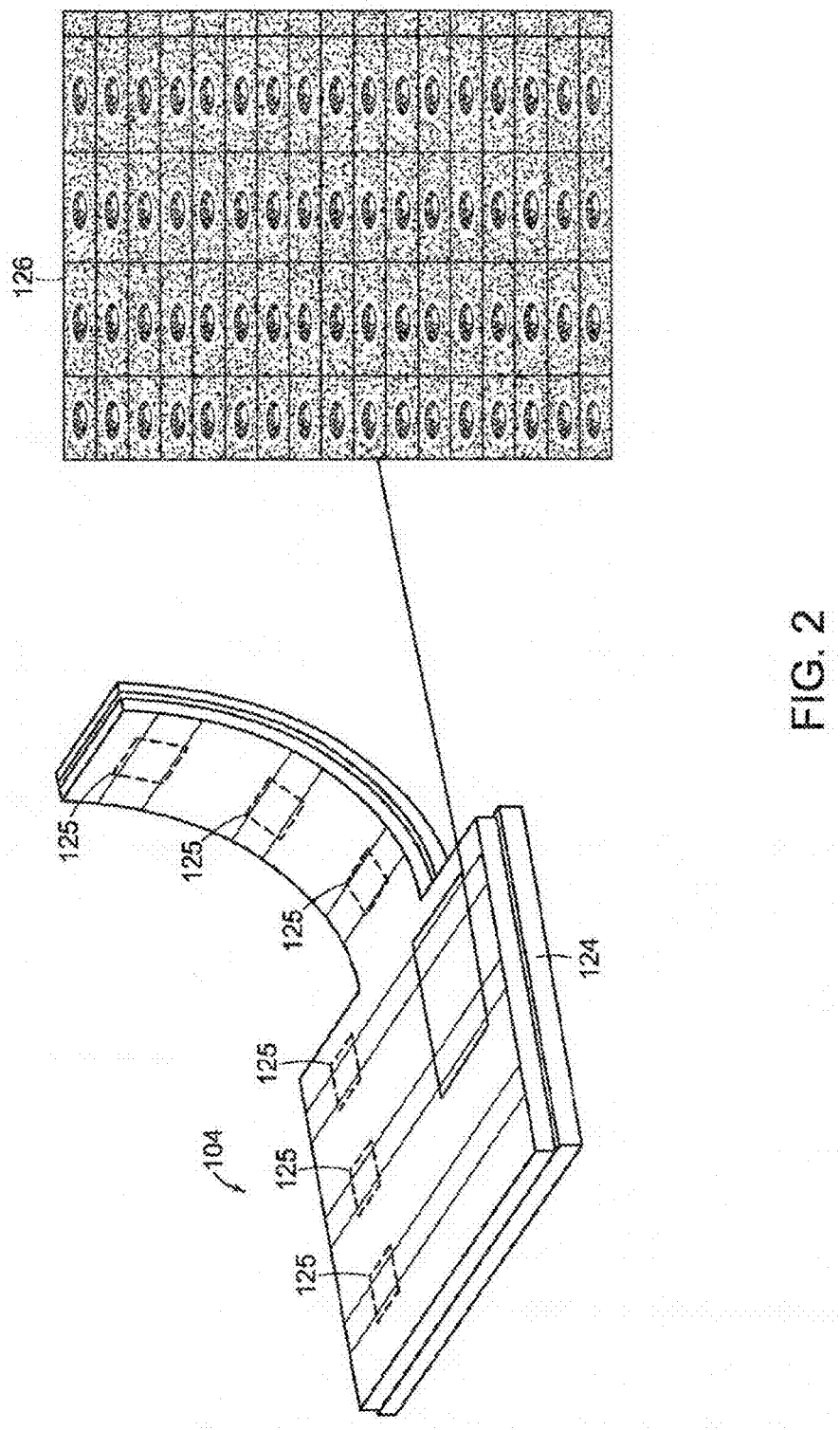
FIG. 2 illustrates an exemplary tissue structure in accordance with exemplary embodiments of the present disclosure.

With reference to FIG. 2, each tissue structure 104 can include a flexible polymer layer 124 that includes a polymer (e.g., polydimethylsiloxane (PDMS), or the like) and/or a hydrogel. Engineered muscle tissue or muscle complex 126 can be positioned or mounted on the polymer layer 124 to form the tissue structure 104. In some embodiments, one or more types of sensors 125 (e.g., electrical sensors, electrodes, or the like) can be embedded or incorporated into the tissue structure 104 for measuring responses of the tissue contraction. In some embodiments, the muscle tissue or muscle complex 126 can be an anisotropic engineered muscle tissue with stimulators and/or sensors. The stimulators can be light sensitive ion channels. The sensors can be voltage (and/or calcium) sensitive fluorescent dyes (and/or proteins).

A variety of wavelengths of light can be used to stimulate the light sensitive ion channels. Different light sensitive ion channels have different sensitive wavelength ranges to respond to light. Most light sensitive ion channels (e.g., ChR2, ChR2$_R$, ChETA$_4$, TC, ChETA$_{TC}$, CatCh, Ch1EF, FR, GR, C1V1$_T$, C1V1$_T$, or the like) can be stimulated with visible light wavelengths of between approximately 400 nm and approximately 600 nm. (See, e.g., Mattis et al., Nature Methods (2012)).

FIGS. 3A-C show exemplary muscle tissues or complexes that can be used with the tissue structure 104. For example, FIG. 3A shows a homogeneous population of muscle tissue 128. The muscle tissue can be, e.g., cardiac muscle, smooth muscle, skeletal muscle, any stem cells derived from muscle, or the like. FIG. 3B shows a heterogeneous population of muscle tissue 128 combined with other types of muscle or non-muscle tissues 130. In particular, the tissue or muscle complex 126 of FIG. 3B can be at least two types of muscle cells including, e.g., cardiac muscle, smooth muscle, skeletal muscle, any stem cells derived from muscle, or the like, resulting in a heterogeneous population. FIG. 3C shows a patterned population of muscle tissue 128 combined with other types of muscle or non-muscle tissues 130. In particular, the tissue or muscle complex 126 of FIG. 3C includes at least two types of muscle cells and each type of muscle cell is physically connected with each other, but isolated from each other, resulting in a patterned population. Specifically, the tissues 130 are grouped together and separated from the muscle tissue 128.

In some embodiments, the muscle cells can be physically connected with any excitable non-muscle cells (e.g., neurons). In some embodiments, at least one type of muscle cell can be physically connected with any alternative cells to provide an excitable ion current to adjacent muscle tissues (e.g., mesenchymal stem cells, any type of stem cells, human embryonic kidney 293 cells (HEK293), Chinese hamster ovary cell (CHO), or the like. In some embodiments, the muscle cells can be physically connected with any cells to provide a functional interaction with adjacent muscle tissues (e.g., fat cells, immune cells, epithelial cells, or the like). The formations can be heterogeneous or patterned populations.

In some embodiments, the mechanical sensor system 108 can optically measure the movement of the tissue structure 104 contraction and calculates the stress of the tissue structure 104. For example, the mechanical sensor system 108 can be a bright field microscopy, dark field microscopy, combinations thereof, or the like. In some embodiments, the mechanical sensor system 108 can electrically measure the stress of the tissue structure 104 with one or more electrical sensors embedded into the tissue structure 104. In some embodiments, the electrical sensor can be in the form of a strain gage, a piezoresistive sensor, or the like, and can measure a change in electrical resistance due to the stress of the tissue structure 104 during contraction. In some embodiments, the electrical sensor can be in the form of a piezoelectrical sensor and can measure a change in electrical current due to the stress of the tissue structure 104 during contraction. In some embodiments, the electrical sensor can be in the form of a magnetic sensor and can measure a change in inductance due to the stress of the tissue structure 104 during contraction.

In some embodiments, the electrophysiological sensor system 110 can optically measure the change in intensity or spectrum of synthetic or genetically encoded fluorescent protein indicators due to change in a membrane voltage and in the ion concentration of the tissue in the tissue structure 104. For example, the electrophysiological sensor system 110 can include a synthetic indicator (e.g., a voltage indicator, such as RH237, Di-4, Di-8, or the like; a calcium indicator, such as Fluo-4, Rhod-2, X-Rhod-1, or the like; an ion indicator, combinations thereof, or the like). As a further example, the electrophysiological sensor system 110 can include a genetically encoded fluorescent protein indicator (e.g., a voltage indicator, as described in International Patent Publication No. WO 2012/027358; a calcium indicator, as described in International Patent Publication No. WO 2014/059154; an ion indicator, combinations thereof, or the like).

In some embodiments, the electrophysiological sensor system 110 can electrically measure the change in membrane voltage and in ion concentration of the tissue in the tissue structure 104 in which one or more electrodes can be embedded. For example, the electrophysiological sensor system 110 can gather intracellular recordings with the electrodes (e.g., patch-clamp technology, planer patch-clamp technology, or the like). As a further example, the electrophysiological sensor system 110 can gather extracellular records with the electrodes (e.g., microelectrode arrays, or the like).

A variety of configurations for integrating the mechanical and electrophysiological sensor systems 108, 110 are contemplated. In some embodiments, an optical mechanical sensor system 108 can be integrated with an optical electrophysiological sensor system 110 (e.g., an optical mapping system). For example, two different microscopy methods can be used, such as dark field illumination for measurement of mechanical activities and fluorescent microscopy for measurement of electrophysiological activities during contraction. In some embodiments, an optical mechanical sensor system 108 can be integrated with an electrical electrophysiological sensor system 110. Inherent decoupling may occur. However, the system 100 can include a noise cancellation circuit to block photosensitive current of the electrical circuit, thereby preventing interference between the signals.

In some embodiments, an electrical contractile measurement system can be integrated with an optical electrophysiological activity measurement system (e.g., an optical mapping system). Inherent decoupling may occur. However, the system 100 can include a noise cancellation circuit to block photosensitive current of the electrical circuit, thereby preventing interference between the signals. In some embodiments, an electrical contractile measurement system can be integrated with an electrical electrophysiological activity measurement system. Isolation of the two electrical circuits can be made, including techniques to reduce and decouple noise from the two different signal sources (e.g., a modulator/demodulator circuit, or the like). Thus, interference between the two signals can be prevented, allowing for simultaneous mechanical and electrophysiological property measurement in a single chamber.

The mechanical sensor system 108 can measure a variety of mechanical response parameters or properties. For example, the mechanical sensor system 108 can measure a change in diastolic stress, peak systolic stress, twitch stress, maximum stress rate (dT/dt), combinations thereof, or the like.

The electrophysiological sensor system 110 can measure a variety of electrophysiological response parameters, such as action potential measurements, field potential measurements, ion current data, dispersion, or the like. As an example, the potential measurements can include 1:1 coupling, action potential magnitude, action potential duration, upstroke rate of action potential, refractory period, conduction velocity, action potential wavelength, restitution, combinations thereof, or the like. As an example, the field potential measurements can include 1:1 coupling, field potential peak magnitude, field potential duration, rising speed, refractory period, conduction velocity, field potential wavelength, restitution, combinations thereof, or the like. As an example, the ion current data can include 1:1 coupling, calcium transient magnitude, calcium transient duration, upstroke rate of calcium transient, calcium wave propagation speed, calcium wavelength, combinations thereof, or the like. As an example, the dispersion data can include at least one of temporal, spatial or spatiotemporal dispersion of action potential duration, action potential refractory period, action potential conduction velocity, action potential wavelength, field potential duration, field potential refractory period, field potential conduction velocity, field potential wavelength, calcium transient duration, calcium wave propagation speed, calcium wavelength, combinations thereof, or the like.

In some embodiments, an electro-mechanical coupling (e.g., relationship) from the mechanical and electrophysiological responses can include an electro-mechanical window (EMW), providing a time delay between the electrical and mechanical systole. In general, the electro-mechanical window of drug-treated tissue cannot be measured in practice without simultaneous measurement of the mechanical and electrophysiological responses. The exemplary systems described herein provide the ability to measure the electro-mechanical window. Such measurements allow for additional data gathering with respect to the tested tissue. For example, when measuring the electro-mechanical window of various drugs, toxic drugs can initiate an abnormal physiological response of the tissue, such as reentry, alternan, or the like, which is generally transient. Thus, additional properties and responses of the tissue can be measured and quantified.

As noted above, the stimulation system 114 can provide a variety of stimuli to the tissue structure 104. In particular, the tissue structure 104 can be stimulated chemically, biologically, electrically, optically, mechanically, combinations thereof, or the like. The chemical and/or biological stimulation can be conducted with a fluidic system (micro or milli) to produce various concentrations of one or multiple chemical and/or biological compounds in a single ship, resulting in a high throughput dose-dependent response. The fluidic system can generate multiple concentrations of chemical and/or biological compounds, and/or multiple types of chemical and/or biological compounds in multiple tissue structures 104 over a single chip or a single tissue muscle thin film. The chemical compounds can include, but are not limited to, antiarrhythmic drugs, any type of muscular drugs, neuromuscular junction drugs, any toxicant, or the like. The biological compounds can include, but are not limited to, any virus, yeast, bacteria, DNA containing product, RNA containing product, or the like.

The electrical stimulation can be conducted with one or more extracellular or intercellular electrodes to produce various pacing frequencies in a single chip, resulting in a high throughput rate, use-dependent response. In some embodiments, the electrical stimulation can generate multiple pacing frequencies and/or multiple electrical field intensities using one or more multiple field stimulations or one or more point stimulators. In some embodiments, the pacing frequencies can be, e.g., between approximately 0.5 Hz and approximately 100 Hz, between approximately 0.5 Hz and approximately 5 Hz, between approximately 0.5 Hz and approximately 10 Hz, between approximately 0.5 Hz and approximately 15 Hz, between approximately 0.5 Hz and approximately 20 Hz, between approximately 0.5 Hz and approximately 25 Hz, between approximately 0.5 Hz and approximately 30 Hz, between approximately 0.5 Hz and approximately 35 Hz, between approximately 0.5 Hz and approximately 40 Hz, between approximately 0.5 Hz and approximately 45 Hz, between approximately 0.5 Hz and approximately 50 Hz, between approximately 0.5 Hz and approximately 55 Hz, between approximately 0.5 Hz and approximately 60 Hz, between approximately 0.5 Hz and approximately 65 Hz, between approximately 0.5 Hz and approximately 70 Hz, between approximately 0.5 Hz and approximately 75 Hz, between approximately 0.5 Hz and approximately 80 Hz, between approximately 0.5 Hz and approximately 85 Hz, between approximately 0.5 Hz and approximately 90 Hz, between approximately 0.5 Hz and approximately 95 Hz, between approximately 5 Hz and approximately 100 Hz, between approximately 10 Hz and approximately 100 Hz, between approximately 15 Hz and approximately 100 Hz, between approximately 20 Hz and approximately 100 Hz, between approximately 25 Hz and approximately 100 Hz, between approximately 30 Hz and approximately 100 Hz, between approximately 35 Hz and approximately 100 Hz, between approximately 40 Hz and approximately 100 Hz, between approximately 45 Hz and approximately 100 Hz, between approximately 50 Hz and approximately 100 Hz, between approximately 55 Hz and approximately 100 Hz, between approximately 60 Hz and approximately 100 Hz, between approximately 65 Hz and approximately 100 Hz, between approximately 70 Hz and approximately 100 Hz, between approximately 75 Hz and approximately 100 Hz, between approximately 80 Hz and approximately 100 Hz, between approximately 85 Hz and approximately 100 Hz, between approximately 90 Hz and approximately 100 Hz, between approximately 95 Hz and approximately 100 Hz, or the like, for a variety of muscle tissue types.

In some embodiments, the field intensities can be, e.g., between approximately 0.01 V/cm and approximately 1,000 V/cm, between approximately 0.001 V/cm and approximately 950 V/cm, between approximately 0.001 V/cm and approximately 900 V/cm, between approximately 0.001 V/cm and approximately 850 V/cm, between approximately 0.001 V/cm and approximately 800 V/cm, between approximately 0.001 V/cm and approximately 750 V/cm, between approximately 0.001 V/cm and approximately 700 V/cm, between approximately 0.001 V/cm and approximately 650 V/cm, between approximately 0.001 V/cm and approximately 600 V/cm, between approximately 0.001 V/cm and approximately 550 V/cm, between approximately 0.001 V/cm and approximately 500 V/cm, between approximately 0.001 V/cm and approximately 450 V/cm, between approximately 0.001 V/cm and approximately 400 V/cm, between approximately 0.001 V/cm and approximately 350 V/cm, between approximately 0.001 V/cm and approximately 300 V/cm, between approximately 0.001 V/cm and approximately 250 V/cm, between approximately 0.001 V/cm and approximately 200 V/cm, between approximately 0.001 V/cm and approximately 150 V/cm, between approximately 0.001 V/cm and approximately 100 V/cm, between approximately 0.001 V/cm and approximately 50 V/cm, between approximately 50 V/cm and approximately 1,000 V/cm, between approximately 100 V/cm and approximately 1,000 V/cm, between approximately 150 V/cm and approximately 1,000 V/cm, between approximately 200 V/cm and approximately 1,000 V/cm, between approximately 250 V/cm and approximately 1,000 V/cm, between approximately 300 V/cm and approximately 1,000 V/cm, between approximately 350 V/cm and approximately 1,000 V/cm, between approximately 400 V/cm and approximately 1,000 V/cm, between approximately 450 V/cm and approximately 1,000 V/cm, between approximately 500 V/cm and approximately 1,000 V/cm, between approximately 550 V/cm and approximately 1,000 V/cm, between approximately 600 V/cm and approximately 1,000 V/cm, between approximately 650 V/cm and approximately 1,000 V/cm, between approximately 700 V/cm and approximately 1,000 V/cm, between approximately 750 V/cm and approximately 1,000 V/cm, between approximately 800 V/cm and approximately 1,000 V/cm, between approximately 850 V/cm and approximately 1,000 V/cm, between approximately 900 V/cm and approximately 1,000 V/cm, between approximately 950 V/cm and approximately 1,000 V/cm, between approximately 0.01 V/cm and approximately 5 V/cm, between approximately 0.1 V/cm and approximately 5 V/cm, approximately 1 V/cm, approximately 5 V/cm, approximately 10 V/cm, or the like. The field stimulators can be decoupled in each different chamber.

The optical stimulation can be conducted with one or more optical fibers or micro mirror arrays to produce various spatiotemporal illumination patterns in a single chip. In some embodiments, the optical stimulation can generate multiple pacing frequencies, multiple light intensities, and/or multiple light wavelengths in multiple tissue structures 104 over a single chip or a single muscle thin film. In some embodiments, the spatiotemporal illumination pattern can be a cross field stimulation pattern. The optical stimulation can measure the photo-toxicity of tissues, and creates a light sensitive ion channel current to pace tissues with optogenetic techniques. In some embodiments, the optical stimulation can generate any spatiotemporal illumination patterns using a light-emitting diode (LED) array, an optical fiber array, a micro-mirror array, combinations thereof, or the like.

In some embodiments, creating a light sensitive ion channel current to pace tissues with the optogenetic techniques can include expressing light sensitive ion channels (e.g., channelrhodopsin (ChR2), C1V1, Chrimson, Chronos, SSFO, ArchT, ChETA, NpHR, SwiChR, iC1C2, or the like) in muscle cells (e.g., in muscle tissue), or muscle cells, any excitable non-muscle cells, any cells to provide excitable ion current to adjacent muscle tissues, any cells to provide any functional interaction with adjacent muscle tissue in a tissue complex including at least one type of muscle cell, or the like. In some embodiments, creating a light sensitive ion channel current to pace tissues with the optogenetic techniques can include utilizing expression techniques with tissue specific promoters to express the ion channels selectively to specific types of cells, such as cardiac muscle cells (e.g., cTnT promoter), neurons (e.g., EF1a, hSyn, CaMK11a, hThy1, HCRT), astrocytes (e.g., GFAP), skeletal muscle cells (e.g., CaMK11a), mesenchymal stem cells (e.g., hThe1), or the like. In some embodiments, creating a light sensitive ion channel current to pace tissues with the optogenetic techniques can include utilizing virus patterning techniques to express the ion channels selectively to a certain location of cells. The virus patterning techniques can include micro contact printing, poly(ethylenimine)-catechol (PEI-C), or the like.

The mechanical modulation can be conducted with modification of mechanical properties of the tissue structure 104 to generate various mechanical properties of the substrate in a single chip. In some embodiments, the mechanical modulation can generate multiple intrinsic properties of the tissue structure 104 and/or multiple substrate surface conditions with optical, mechanical and electromagnetical methods. For example, various adhesive materials with different charges or different protein affinities can be used.

The real-time processor 112 of the system 100 can calculate response signals received from the measurement system 106, feeds input signals into the simulation system 114, and stimulates the tissue structure 104. In particular, the mechanical and/or electrophysiological sensor systems 108, 110 can measure the respective data from the tissue structure 104 and, based on the received data, the processor 112 can actuate the appropriate stimulation system 112 components to provide stimuli to the tissue structure 104. The processor 112 can include one or more computing circuits including a field programmable gate array, one or more data acquisition boards, and one or more software components configured to store and execute computer-executable instructions.

In some embodiments, a long-term culture, $CO_2$ and/or temperature control system can be integrated into the system 100. In some embodiments, any cells (e.g., epithelial cells, fat cells, astrocytes, or the like) seeding on a porous membrane or in a separate chamber can indirectly contact with muscle tissues or muscle complexes by sharing the medium, and provide chemical and biological compounds for the tissues on the platform 102.

Figure 4:
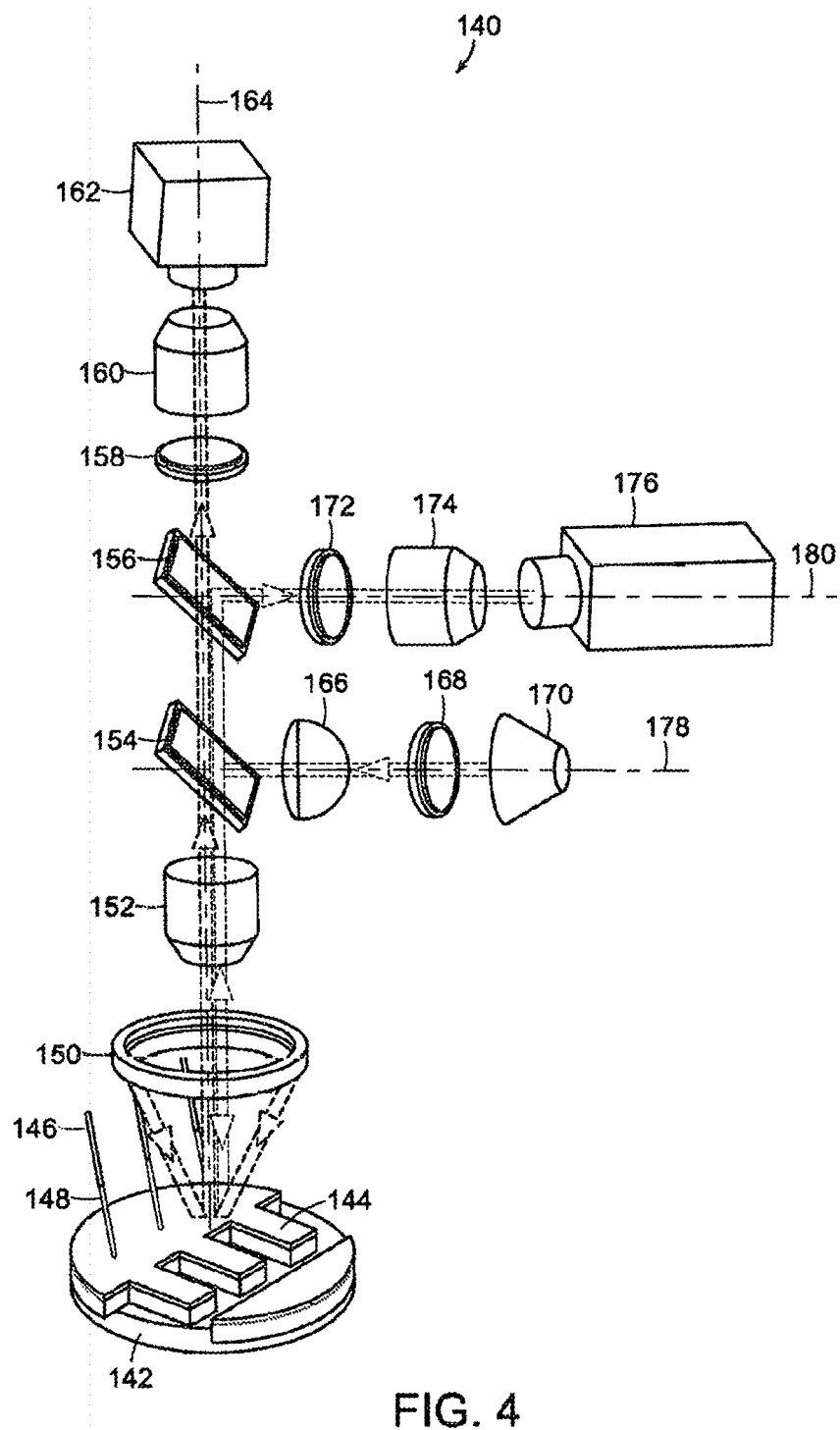
FIG. 4 illustrates an exemplary contractile function measuring system in accordance with exemplary embodiments of the present disclosure.
Figure 42:
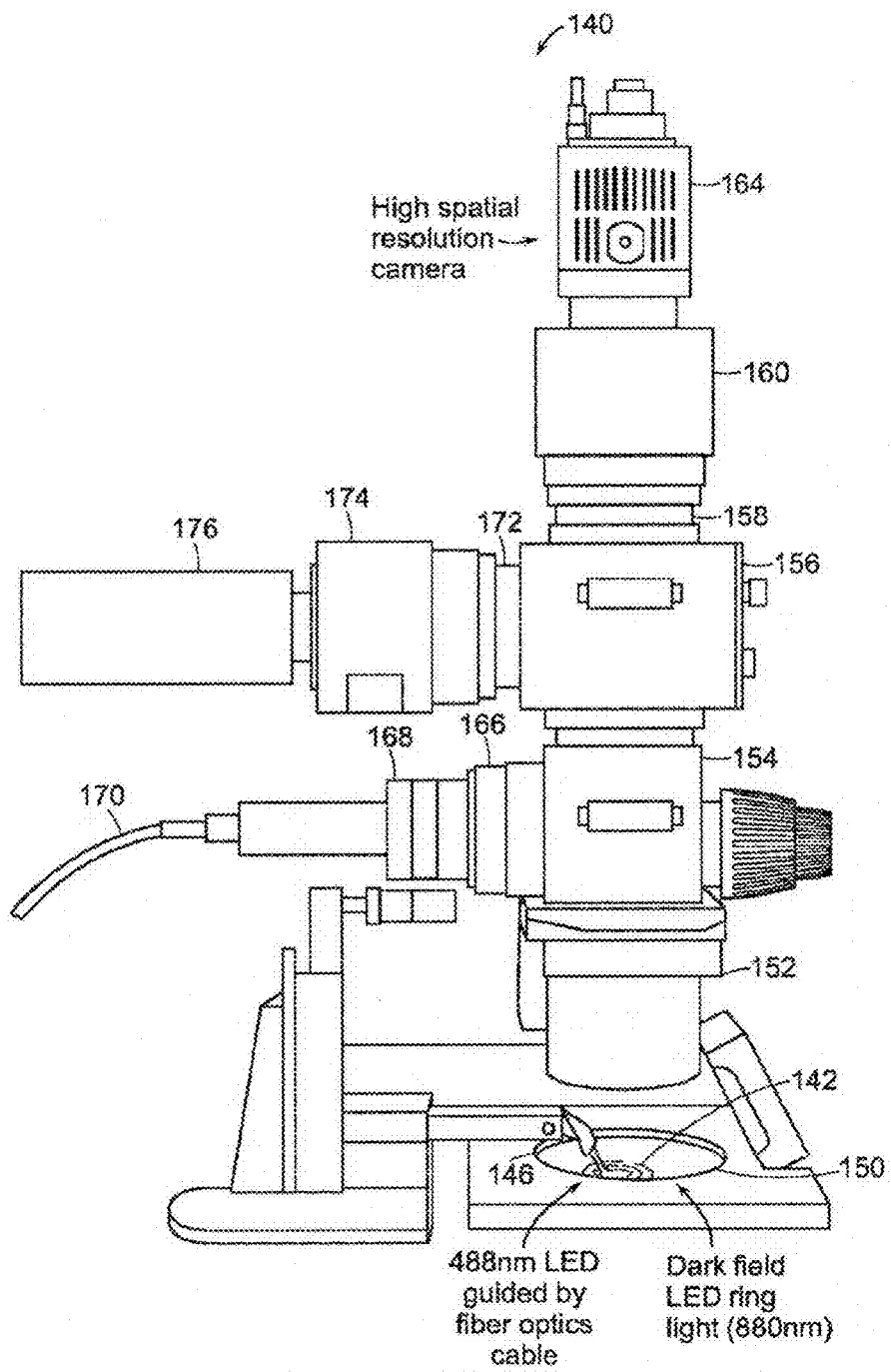
FIG. 42 illustrates a prototype of an exemplary contractile function measuring system of FIG. 4.

FIG. 4 illustrates a setup for an exemplary contractile function measuring system 140 (hereinafter "system 140"). FIG. 42 shows an exemplary prototype of the system 140 which was used to obtain the experimental results discussed below. The system 140 can include a platform 142 with one or more tissue structures 144 positioned and supported thereon. The system 140 can include one or more light sources 146 (e.g., an approximately 488 nm LED guided by fiber optic cables, or the like) positioned above the platform 142. The light sources 146 can be configured to provide photostimulation to the tissue structure 144. The system 140 can include a dark field LED ring light 150 (e.g., approximately 880 nm) disposed above the platform 142 and guiding beams onto the tissue structure 144. The system 140 can include a plan apochromatic 1× or 0.63× lens 152 disposed above the right light 150. The system 140 can include a DC mirror 154 (e.g., Rhod-2:580, x-rhod-1:593, or the like) disposed above the lens 152.

The system 140 can include a DC mirror 156 (e.g., 700) disposed above the DC mirror 154. The system 140 can include a low pass (LP) filter 158 (e.g., 664LP) disposed above the DC mirror 156. The system 140 can include a plan apochromatic 1× lens 160 disposed above the filter 158 and oriented in an opposite direction from the lens 152. The system 140 can include a mechanical sensor 162 (e.g., a dark field imaging sensor in the form of a high spatial resolution camera) disposed above the lens 160 configured to capture mechanical movement properties associated with the tissue structure 144. The components 150-162 of the system 140 can be substantially aligned above the platform 142 along a vertical axis 164.

The system 140 can include a collimator 166 disposed along an axis 178 perpendicular to the vertical axis 164 and aligned with the mirror 154. The system 140 can include a band pass (BP) filter 168 (e.g., Rhod-2:563/9, X-rhod-1: 580/14, or the like) disposed adjacent to the collimator 166 and aligned along the axis 178. The system 140 can include a low noise light source 170 disposed adjacent to the BP filter 168 and aligned along the axis 178.

The system 140 can include a BP filter 172 (e.g., Rhod-2:617/73, X-rhod-1: 641/75, or the like) disposed along an axis 180 perpendicular to the vertical axis 164 (and parallel to the axis 178) and aligned with the mirror 156. The system 140 can include a plan apochromatic 1× lens 174 disposed adjacent to the BP filter 172 and aligned along the axis 180. The system 140 can include an electrophysiological sensor 176 (e.g., a high temporal resolution camera in the form of a Rhod-2 or X-rhod-1 ($Ca^{2+}$) sensor) disposed adjacent to the lens 174 and aligned along the axis 180.

Light emitted from the light source 170 can be transmitted by the mirror 154 onto tissue structure 144. The light can further be transmitted to the mirror 156 and retransmitted to the electrophysiological sensor 176. Light emitted by the right light 150 can be transmitted onto the tissue structure 144. The light can further be transmitted to the mechanical sensor 162. The system 140 can measure both the mechanical and calcium handling responses with optical stimulation and with multiple pacing frequencies. As an example, the system 140 can simultaneously measure calcium handling and contractility of an in vitro cardiac muscle thin film assay. The system 140 can be used to measure rate-dependent drug response of cardiac tissue on a single chip. The optical stimulation system can pace the tissue structure 144 expressing a light sensitive ion channel (ChR2) with control of a cardiac specific promoter (cTnT). The optical measurement system (e.g., dark field microscopy with far-red light) can measure the mechanical response based on the contractility stress. The optical measurement system (e.g., fluorescent microscopy with red shift calcium dyes, Rhod-2 and X-rhod-1) can be used to measure the electrophysiological response based on the calcium transient.

The system 140 can measure the calcium handling properties using fluorescent microscopy with the sensor 176, while simultaneously measuring the contractility of the tissue structure 144 using dark field microscopy with the sensor 162. In particular, the system 140 combines an optical mapping system with dark field microscopy for simultaneous contractility and calcium transient measurements. The optical mapping system with a high speed camera can monitor changes in intracellular calcium ion concentration with high temporal resolution, and the dark field microscopy can visualize unstained and transparent samples with high spatial resolution.

To prevent overlay of the excitation light wavelength of both the calcium transients and the contractility measurements with excitation of light sensitive ion channels (e.g., ChR2 has an excitation wavelength of approximately 380-580 nm), a long wavelength intracellular calcium indicator (e.g., X-Rhod-1 with an excitation wavelength of approximately 574 nm) can be used for the calcium transient imaging, and infrared LED lights (e.g., wavelengths of approximately 880 nm) can be used as the light source for dark field illumination. Thus, overlay and interference between the wavelengths is prevented, and simultaneous measurement of mechanical and electrophysiological properties can be achieved. In addition, the system 140 can include a low magnification lens to expand the field of view to an approximately millimeter scale, which is large enough to visualize the electrophysiological and mechanical activities over the tissue structure 144.

Figure 5:
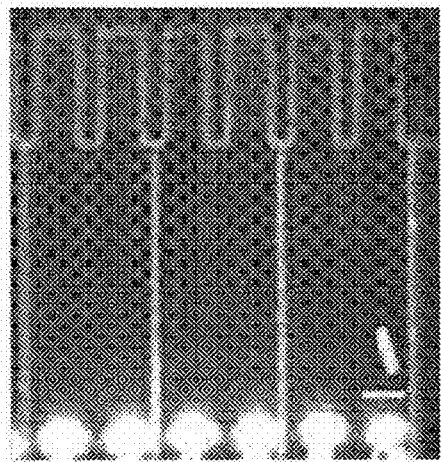
FIG. 5 illustrates a dark field image of a tissue structure assay at diastole for the contractile function measuring system of FIG. 4.
Figure 6:
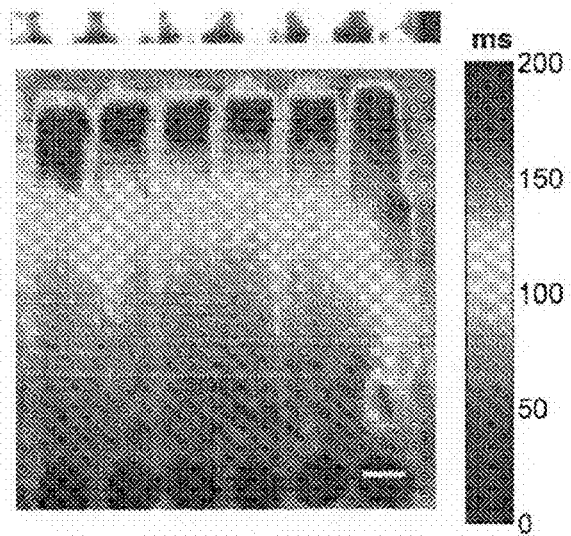
FIG. 6 illustrates an activation map of calcium propagation for the contractile function measuring system of FIG. 4.
Figure 7:
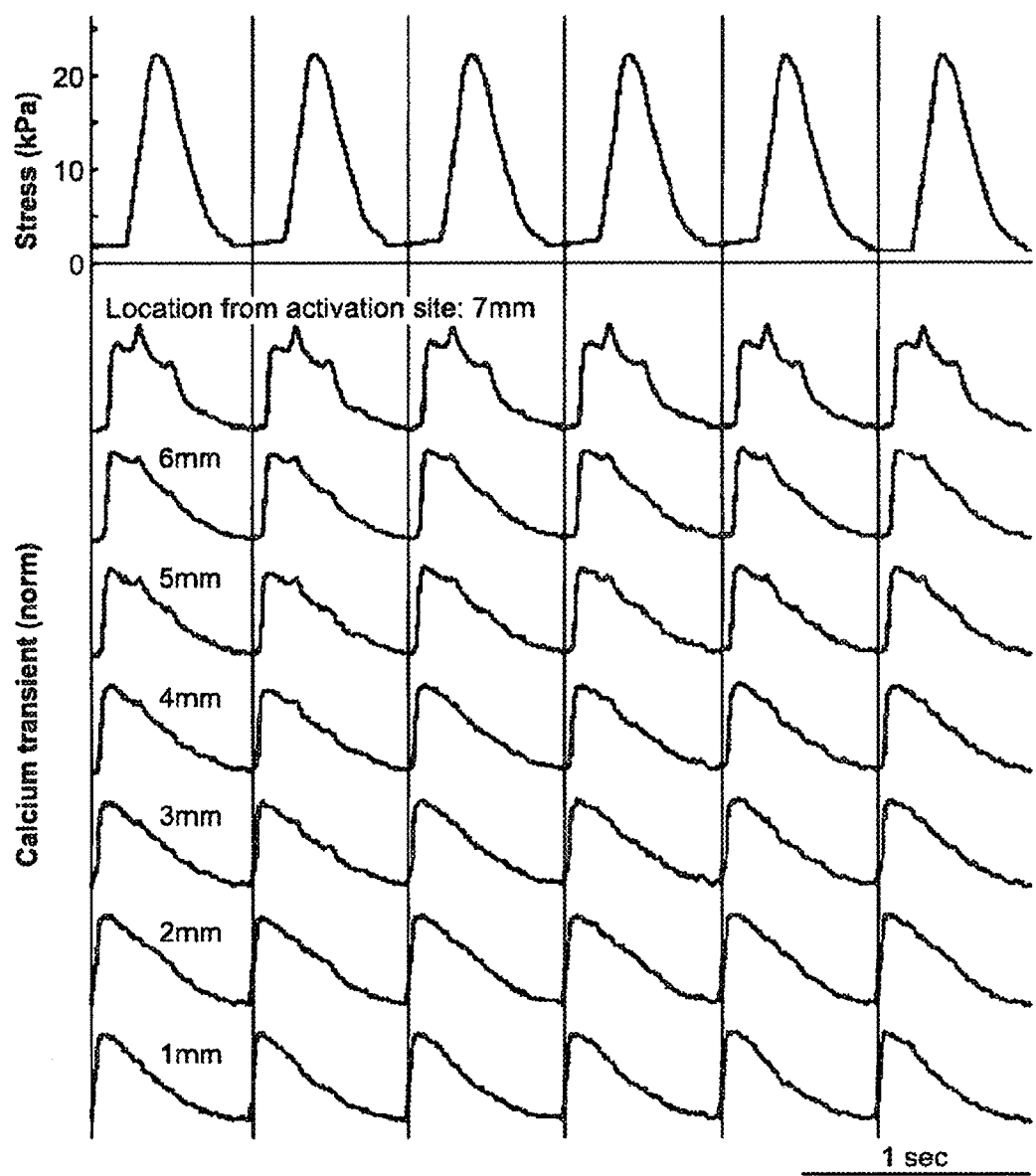
FIG. 7 illustrates a stress trace of the tissue structure and calcium transient traces at various locations from optical fibers for the contractile function measuring system of FIG. 4.
Figure 8:
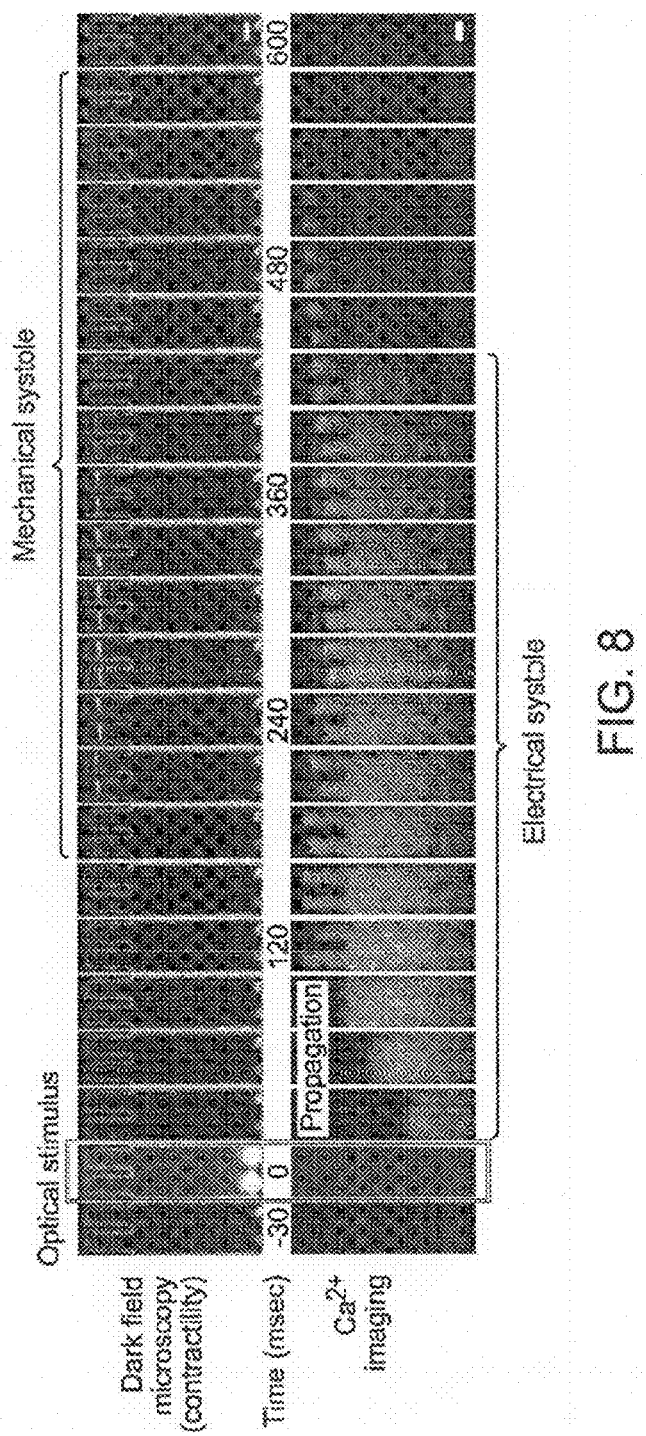
FIG. 8 illustrates time-lapse images from both dark field microscopy and calcium imaging for the contractile function measuring system of FIG. 4.

FIG. 5 shows a dark field image of a muscle thin film assay (i.e., the tissue structure 144) at diastole. FIG. 6 shows an activation map of calcium propagation. FIG. 7 shows the stress trace of muscle thin films and calcium transient traces at various locations from the optical fibers. FIG. 8 shows time-lapse images taken by both dark field microscopy and calcium imaging. The optical illumination guided by the optical fibers from the 488 nm LED light can elicit calcium propagation, followed by mechanical contraction of the muscle thin films. As can be seen from FIG. 8, a stimulus occurs at approximately 0 msec, followed by a time period of electrical systole and calcium propagation, which overlaps with a time period of mechanical systole and contractility.

Still with reference to FIGS. 5-7, during experimentation, optical fibers were used to emit light stimulation at 1.5 Hz for optical stimulation of the tissue structure. In particular, optical stimulation was used for excitation contraction coupling of muscle thin films. Infrared dark field imaging was used for contractility measurements. Red shifted dyes (e.g., Rhod-2, X-rhod-1) were used for calcium sensitive dye imaging. The calcium wave propagation was followed by contraction of the muscle thin film. The muscle thin film combined with calcium imaging enabled simultaneous mechanical properties and calcium handling properties to be measured for higher content assays.

Figure 9:
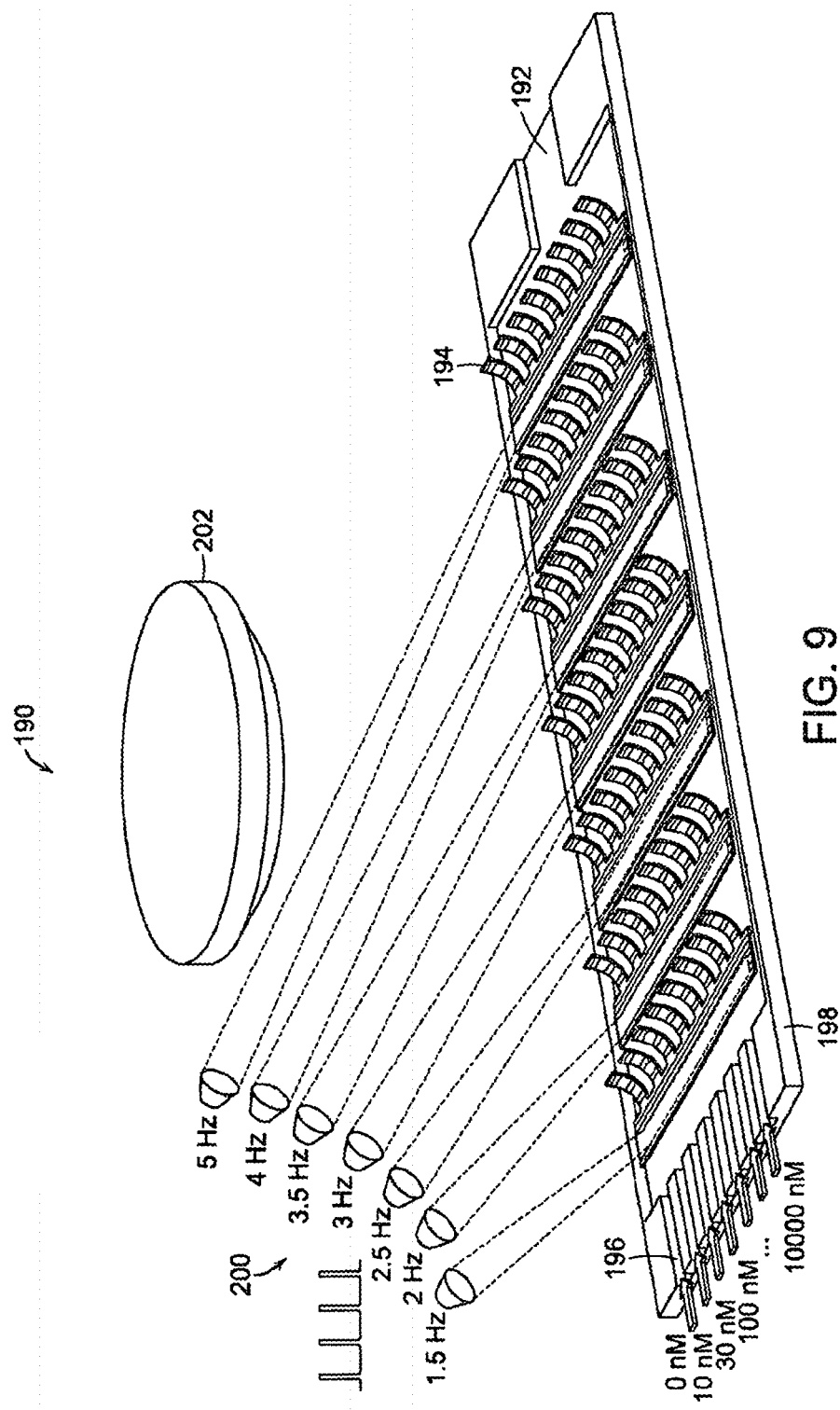
FIG. 9 illustrates an exemplary contractile function measuring system in accordance with exemplary embodiments of the present disclosure.

FIG. 9 illustrates a setup for an exemplary contractile function measuring system 190 (hereinafter "system 190"). The system 190 can include a platform 192 configured to support one or more tissue structures 194. The platform 192 can include a plurality of inlets 196 leading to microfluidic channels 198 formed in the body of the platform 192. The microfluidic channels 198 can be used to introduce different concentrations of and/or different types of chemical and/or biological compounds for stimulating the tissue structures 194. The system 190 can include one or more light sources 200 configured to impart optical stimulation to the tissue structures 194. For example, the light sources 200 can provide patterned optical stimulation guided by micro-mirror arrays and/or optical fiber arrays. As illustrated in FIG. 9, the light sources 200 can emit optical stimulation at varying frequencies. The system 190 can include an optical setup or sensor 202 for measuring the mechanical and/or electrophysiological properties associated with contraction of the tissue structures 194. In some embodiments, the optical setup 202 can include dark field microscopy to measure the contractile stress (e.g., mechanical properties), and a fluorescent microscopy to measure calcium, voltage, or both, in the tissue structure 194 (e.g., electrophysiological properties).

The system 190 thereby combines a fluidic system with optogenetic techniques, enabling simultaneous measurement of dose- and rate-dependent mechanical and electrophysiological responses of the tissue. In particular, the system 190 allows for measurement of mechanical and action potential responses with both chemical and optical stimulation with multiple drug concentrations and multiple pacing frequencies. The optical measurement system can be dark field microscopy with far-red light to measure the mechanical response in the form of contractility stress. The optical measurement system can further be a fluorescent microscopy with red shift voltage dyes (See, e.g., PHG1 as described in Salama, et al., J. Membr. Biol. (2005)), ultraviolet or red-shift calcium dyes, Fura-2, Indo-1, Rhod-2, X-rhod-1, or the like, to measure the electrophysiological response in the form of action potential and/or calcium transient.

As an example, the system 190 can be used to measure both contractility and action potential (or calcium handling) responses with chronic chemical and/or biological and optical stimulation with multiple drug concentrations and multiple pacing frequencies for maturation of stem-derived cardiac tissue. The fluidic system can be used to supplement small molecules, such as triiodothyronine (thyroid hormone) (See, e.g., Lee et al., Mol. Endocrinol. (2010)), microRNA to induce overexpression or downregulation of specific genes (See, e.g., Yamanaka et al., Plos. One (2008)), any material for introducing nucleic acids into tissue to generate genetic, structural or functional remodeling. The system 190 can be used to pace stem cell derived cardiac tissue chronically with various frequencies using optogenetic techniques to optimize maturation protocol of stem cell derived cardiac tissue. In contrast, convention electrical stimulation generally results in toxic side effects which are not appropriate for chromic stimulation, and generates toxic ionic and free radicals due to an irreversible Faradaic reaction (See, e.g., Tulloch et al., Circ. Res. (2011); and Tandon et al., Nature Protocol (2009)). Since synthetic indicators may be toxic for long-term measurement, in some embodiments, the system 190 can be used to conduct long-term measurement of action potential or calcium transient using genetically encoded fluorescent protein indicators. The system 190 can further utilize non-toxic far-red LED light to detect movement of the tissue structure 194.

Figure 10:
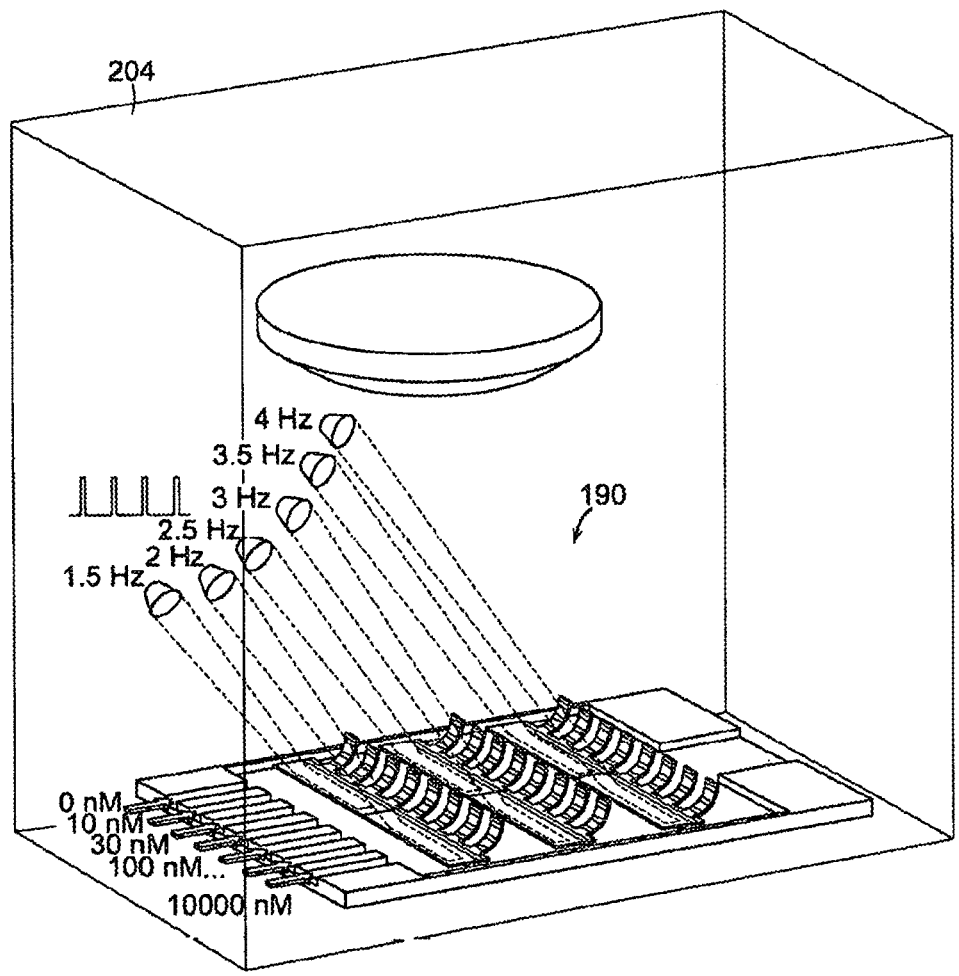
FIG. 10 illustrates an exemplary contractile function measuring system in accordance with exemplary embodiments of the present disclosure.

In some embodiments, as illustrated in FIG. 10, the system 190 can be positioned within an enclosure 204. The enclosure 204 can be a $CO_2$ and/or temperature controlled incubator. Thus, during testing, the $CO_2$ and/or temperature levels within the enclosure 204 can be regulated based on the desired testing parameters. In some embodiments, the processor 112 can be communicatively connected to the enclosure 204 to vary the conditions within the enclosure 204. The enclosure enables dose- and rate-dependent response measurement while the tissue is chronically stimulated with optogenetic methods.

Figure 12:
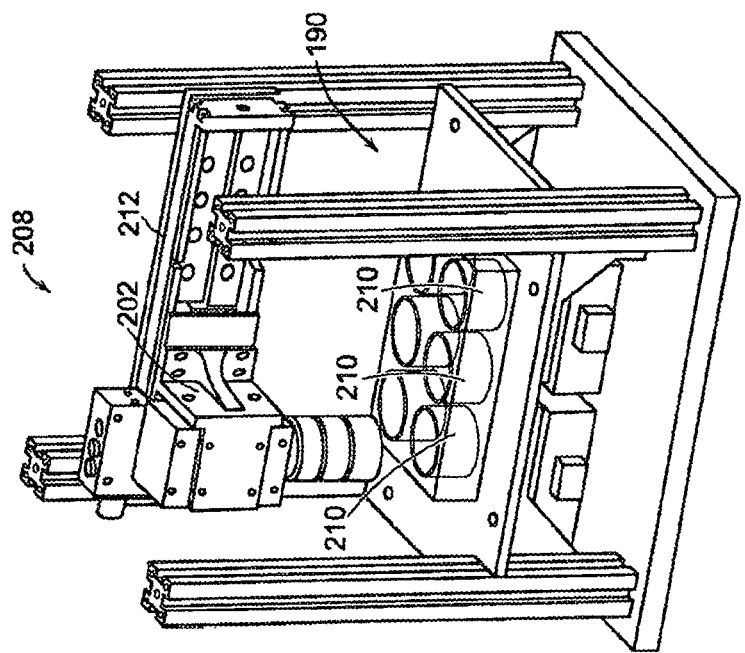
FIG. 12 illustrates a prototype of an exemplary contractile function measuring system in accordance with embodiments of the present disclosure.
Figure 11:
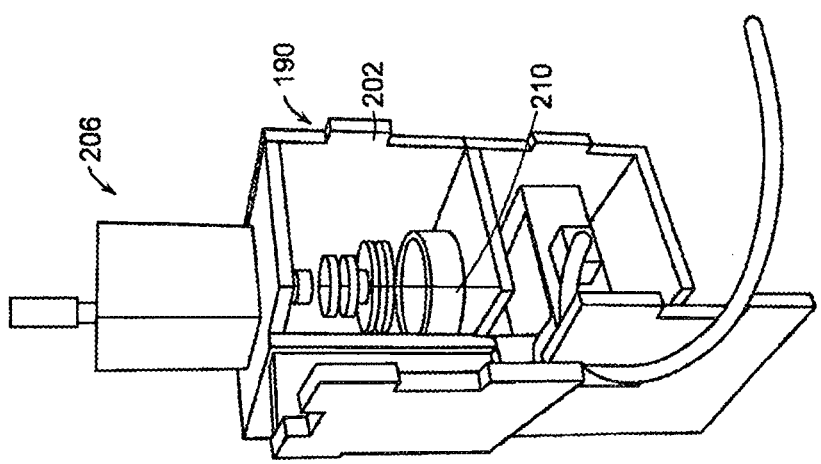
FIG. 11 illustrates a prototype of an exemplary contractile function measuring system in accordance with exemplary embodiments of the present disclosure.

FIG. 11 illustrates an exemplary prototype 206 of a single-well version of the system 190 that enables chronic optical stimulation to light sensitive ion channel expressing tissue. In particular, the optical setup 202 can be positioned directly over a single well 210 in which the tissue structures 192 are positioned. FIG. 12 illustrates another exemplary prototype 208 of a multi-well version of the system 190 that enables chronic optical stimulation to light sensitive ion channel expressing tissue. The multi-well version allows for multiple platforms or chips to be implemented in the setup, thereby allowing for a larger number of tissue structures 194 to be tested. In particular, the optical setup 202 can translate or move along a track 212 to vary the position of the optical setup 202 relative to each of the wells 210.

Figure 13:
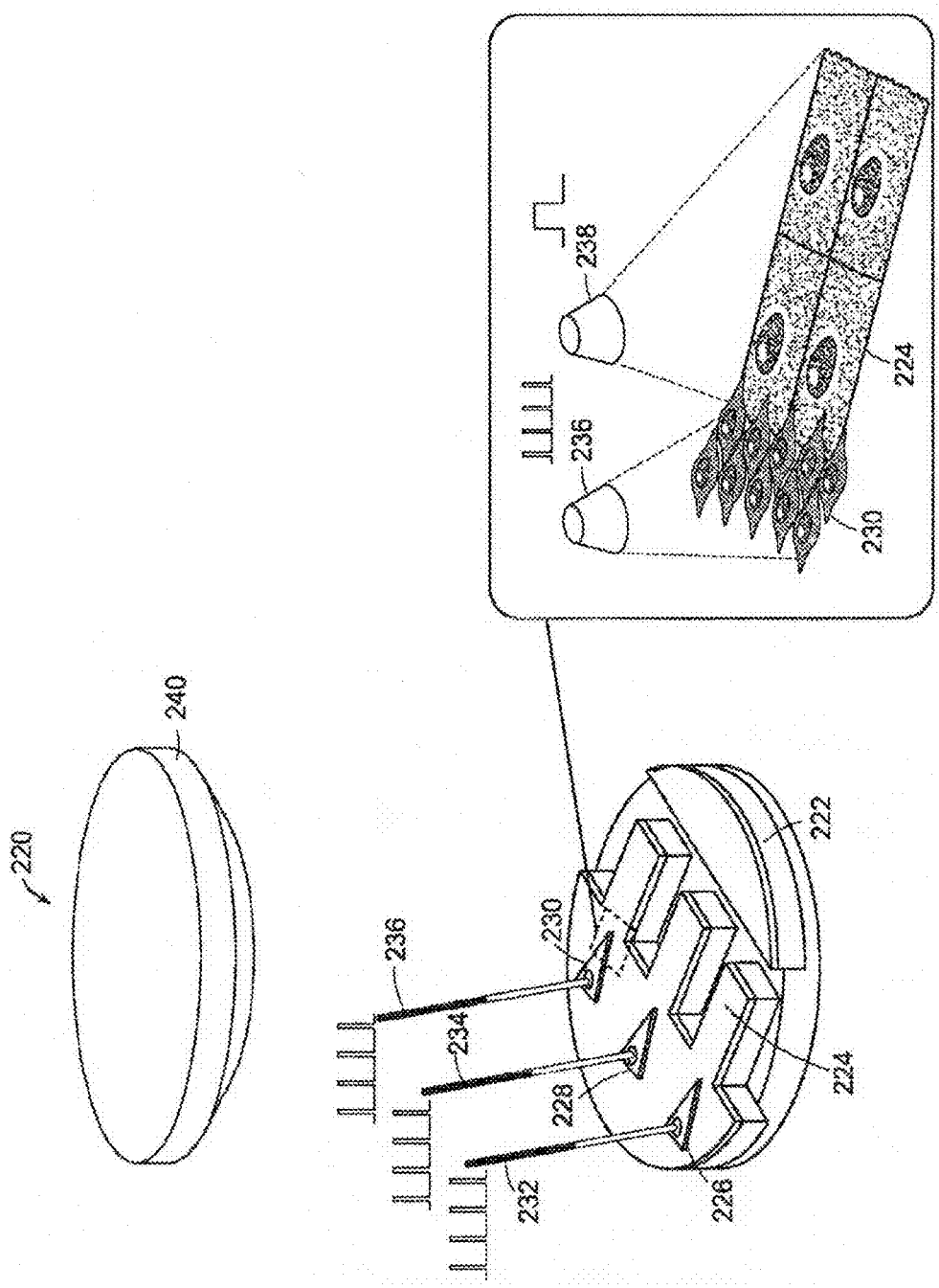
FIG. 13 illustrates an exemplary contractile function measuring system in accordance with exemplary embodiments of the present disclosure.

FIG. 13 illustrates a setup for an exemplary contractile function measuring system 220 (hereinafter "system 220"). The system 220 includes a platform 222 with one or more tissue structures 224 positioned thereon. In some embodiments, the platform 222 can be formed from or includes a PDMS membrane. In some embodiments, the tissue structures 224 can be intact cardiomyocytes. The system 220 can include cells 226, 228, 230 that can be activated with respective light sources 232, 234, 236. In particular, the cells 226, 228, 230 can be tissue complexes including cardiac muscle cocultered with light sensitive ion channel expressing human mesenchymal stem cells (hMSCs) and neurons. For example, the cell 226 can be a C1V1-CM cell with red-activation, the cell 228 can be a ChR2-Neuron cell with blue-activation, and the cell 230 can be a ChR2-hMSC cell with blue-activation. The light sources 232, 234, 236 can be 488 nm LED guided by fiber optic cables that emit light at, e.g., a frequency of approximately 2 Hz.

As shown in the detailed view of FIG. 13, the cells 226, 228, 230 can be connected with the respective tissue structures 224 such that photostimulation of the cells 226, 228, 230 results in contraction of the tissue structures 224. For example, the human mesenchymal stem cells 230 can be interconnected with the tissue structures 224. The light source 236 can provide light stimulation to the cells 230, while a light source 238 can provide light stimulation to the tissue structures 224. In one embodiment, the light source 236 can be a 488 nm LED blue-light activation source and the light source 238 can be a 590 nm LED red-light activation source. The system 220 further includes an optical setup 240 that includes a mechanical and electrophysiological sensor system, such as dark field microscopy for measuring contractile stress and fluorescent microscopy for measuring calcium, voltage, or both, variation.

Figure 15:
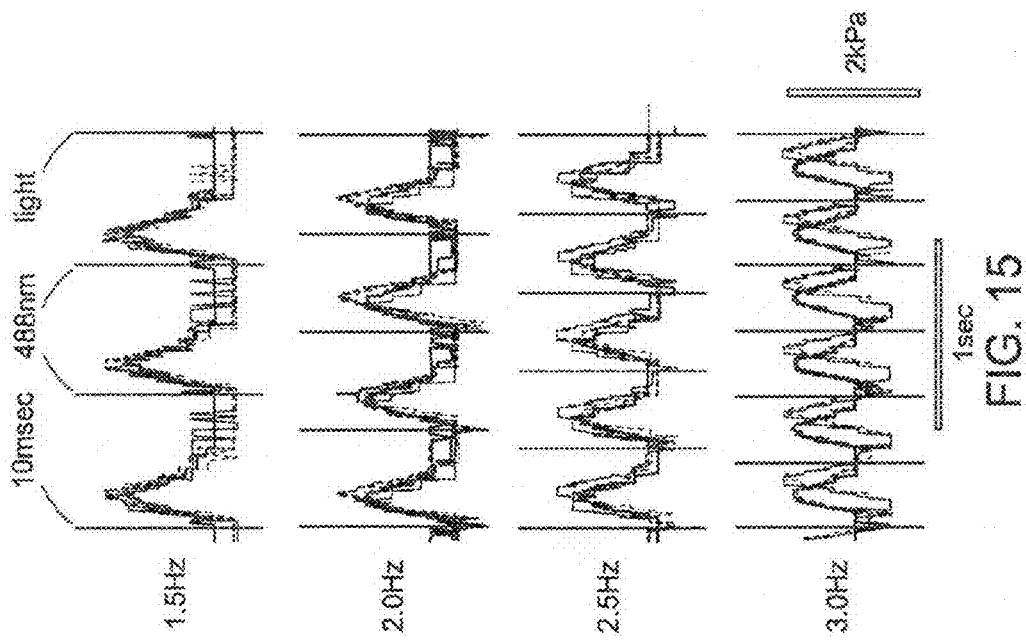
FIG. 15 illustrates contractile stress traces of tissue structures activated in an exemplary contractile function measuring system of FIG. 13.
Figure 14:
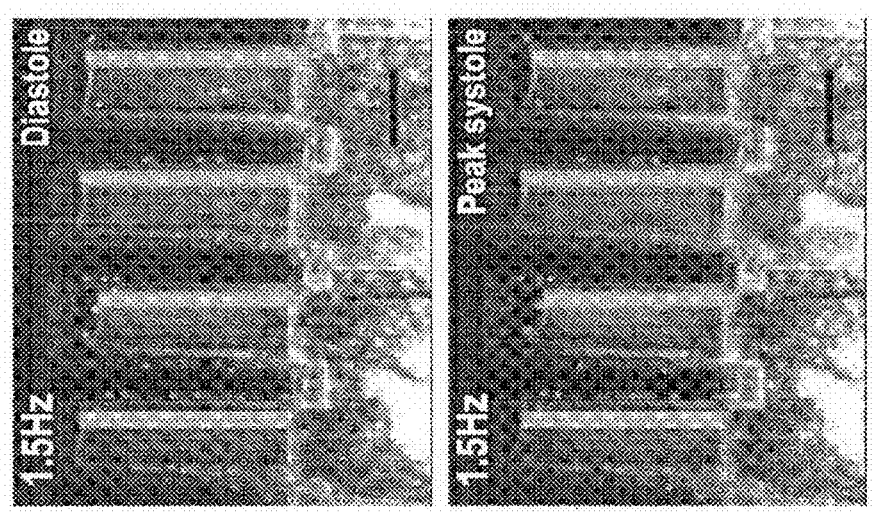
FIG. 14 illustrates diastole and peak systole for tissue structures of an exemplary contractile function measuring system of FIG. 13.

FIG. 14 shows the diastole and peak systole for tissue structures 224 of the system 220. FIG. 15 shows the contractile stress traces of cardiac tissue indirectly activated with hMSCs through blue light stimulated ChR2, a light sensitive channel, in the system 220. The system 220 can be used to indirectly pace cardiac tissue and/or skeletal muscle through a gap junction with human mesenchymal stem cells or through a neuromuscular unction with neurons. The system 220 can also be used to isolate pacemaker cells, which can be cut after maturation of the cardiac issue.

Figure 16:
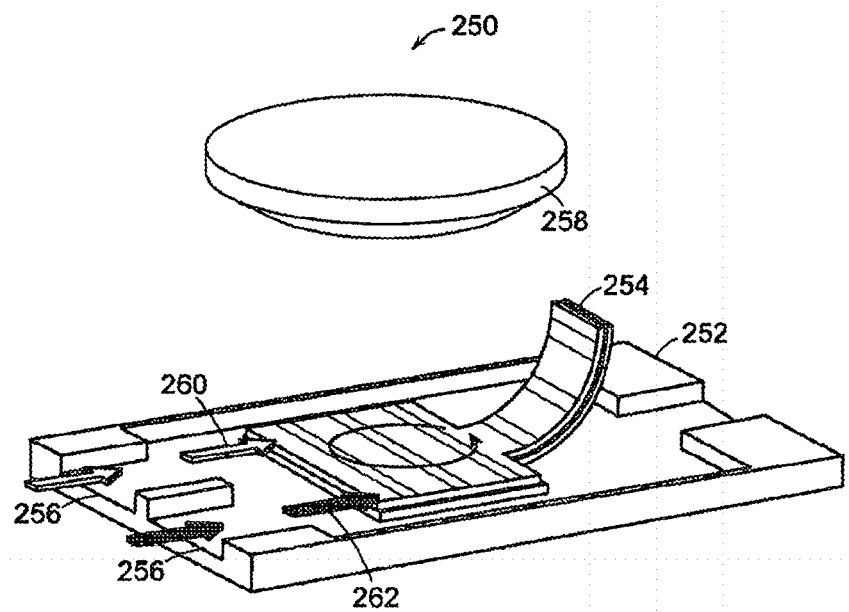
FIG. 16 illustrates an exemplary contractile function measuring system with a chemical gradient in accordance with embodiments of the present disclosure.
Figure 17:
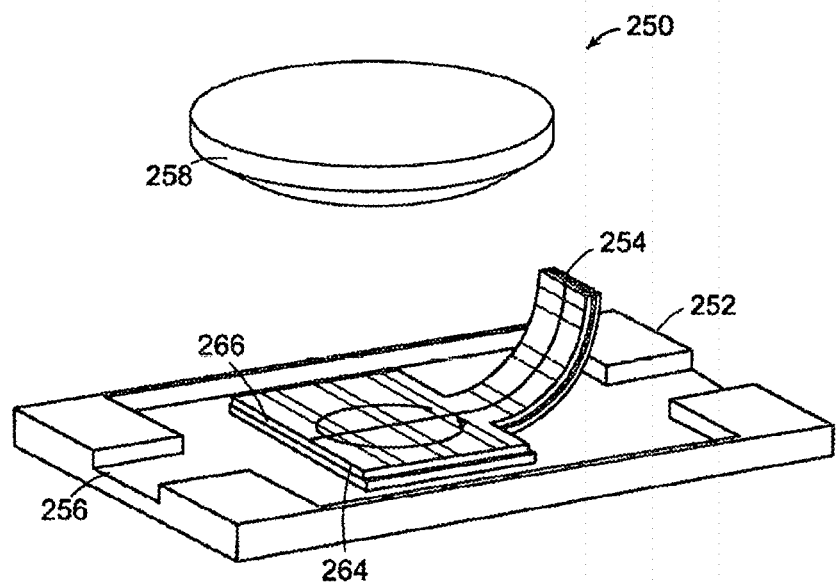
FIG. 17 illustrates an exemplary contractile function measuring system with a mechanical gradient in accordance with embodiments of the present disclosure.

FIGS. 16 and 17 illustrate a setup for an exemplary contractile function measuring system 250 (hereinafter "system 250"). The system 250 includes a platform 252 configured to support one or more tissue structures 254 thereon. The platform 252 can include channels 256 of a fluidic system that allow introduction of chemical and/or biological concentrations therethrough for activation of the tissue structures 254. The system 250 further includes an optical setup 258 for measuring mechanical and electrophysiological properties of the tissue structure 254.

The system 250 can allow for creation of a chemical or mechanical gradient. In particular, the chemical gradient can be generated by the fluidic system, inducing inhomogeneity in a refractory period, leading to reentrant arrhythmia. The mechanical gradient can be generated by controlling activities of a cross-linked in a hydrogel and also induces abnormalities of mechanical contractility, leading to reentrant arrhythmia. The optical setup 258 can detect and measure these intransient cardiac activities.

For example, as shown in FIG. 16, a gradient of chemical concentration can be introduced to a single muscle thin film. In particular, a low concentration 260 of an anti-arrhythmic drug can be introduced through one channel 256 to one portion (e.g., half) of the tissue structure 254, and a high concentration 262 of an anti-arrhythmic drug can be introduced through another channel 256 to a second portion (e.g., a second half) of the tissue structure 254. Introduction of the therapeutic agent at different concentrations to different portions of the tissue structure 254 can induce an arrhythmia in the cardiac muscle tissue due to a chemical gradient. Chemical stimulation of one or more tissue structures 254 on a single platform 252 can be performed in this manner. Drug-induced inhomogeneity can be simulated in a refractory period, which generates functional reentry. Transient cardiac activities can be detected by using simultaneous contractility and action potential (or calcium handling) responses. Drug toxicity can be quantified by generating the chemical gradient with various antiarrhythmic agents.

As a further example, as shown in FIG. 17, the tissue structure 254 can include a stiff, highly cross-linked hydrogel 264 at one portion (e.g., a first half), and includes a soft, lower cross-linked hydrogel 266 at a second portion (e.g., a second half). The gradient of the mechanical stiffness in a single muscle thin film can induce arrhythmia in the cardiac muscle tissue. The stiffness can be measured in one or more tissue structures 254 on a single platform 252. Inhomogeneity of the substrate stiffness can be generated by controlling the cross-linker in the hydrogel. Infraction induces alterations in the mechanical properties of non-infarcted myocardium, such as myocardial stiffness. Modulating the substrate stiffness can accelerate maturation or pathogenesis of stem cell derived cardiac tissue (See, e.g., Jacot et al., Acad. Sci., Ann, NY (2010)). Transient cardiac activities can be detected by using simultaneous contractility and action potential (or calcium handling) responses. A disease model can be developed using an inhomogeneous substrate to test chemical compounds. The maturation or pathogenesis protocols can be optimized by modulating the substrate stiffness.

Figure 18:
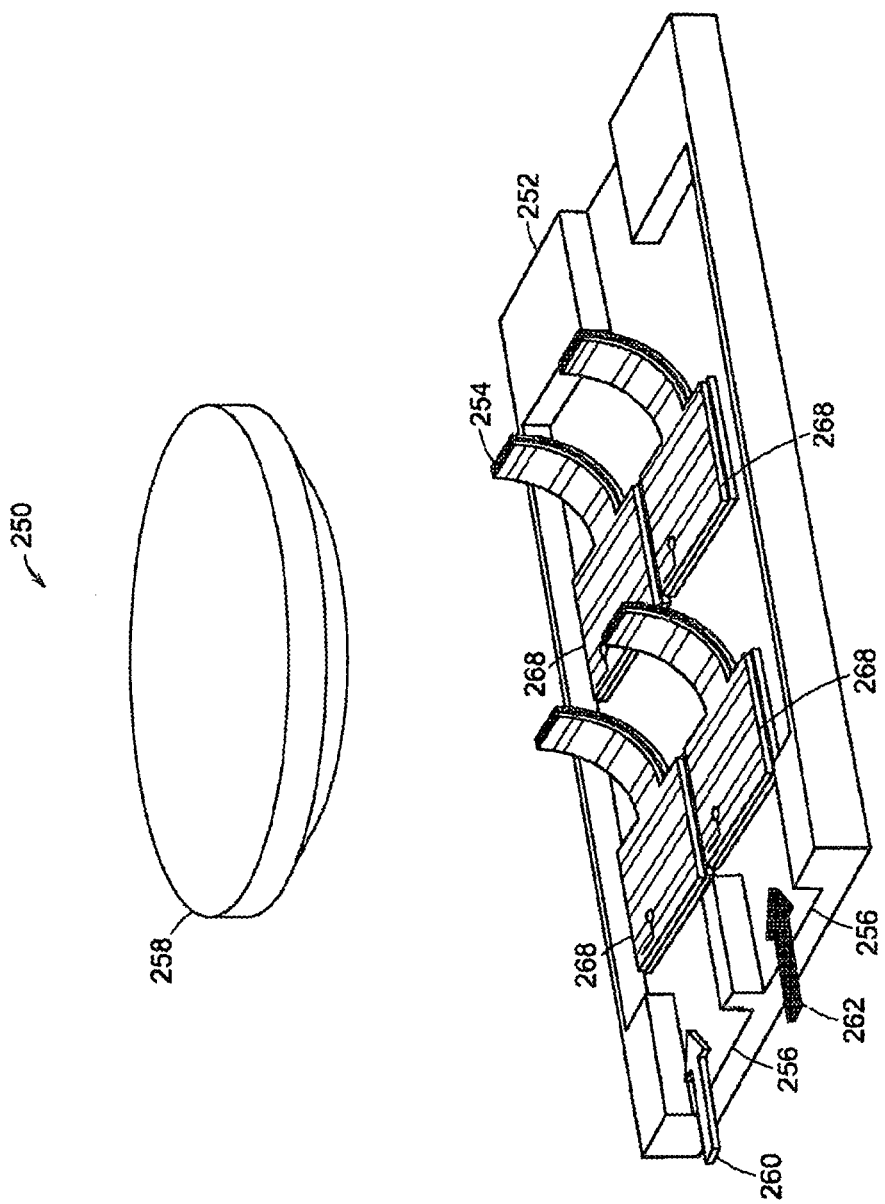
FIG. 18 illustrates an exemplary contractile function measuring system of FIG. 13 with extracellular and/or intracellular electrodes.

In some embodiments, as shown in FIG. 18, the system 250 can utilize optical and electrical measurement systems to measure the electrophysiological activities of the tissue to compensate the optical measurement system. In particular, the tissue structures 254 can include extracellular and/or intracellular electrodes 268 for recording reference filed potential signals. Optical methods to measure electrophysiological responses using photosensitive indicators may have issues in photobleaching, resulting in a difficult process to measure chronic response. However, optical methods generally provide better spatial resolution to measure electrophysiological responses than electrical methods. As such, one or more extracellular and/or intracellular electrodes 268 can be used as a reference to compensate the optical signal intensity for the photobleaching effect, allowing for an accurate measurement of the chronic response. In particular, electrical measurement signals generally have a constant magnitude, while optical measurement signals are easily bleached and, therefore, decreased. Thus, the magnitude of the electrical measurement signals can be measured first, and then the magnitude of the optical signals can be resealed to remove the photobleaching effect of the dye.

Figure 19:
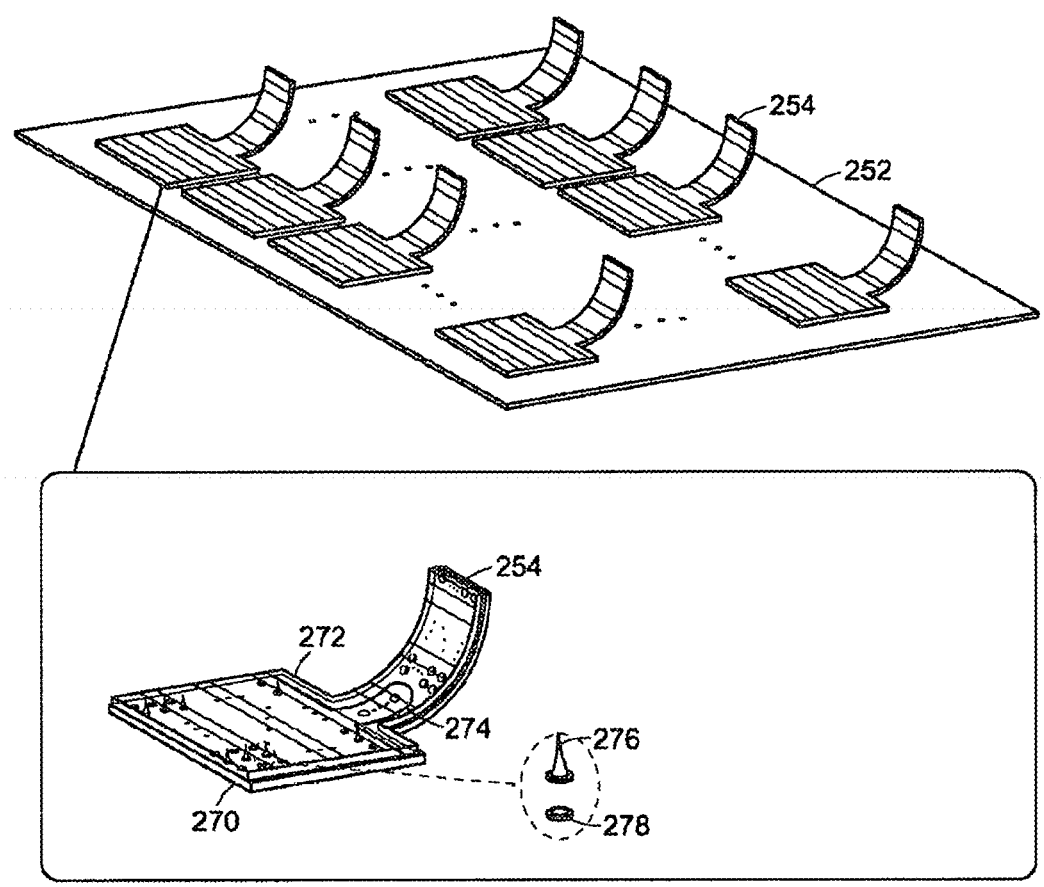
FIG. 19 illustrates an exemplary contractile function measuring system of FIG. 13 with extracellular and/or intracellular electrodes.

In some embodiments, as shown in FIG. 19, electrical methods can be used to measure both the electrophysiological and mechanical activities of the tissue. In particular, FIG. 19 shows tissue structures 254 that can be used with the system 250. The tissue structures 254 can include a polymer or hydrogel thin film 270 and tissue 272 (e.g., engineering muscle tissue, muscle complex, or the like) disposed on the thin film 270. The tissue structure 254 can include an electrical sensor 274 embedded therein to measure the deflection of the thin film 270. The tissue structure 254 can include one or more of the intracellular electrodes 276 and/or extracellular electrodes 278 for measuring the electrophysiological properties of the tissue 272.

In particular, the tissue structures 254 of FIG. 19 can be used to simultaneously measure contractility and action potential (or calcium handling) responses of the tissue structure 254. A noise cancellation circuit can be used to decouple the field potential (or action potential) signal from the contractility signal. For example, decoupling of the sampling bandwidth of signals or employing modulating/demodulating circuits can be used. Electrical methods of measurement allow for a high throughput screening and can include a high speed multi-channel analog-to-digital converter circuit.

The processor 112 associated with the systems discussed herein creates a feedback system. In particular, the processor 112 can process, calculate and transform the input signals into stimulation setups based on the output signals measured and received from both the mechanical and electrophysiological sensor systems. As an example, the systems can be used for arrhythmogenesis studies. The systems can be used to measure the action potential (or calcium) propagation pattern or speed, and contractility stress traces of the tissue structures. The systems can also be used to simultaneously calculate the magnitude and time of stimuli signals to generate heterogeneity in refractory periods of the tissue. The systems can further be used to stimulate tissue with the calculated stimuli to initiate or terminate reentrant arrhythmia.

Figure 67:
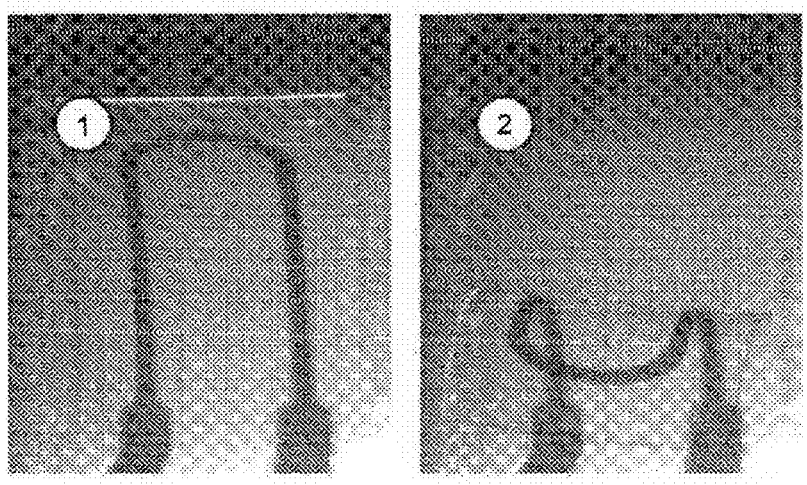
FIG. 67 illustrates an electrical sensor embedded in a tissue structure in accordance with embodiments of the present disclosure.
Figure 68:
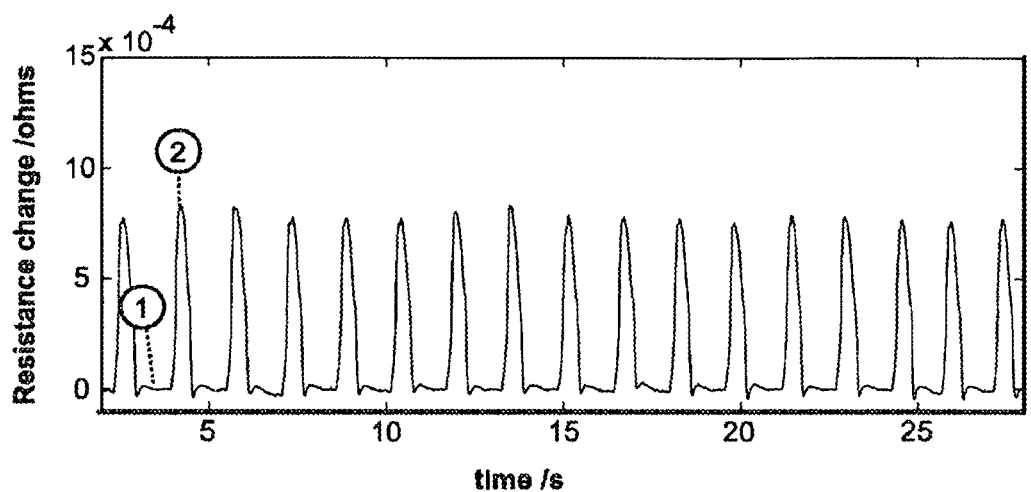
FIG. 68 illustrates a change in resistance measured from an electrical sensor embedded in a tissue structure in accordance with embodiments of the present disclosure.

As an example, FIGS. 67 and 68 show an electrical sensor (e.g., a gold strain gage in the form of a U-shaped electrical sensor) embedded in the tissue structure. The first position shown in FIG. 67 represents the tissue structure at a diastolic stress, and the second position shown in FIG. 68 represents the tissue structure at a systolic stress. FIG. 68 shows the change in resistance measured from the electrical sensor embedded in the tissue structure and corresponding to the first and second positions during deflection of the tissue structure. In particular, the resistance is at approximately 0 Ohms during the diastolic stress, and at approximately 7 to 8 Ohms during the deflection of the tissue structure at the systolic stress.

As a further example, the systems can be used to generate stem-cell derived muscle tissue maintaining similar (pathogenic) phenotypes and having batch-to-batch consistency and reproducibility. In particular, the systems can monitor stem-cell differentiation or maturation into muscle tissue in real-time by measuring the contractile force and the underlying intracellular calcium handling of the muscle tissue. The systems can also simultaneously calculate the magnitude and time of the desired stimuli (mechanical or electrical stimuli) using the measurement results. The systems can further stimulate the tissue with the calculated stimuli.

Figure 20:
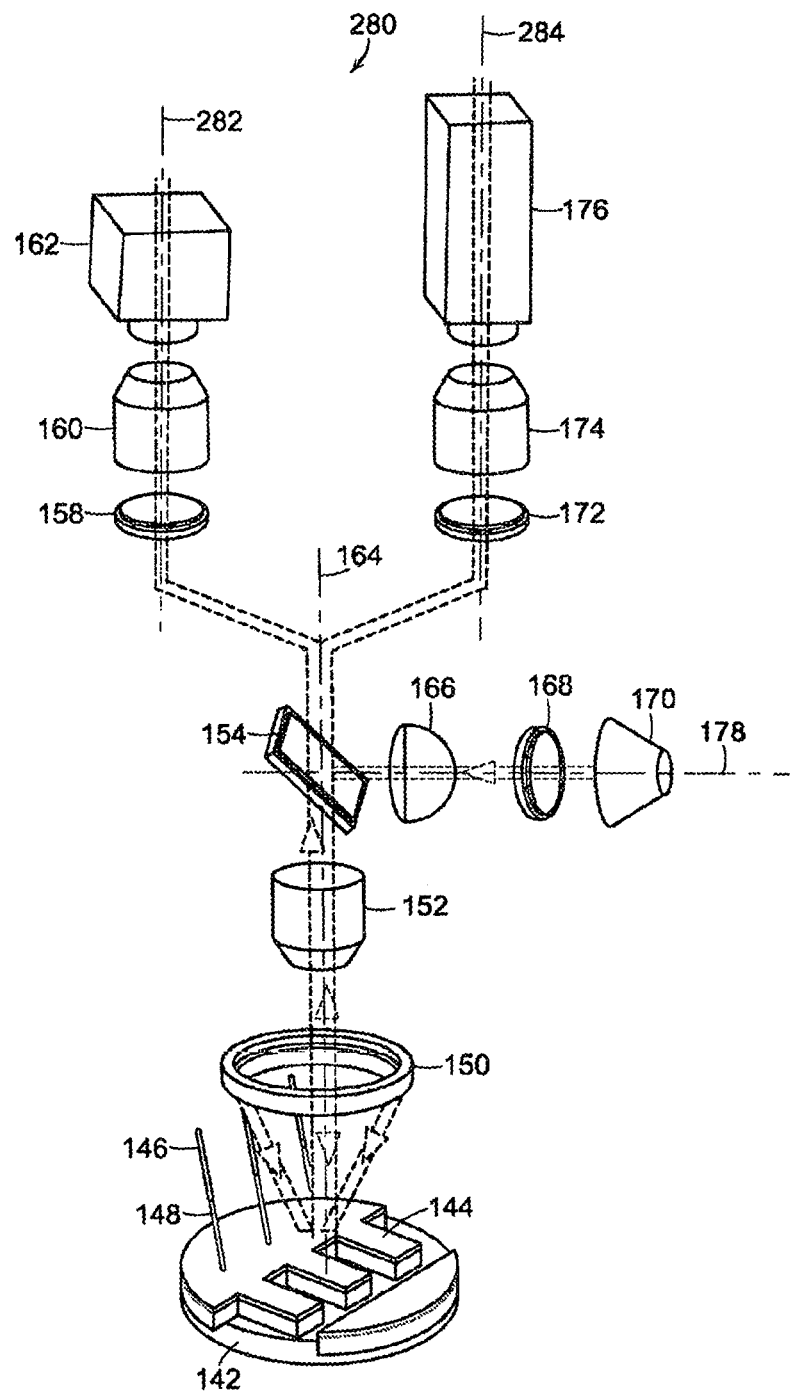
FIG. 20 illustrates an exemplary contractile function measuring system in accordance with embodiments of the present disclosure.

FIG. 20 is a setup of an exemplary contractile function measuring system 280 (hereinafter "system 280"). The system 280 can be substantially similar in structure and function to the system 140 of FIG. 4, except for the distinctions noted herein. Therefore, like reference numbers represent like structures. Rather than including two mirrors, the system 280 can include a single mirror 154 (e.g., a switching mirror). In particular, the system 280 can be a pseudo-simultaneous measurement system. The switching mirror 154 allows for selecting of the type of measurement being made by the system 280. For example, by switching the mirror 154, the contractility of the tissue structure 144 can be measured at one time, and switching the mirror 154 allows for measurement of the calcium or voltage signals the other time. In some embodiments, the system 280 can be programmed to switch the mirror 154 in a sequential manner such that after the contractility of the tissue structure 144 is measured, the mirror 154 can be automatically switched to measure the calcium or voltage signals, or vice versa. The components 150-154 can remain aligned along the vertical axis 164, and the components 166-170 can remain aligned along axis 178 perpendicular to the vertical axis 164.

However, the components 158-162 can be aligned along a vertical axis 282 parallel to the vertical axis 164. Similarly, the components 172-176 can be aligned along a vertical axis 284 parallel to the vertical axis 164. Thus, signals or light directed upward from the platform 142 can pass vertically through the respective filters 158, 172, lens 160, 174, and into the sensors 162, 176. Pseudo-simultaneous contractile and $Ca^{2+}$ handling properties can therefore be measured using dark field imaging (e.g., sensor 162) and calcium dye imaging (e.g., sensor 176). In particular, pseudo-simultaneous measurement of the mechanical and physiological properties of the tissue provides an improved understanding of the status of in vitro tissue (e.g., cardiac tissue). For example, the electro-mechanical window provides a biomarker for torsade de pointes risk, describing the time different between the end of repolarization and the end of ventricular contraction. However, it should be understood that the system 280 can be used for different types of tissues, such as muscle tissue, mobile tissue, and cells.

Figure 21:
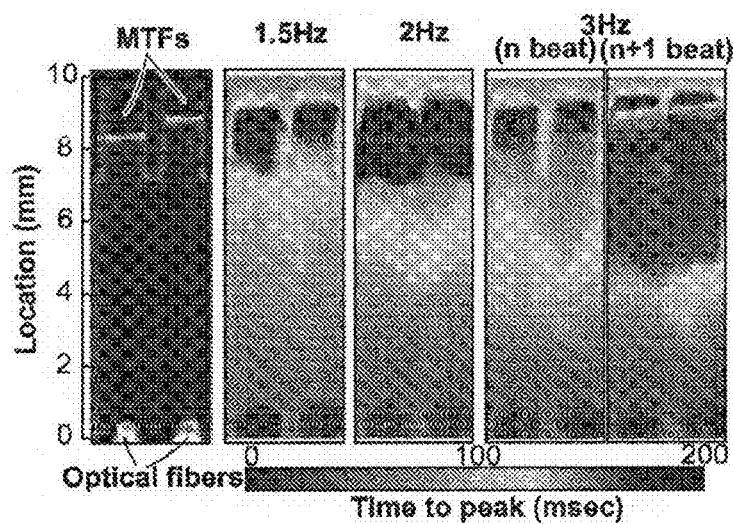
FIG. 21 illustrates an optogenetic tissue structure assay combined with optical mapping for an exemplary contractile function measuring system of FIG. 20.
Figure 22:
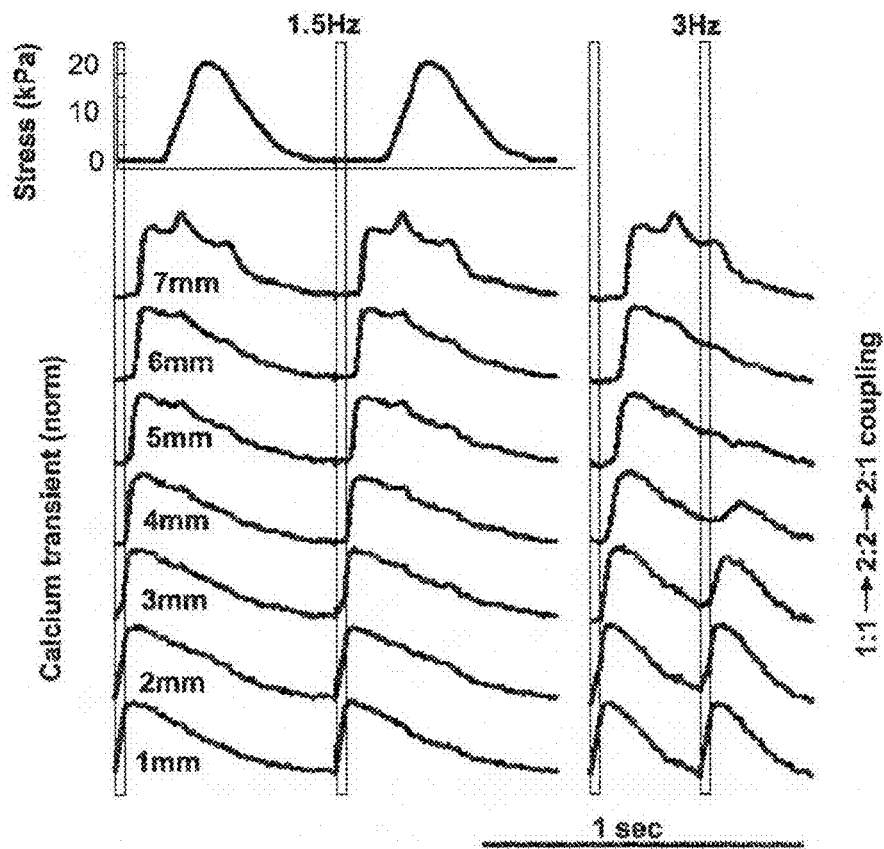
FIG. 22 illustrates contractility measurements and calcium transient imaging of optically stimulated tissue structures for an exemplary contractile function measuring system of FIG. 20.

During experimentation, excitation contraction coupling of the muscle thin films initiated by optical stimulation was demonstrated by observing the calcium wave propagation followed by contraction of the muscle thin films with an optical mapping system combined with dark field microscopy. With reference to FIGS. 21 and 22, the excitation contraction coupling of the muscle thin films initiated by optical stimulation and the calcium wave propagation followed by contraction of the thin film can be observed. FIGS. 21 and 22 show data acquired during testing with the system pseudo-simultaneous measurement system 280, which allows for measurement of intransient mechanical and electrophysiological properties of the tissue structure 144. In particular, the contractility measurements of the optically stimulated muscle thin films were performed by dark field imaging and the calcium transient imaging (e.g., Rhod-2). Trace of stress of the muscle thin films and the calcium transient is shown at various locations in FIG. 22.

Optical illumination can generate a local field (e.g., approximately a μm size) by using optical components such that each field does not interference with the other fields. Thus, as an example, cardiac tissues can be paced with multiple pacing frequencies on a single chip or platform. A small area of illumination can be sufficient to activate the overall cardiac tissue on muscle thin film. To utilize the advantage of optical stimulation, a multi-frequency optogenetic muscle thin film assay can be used that can be independently paced by optically stimulating a minimal area of tissue (e.g., less than approximately 1 mm² with less than approximately 500 cells).

Figure 23:
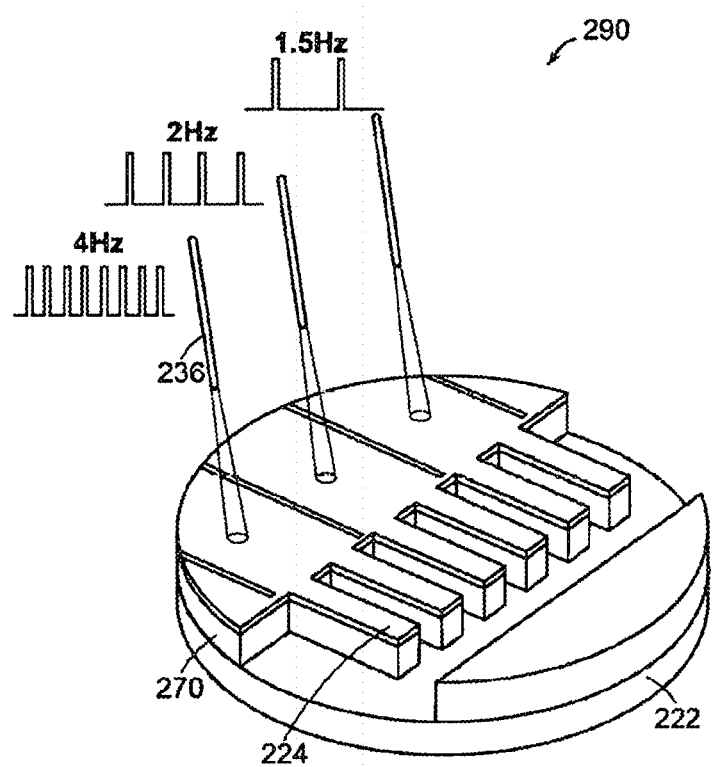
FIG. 23 illustrates an exemplary contractile function measuring system in accordance with embodiments of the present disclosure.

FIG. 23 shows a setup for an exemplary contractile function measuring system 290 (hereinafter "system 290"). The system 290 can be substantially similar in structure and function to the systems described above, except for the distinctions noted herein. Therefore, like reference numbers are used for like structures. The system 290 can be a combination of an optogenetic muscle thin film assay combined with an optical mapping system. The system 290 can include a plurality of light sources 236 in the form of approximately 488 nm LED lights guided by fiber optic cables. The light can be imparted on the muscle thin film, resulting in contraction or bending of the tissue. In particular, each muscle thin film can include an independent light source for actuation, thereby allowing for independent pacing of optogenetic muscle thin films at different frequencies. The channelrhodopsin (ChR2) expressing muscle thin films can be independently contracted at different optical pacing frequencies (e.g., 1.5 Hz, 2 Hz, 4 Hz, or the like) guided by the fiber optic cables.

For the system 290 of FIG. 23, optical fibers approximately 400 μm in diameter were used to generate illumination patterns between approximately 500-1,000 μm in diameter on light-sensitive ion channels expressing cardiac tissue monolayer (e.g., culturing cells in PDMS coated cover-glass substrates). Optically induced activation of local areas of the cardiac tissue was performed. The PDMS was cut into thin layers with a laser ablating system into 3 mm widths.

Cardiac cells were cultured on the PDMS layers. The cardiac tissues were physically disconnected and action potential could not come across the laser-ablating lines of the PDMS thin layer. The PDMS layers were divided into four pieces on the same glass. Cardiomyocytes were cultured on the four pieces of PDMS layers, and light sensitive ion channels were expressed on the cardiomyocytes using lentiviral gene delivery methods. All four cardiac tissues on the single glass slide were physically disconnected. Four light patterns between approximately 500-1,000 µm in diameter were illuminated on each of the four cardiac tissues, and the pacing frequency was independently controlled for each tissue.

Figures 24, 25:
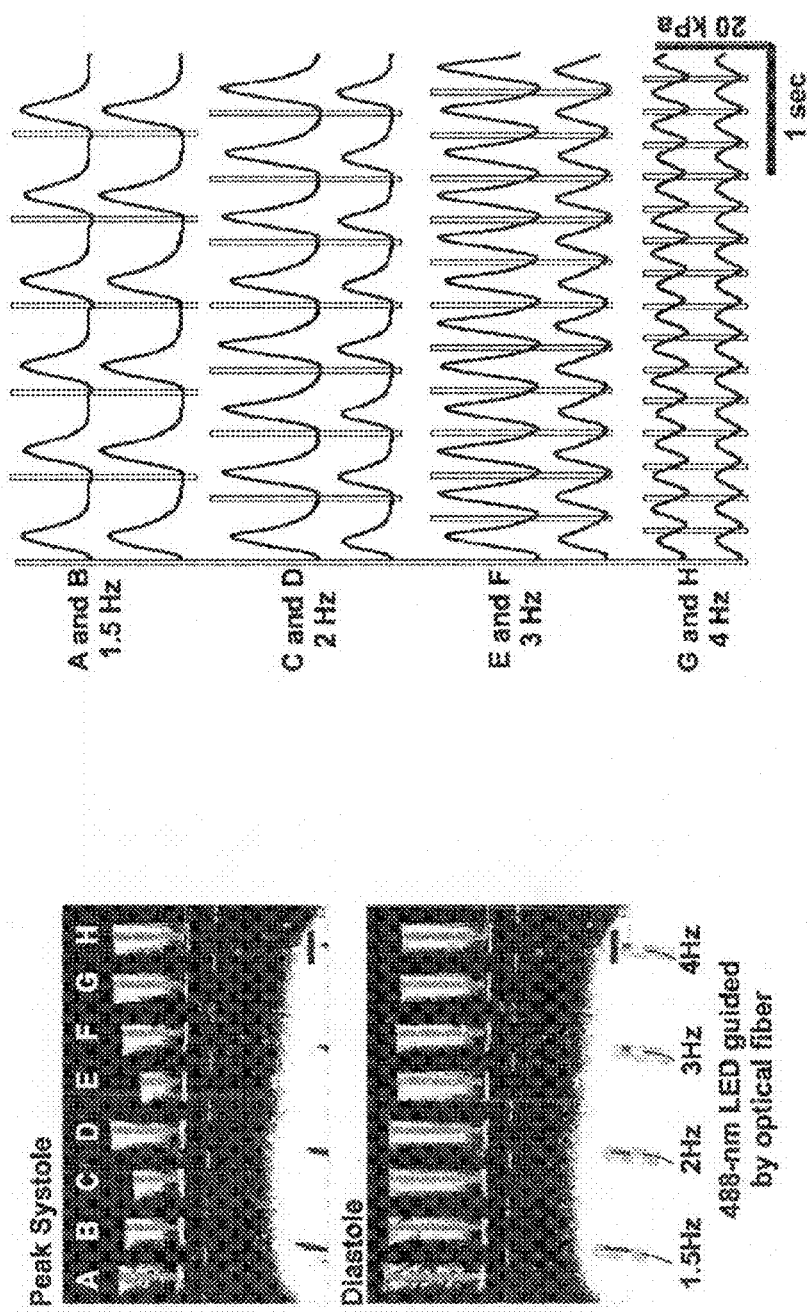
FIG. 24 illustrates peak systole and diastole contraction of a tissue structure of an exemplary contractile function measuring system of FIG. 23.
FIG. 25 illustrates stress traces of tissue structures of an exemplary contractile function measuring system of FIG. 23.

FIG. 24 shows the peak systole and diastole contraction of the tissue during testing at different pacing frequencies. FIG. 25 shows the stress traces of the individual tissue films independently paced at 1.5 Hz, 2 Hz, 3 Hz and 4 Hz. The stress traces of FIG. 25 were recorded simultaneously, while every two films were optically stimulated in a different frequency. Thus, the systems discussed herein can be used to localize stimulation and control each film individually. The frequency-dependent mechanical response data (e.g., 1:1 coupling, change in twitch stress, maximum rate of stress, dT/dt, or the like) show a tight confidence interval, indicating high uniformity and low variance of the multi-frequency muscle thin film assay.

Figure 26:
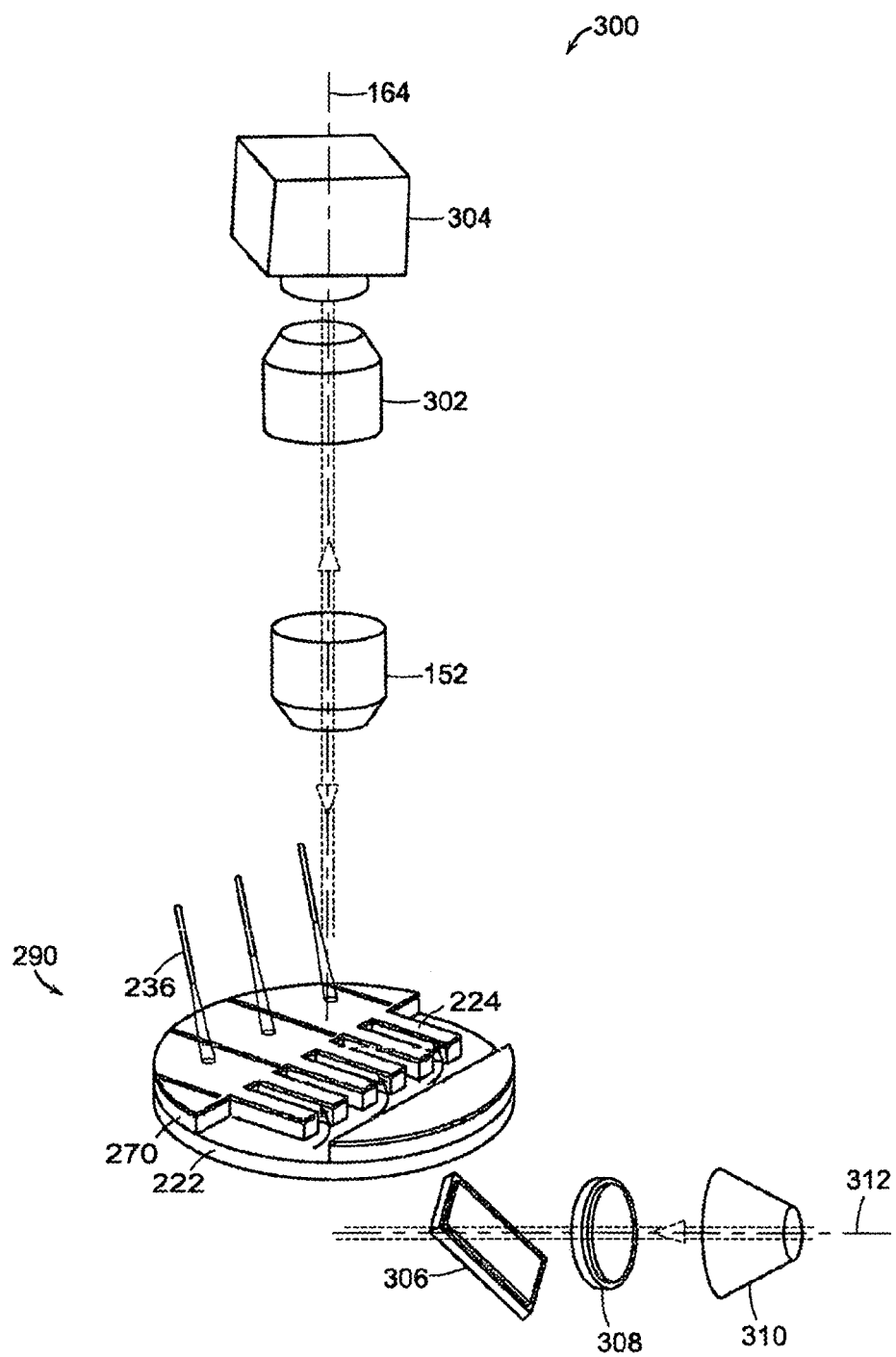
FIG. 26 illustrates an exemplary contractile function measuring system in accordance with embodiments of the present disclosure.

FIG. 26 shows an exemplary setup of a contractile function measuring system 300 (hereinafter "system 300"). The system 300 can incorporate the system 290. The system 300 can be substantially similar in structure and function to the systems discussed above, except for the distinctions noted herein. Therefore, like reference numbers represent like structures. The system 300 can include a lens 152 disposed above the platform 222 and a C-mount lens 302 (e.g., a 1× lens) disposed above the lens 152. The system 300 can further include a sensor 304 (e.g., a 100 frames per second complementary metal oxide semiconductor (CMOS) camera, or the like) disposed above the lens 302. The components 152, 302, 304 can be aligned along the vertical axis 164.

The system 300 can include mirror 306 (e.g., a mirror with an oblique angle), a filter 308 (e.g., an LP filter, such as 776LP), and a light source 310 aligned along an axis 312 substantially perpendicular to the vertical axis 164. Light imparted from the light source 310 can be directed by the mirror 306 at the tissue structures 224. The light can further be directed at the sensor 304. The system 300 provides a combination of an optogenetic tissue structure and an optical mapping system setup, including bright field microscopy for optogenetic tissue structures with the sensor 304 and red light illumination from the filter 308.

Figure 27:
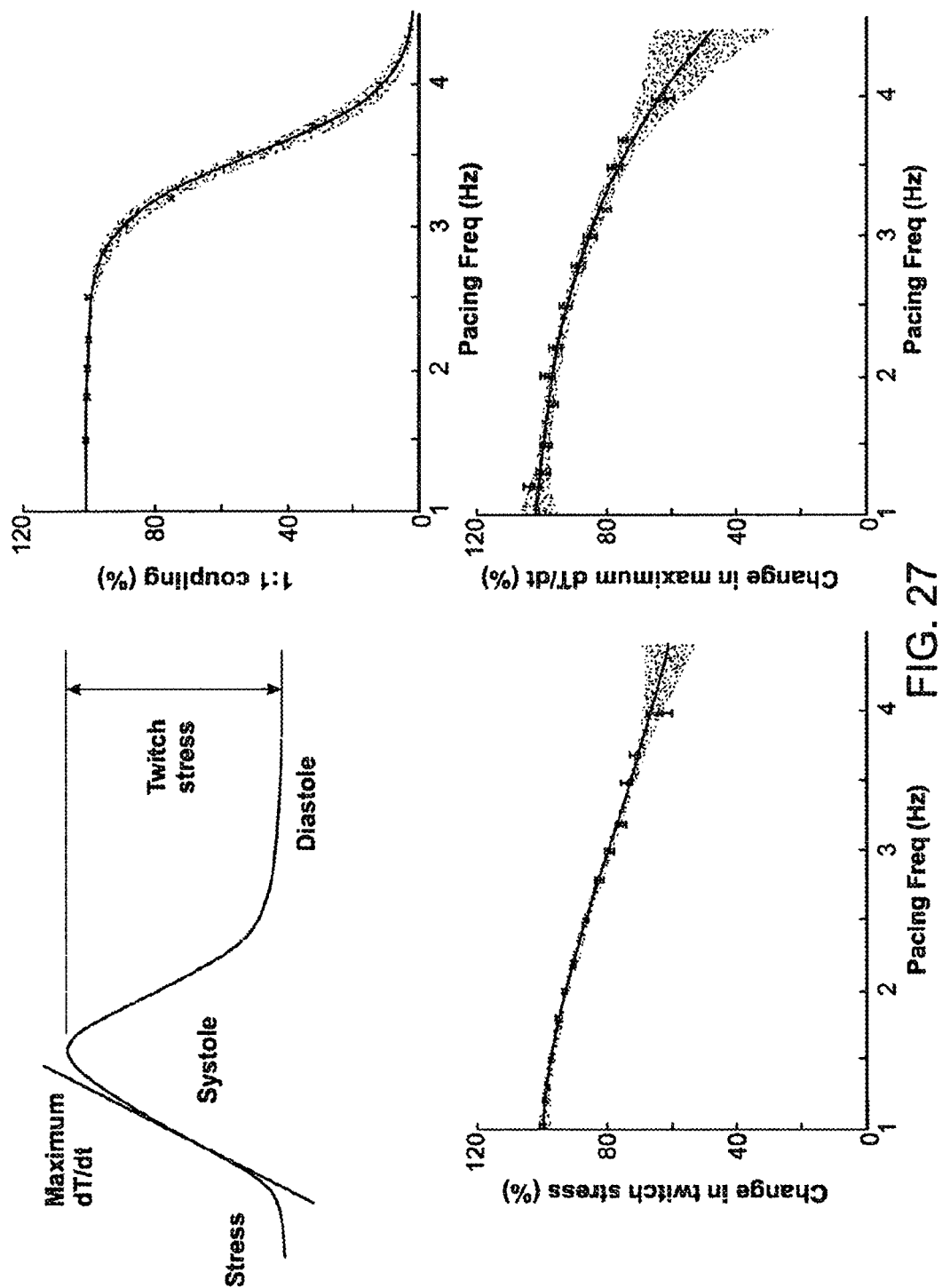
FIG. 27 illustrates frequency-dependent mechanical and calcium handling properties of a tissue structure in accordance with embodiments of the present disclosure.

FIG. 27 shows the frequency-dependent mechanical and calcium handling properties of tissue structures tested in the system 300. In particular, FIG. 27 shows the 1:1 coupling, change in twitch stress, and change in maximum dT/dt for the tissue structures at different frequencies. 124 muscle thin films were tested on 15 chips or platforms using three harvests. The error bar indicates a standard error of mean and the shading indicates approximately 95% confidence limits. The frequency-dependent mechanical response data shows a tight confidence interval, indicating uniformity and low variance of the muscle thin film assay. Thus, the independently paced optogenetic muscle thin films enable higher throughput assays to investigate the frequency-dependent response.

Figure 61:
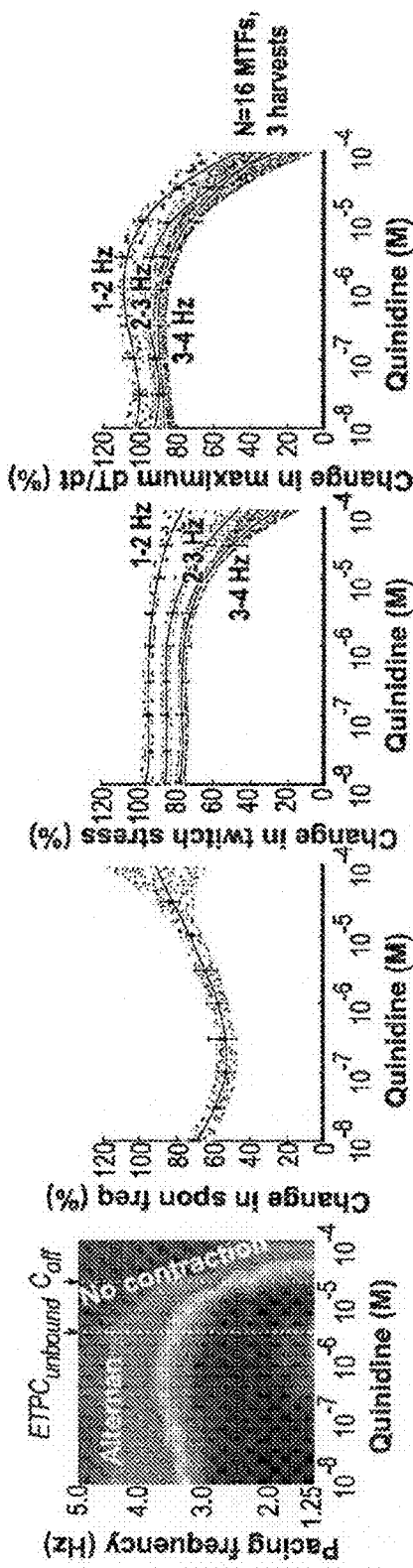
FIG. 61 illustrates frequency and dose-dependent response of cardiac tissue for quinidine testing in accordance with embodiments of the present disclosure.
Figure 62:
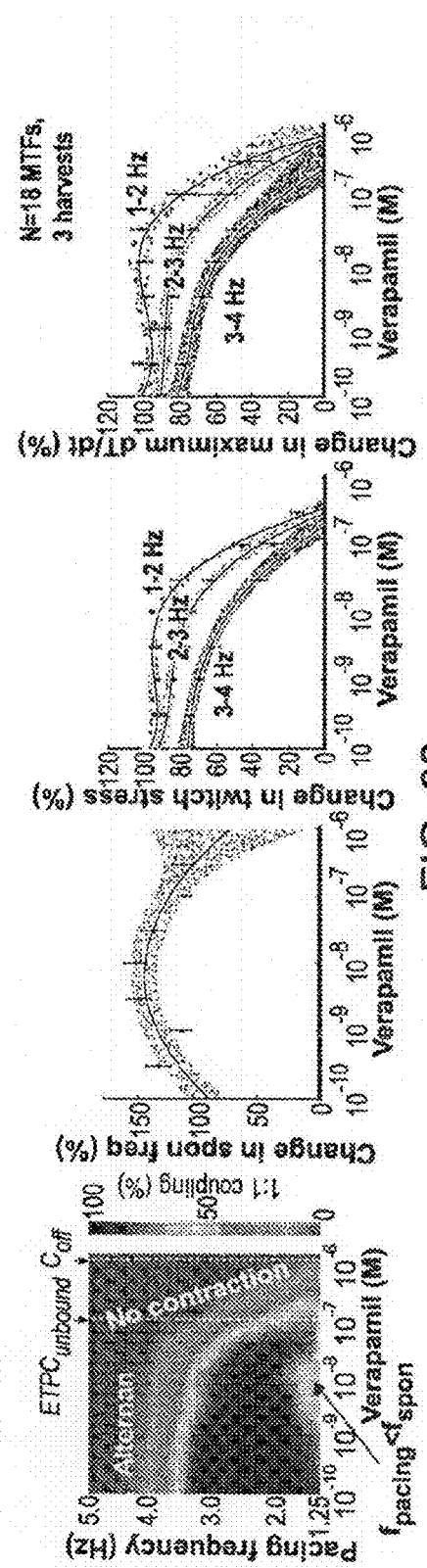
FIG. 62 illustrates frequency and dose-dependent response of cardiac tissue for verapamil testing in accordance with embodiments of the present disclosure.

As an example, quinidine and verapamil (both frequency-dependent) were tested for frequency and dose-dependent response in cardiac tissue. In particular, optogenetic muscle thin films in a contractile assay were used to recapitulate frequency and dose dependent mechanical responses of drug-treated tissue. The results are shown in FIGS. 61 and 62. In particular, FIGS. 61 and 62 show the pacing frequency, change in spontaneous beating rate frequency, change in twitch stress, and change in maximum Dt/dt for quinidine and verapamil. Verapamil treated tissue had a low 1:1 coupling at a low frequency with relatively low concentration due to the increase in the spontaneous beating rate caused by verapamil. It was determined that verapamil has a stronger negative inotropic effect than quinidine. Verapamil directly affects calcium handling, while quinidine does not directly affect myocardial contractility when given in therapeutic doses.

Figure 28:
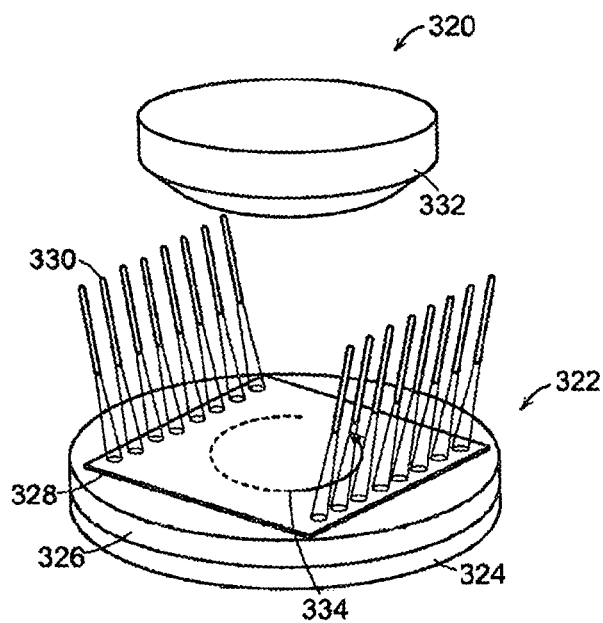
FIG. 28 illustrates an exemplary contractile function measuring system in accordance with embodiments of the present disclosure.
Figure 29:
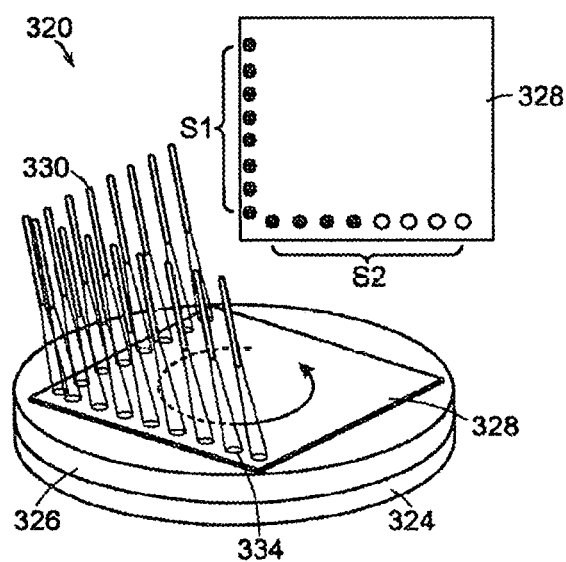
FIG. 29 illustrates an exemplary contractile function measuring system in accordance with embodiments of the present disclosure.
Figure 30:
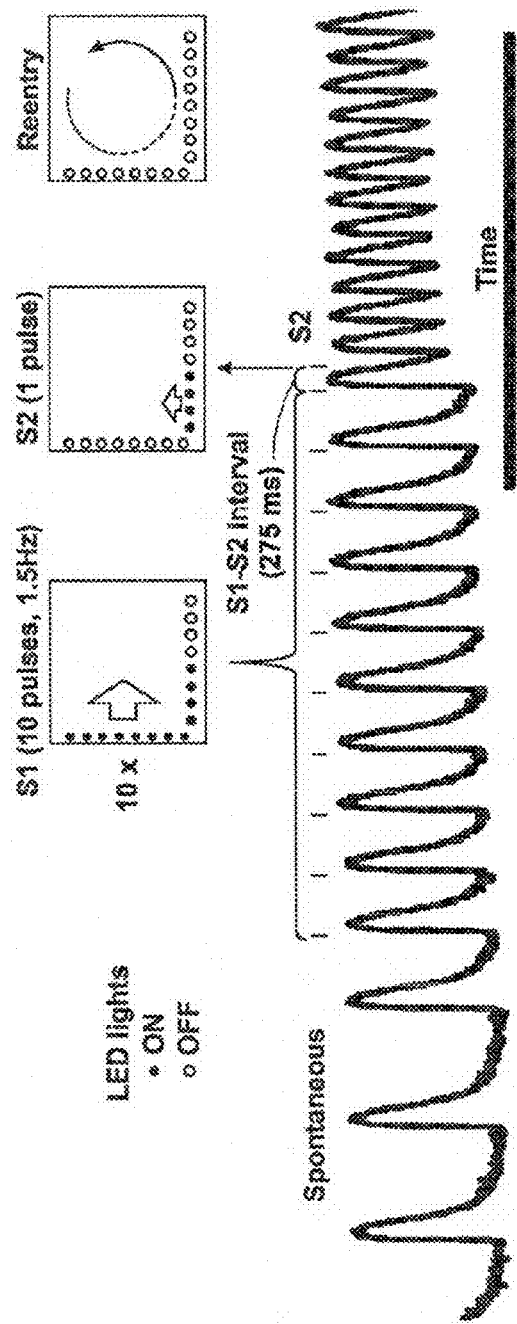
FIG. 30 illustrates spiral wave activity in a tissue structure in an exemplary contractile function measuring system of FIG. 29.

FIGS. 28 and 29 show a setup of an exemplary contractile function measuring system 320 (hereinafter "system 320"). The system 320 can include a platform 322. The platform 322 can include a glass coverslip 324 and an extracellular matrix coated polymer or hydrogel substrate 326 (e.g., a PDMS membrane) disposed on the coverslip 324. One or more tissue structures 328 (e.g., a ChR2-expressing cardiac tissue with light sensitive ion channels transfected) can be positioned on the platform 322. The system 320 includes light sources 330 mounted over the platform 322 and directing light onto the tissue structure 328. Although shown as disposed on two opposing sides of the tissue structure 328, it should be understood that the light sources 330 can be positioned on any side of the tissue structure 328 (see, e.g., FIG. 30). In some embodiments, the light sources 330 can be in the form of light illumination guided by optical fibers or micro-mirror arrays (e.g., 488 nm LED lights guided by fiber optic cables). Filled in circles (e.g., black) below the light sources 330 can represent an ON light source, and empty circles (e.g., white) below the light sources 330 can represent an OFF light source. The light sources 330 can be used to create a spatiotemporal illumination pattern on the tissue structure. The system 320 further includes a sensor system 332 that includes a lens and/or camera for sensing properties of the tissue structure 328 during calcium or action potential propagation 334.

As an example, the system 320 can be used to optically generate arrhythmia of in vitro engineered cardiac tissue. Testing arrhythmia with the system 320 allows an evaluation of antiarrhythmic and proarrhythmic responses to therapeutic agents. Reentry (e.g., reentrant arrhythmia) is the electrophysiologic mechanism responsible for the majority of clinically important arrhythmias. Reentrant arrhythmia can be caused by both anatomical and pathophysiological mechanism. Anatomical reentrant arrhythmia can be caused by asymmetric tissue damage and abnormal conducting structure, while pathophysiological mechanisms can include heterogeneities in resting potential, action potential amplitude, and refractoriness. (See, e.g., Katz, Arnold M., *Physiology of the Heart*, 5$^{th}$ Ed., Lippincott Williams & Wilkins, Wolters Kluwer Business (2011)).

Although reentry can be generated using electrical stimulation, optical stimulation can be more effective by allowing for generation of localized stimulation to activate the tissue. In particular, conventional electrical stimulation may have toxic effects (e.g., irreversible Faradaic reactions, toxic gas generation, acute stimulation), result in global tissue level stimulation, require tissue to be fully immersed in the chamber, is used for activation, and can result in high energy consumption. Optical stimulation is less toxic (e.g., low cell toxicity, chronic stimulation), allows for local stimulation (e.g., single cell level, subcellular level), does not require physical contact or immersion of the tissue, is multifunctional (e.g., activation, inactivation, testing of genetic mutations), and provides for lower energy consumption.

Reentry resulting from anatomical causes (e.g., conduction abnormality) can be mimicked by guiding action potential conduction in a unidirectional way by illuminating patterned light on the patterned light sensitive ion channel transfected tissue. If the pathway length (where action potential travel) of the desired device is equal to or larger than the refractory period time of the conduction velocity of the cardiac tissue, reentrant waves can be generated in the tissue. Reentry resulting from pathophysiological causes (e.g., heterogeneities in resting potential, action potential amplitude, refractoriness, or the like) can be mimicked by modifying the action potential of the light sensitive ion channel transfected tissue using optogenetics.

Three mechanisms can be used to terminate reentrant arrhythmias: slowed conduction, accelerated conduction, and a prolonged refractory period. (See, e.g., Katz, Arnold M., *Physiology of the Heart*, 5$^{th}$ Ed., Lippincott Williams & Wilkins, Wolters Kluwer Business (2011)). A slowed conduction mechanism can be used to terminate in vitro reentrant arrhythmias by activating the optogenetic inhibition channels (e.g., NpHR, Arch, ArchT, Mac, Champ, or the like). An accelerated conduction mechanism can be used to terminate in vitro reentrant arrhythmias by activating the optical excitation channels (e.g., ChR2, C1V1, or the like).

Combining cardiac tissue engineering with optogenetics in the system 320 enables the mimicking of arrhythmogenesis and defibrillation in vitro (e.g., in a chip approximately tens of millimeters by millimeters). The system 320 allows for control of spatial and temporal action potential of engineered cardiac tissue by generating illumination patterns or by patterning light-sensitive ion channel transfected cells. The system 320 also allows for termination of arrhythmia of engineered cardiac tissue by activating light sensitive ion channels of patterned tissue with patterned light from an illumination system. The system 320 also allows for monitoring of arrhythmia by simultaneously measuring the electrophysiological and/or mechanical properties while activating the engineered tissue. The system 320 further allows for design of spatiotemporal illumination patterns using finite element models to generate or terminate the optogenetic arrhythmia in vitro. The in vitro system 320 can be used for screening anti-arrhythmia and pro-arrhythmia therapeutic agents, evaluating stem cells, designing and testing defibrillators, or the like.

The system 320 can include cardiac tissue (e.g., isotropic, anisotropic, patterned, or the like). The system 320 can include light sensitive ion channels (e.g., ChR2, NpHR, SSFO, C1V1, or the like). The system 320 can include an illumination system configured to generate patterned light (e.g., a digital mirror array, fiber optics array, LED array, or the like). The system 320 can include a monitoring system (e.g., electrocardiogram (EKG, ECG), MEA, optical mapping system with calcium or voltage sensitive dyes or transfected voltage or calcium sensitive proteins, a contractility assay (e.g., muscle thin film), or the like). The system 320 can include a finite element model that can be used to design the spatiotemporal illumination patterns for arrhythmogenesis and defibrillation in vitro.

Figure 31A:
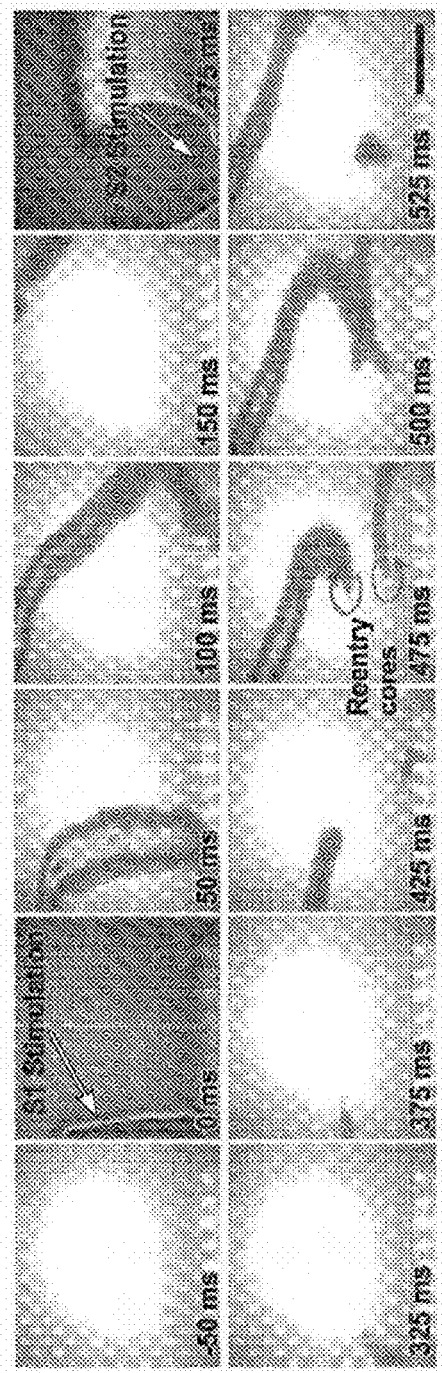
FIGS. 31A and B illustrate a derivative of calcium transient in an exemplary contractile function measuring system of FIG. 29.
Figure 31B:
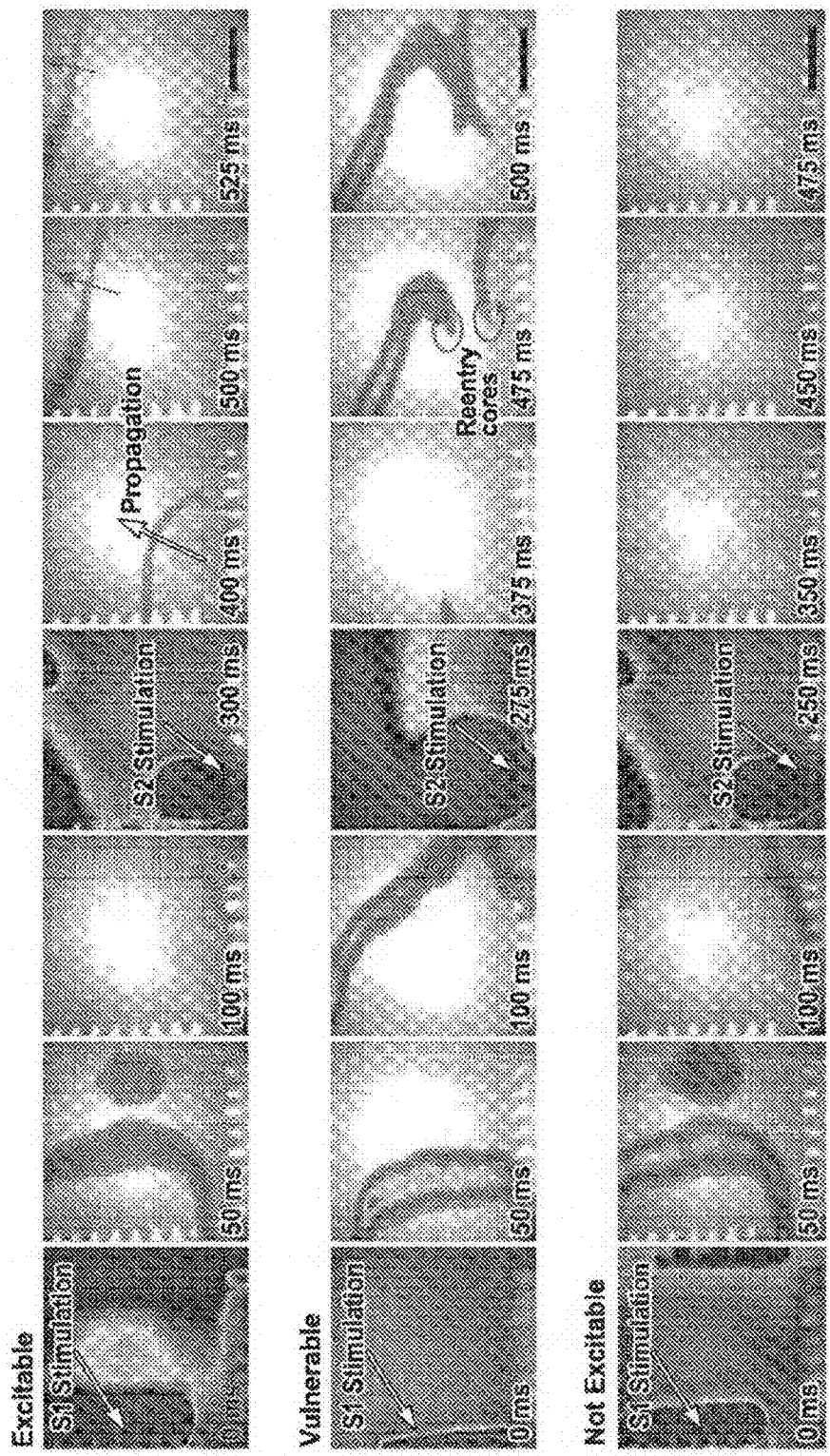
Figure 32:
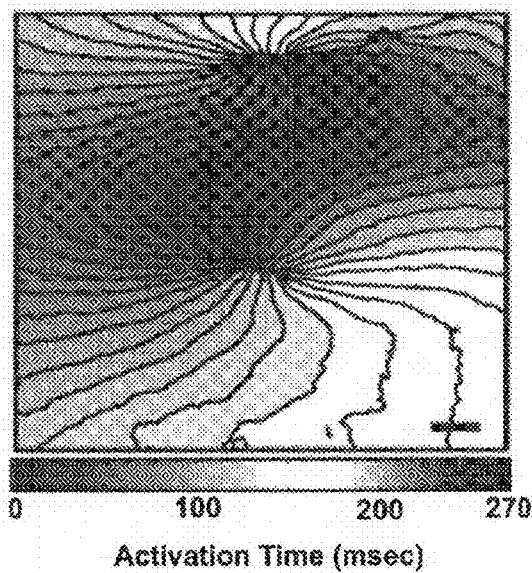
FIG. 32 illustrates an activation map for an exemplary contractile function measuring system of FIG. 29.
Figure 33:
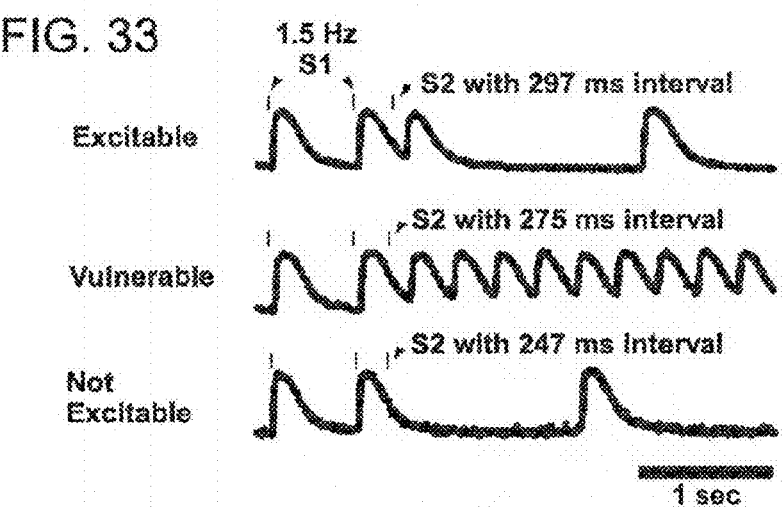
FIG. 33 illustrates cross-field stimulation for an exemplary contractile function measuring system of FIG. 29.
Figure 34:
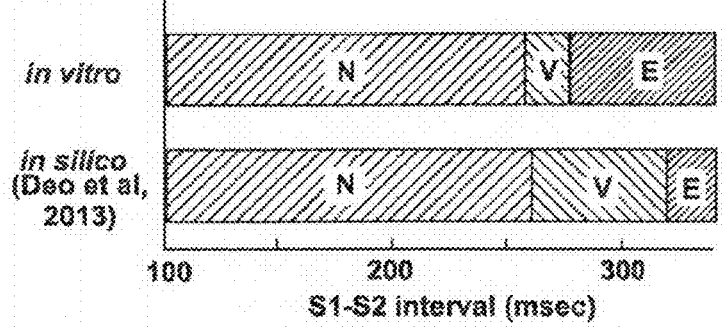
FIG. 34 illustrates cross-field stimulation for an exemplary contractile function measuring system of FIG. 29.

As an example, the system 320 was implemented to generate arrhythmia. Locally activated cardiac tissue stimulated by patterned light can activate tissue with different times and generates reentry of action potential. The results discussed below and shown in FIGS. 30-34 demonstrate that spatiotemporal illumination patterns can be used to initiate spiral wave activity in an anisotropic cardiac tissue. Optogenetic reentry on a chip for arrhythmia vulnerability measurement was created and a spatiotemporal illumination pattern induced reentrant arrhythmia of in vitro cardiac tissues by optically controlling the activation pattern of ChR2-transfected tissues. In particular, a cross-field stimulation protocol was implemented, including 10 pulses of 1.5 Hz S1 optical stimuli applied along the entire left edge of the tissue to induce calcium wave propagation from left to right, and an extra S2 optical stimulus was applied at the left lower corner (e.g., a portion of the bottom edge) of the tissue with varying S1-S2 stimulation intervals to induce a spiral wave (see, e.g., FIGS. 29 and 30). The cross-field S1-S2 stimulation protocols initiated spiral wave activity in the anisotropic cardiac tissue (approximately 1.6 cm by 1.6 cm in size) shown in the fluorescence intensity plot of Rhod-2 and the derivative of calcium transient shown in FIG. 31A (scale bar of 1 cm), and the activation map of FIG. 32 (scale bar of 200 μm). The cross-field S1-S2 stimulation protocol was used to investigate the vulnerability to reentry at varying S1-S2 intervals, as shown in FIGS. 31B, 33 and 34. FIG. 31B also illustrates a spiral wave pattern including multiple rotating waves. The vulnerability window can be affected by mixed ion channel activities, conduction velocity, and instability of conduction velocity and repolarization.

In particular, the intracellular calcium imaging with optical mapping system showed unique properties of optogenetically generated reentry arrhythmia. First, two stable concomitant wavefronts circulated in opposite directions (clockwise and counterclockwise) around two phase singularities (fixed cores), and merged into a central common pathway. Next, two wavefronts circulated in an elliptical trajectory which was caused by anisotropic distribution of the electrical connections between the cells is shown in an perfused animal ventricular myocardium. Reentry vulnerability of the engineered cardiac tissue monolayer was investigated using a vulnerability-to-reentry grid (see, e.g., FIGS. 33 and 34). The vulnerability grid can be used for checking a pro-arrhythmic effect of therapeutic agents. At the long S1-S2 interval, an atypical beat (S2) generated calcium propagation from the bottom to the top because all cardiomyocytes were excitable (see, e.g., FIGS. 31B and 33, excitable), while at the short S1-S2 interval, the atypical beat (S2) did not generate any calcium propagation because all of the cells were not excitable (see, e.g., FIGS. 31B and 33, not excitable). In certain intervals, the extra beat (S2) initiated reentry because some of the cardiac cells were still in a repolarization phase (see, e.g., FIGS. 31B and 33, vulnerable). The vulnerable window may be affected by heterogeneity of repolarization, as well as abnormality of conduction velocity, which is directly associated with drug-induced tosade de pointes (TdP). The S1-S2 interval window that produced reentry of the in vitro model was similar with that of the in silico model.

It was determined that locally activated patterned cardiac tissue stimulated by nonpatterned or patterned light can generate reentry of action potential. It was also determined that locally activated cardiac tissue with patterned light can induce inhomogeneous resting potential, which activates surrounding tissue (e.g., early depolarization). In particular, partially elevated resting potential can be enough to activate the surrounding normal tissue, leading to generation of early depolarization. It was further determined that locally activated cardiac tissue can induce inhomogeneous repolarization, which can activate the surrounding tissue (e.g., early depolarization). In particular, the partially prolonged repolarization process, which can be activated by normal tissue, can lead to generation of early depolarization.

Figure 69:
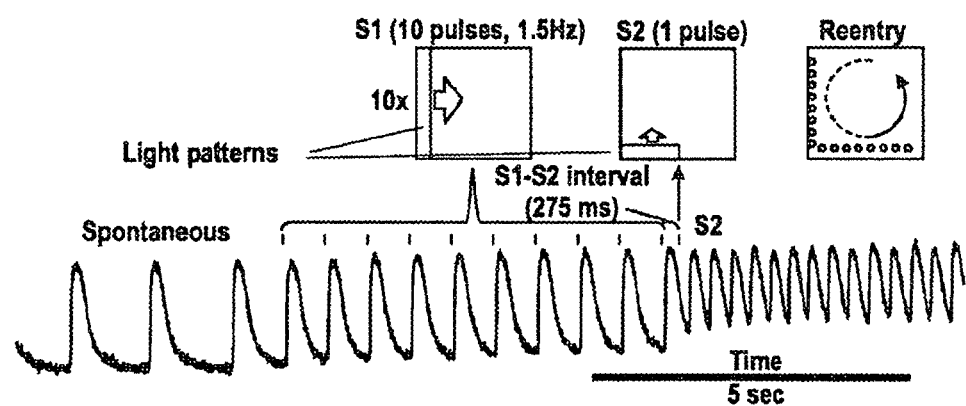
FIG. 69 illustrates an exemplary spatiotemporal illumination pattern in accordance with embodiments of the present disclosure.
Figure 70:
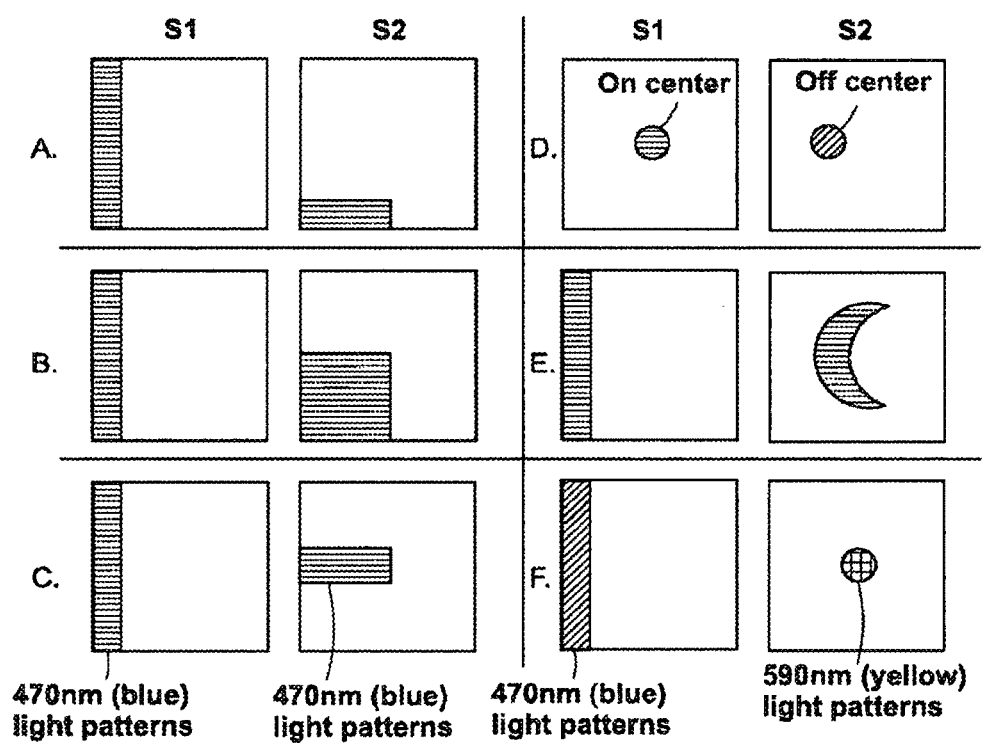
FIG. 70 illustrates exemplary spatiotemporal illumination patterns in accordance with embodiments of the present disclosure.

FIGS. 69 and 70 provide additional representations of spatiotemporal illumination patterns that can be generated by the light sources 330. In particular, multiple amounts of stimulation from the first stimulator (S1) can be set to desired action potential propagation, and further single or multiple amounts of stimulation from the second stimulator (S2) can be set to generate ectopic beating of tissue with the S1-S2 time interval. The illumination patterns can be generated by approximately 470 nm blue lights or approximately 590 nm yellow lights, or a combination of both 470 nm and 590 nm lights. The 470 nm blue light pattern can stimulate ChR2 to induce activation of the tissue, while the 590 nm yellow light can stimulate NpHR to induce hyperpoloarlization of the tissue.

FIG. 70 shows Examples A-F of spatiotemporal illumination patterns that can be generated. However, it should be understood that alternative patterns and/or a combination of patterns can be implemented. In Example A, S1 can generate illumination of a full row of the tissue structure and S2 can subsequently generate an illumination of a partial row of an adjacent edge of the tissue structure. In Example B, S1 can generate illumination of a full row of the tissue structure and S2 can subsequently generate an illumination of a square or rectangular group of rows and columns of an adjacent edge of the tissue structure. In Example C, S1 can generate an illumination of a full row of the tissue structure and S2 can subsequently generate an illumination of a partial row of a central portion of the tissue structure extending from the edge illuminated by S1. In Example D, S1 can generate illumination of an on-center point or spot centered on the tissue structure and S2 can subsequently generate illumination of a point or spot off-center on the tissue structure. In Example E, S1 can generate illumination of a full row of the tissue structure and S2 can subsequently generate a crescent-shaped illumination of a portion of the tissue structure. In Example F, S1 can generate illumination of a full row of the tissue structure with a 470 nm blue light and S2 can subsequently generate an on-center point or spot centered on the tissue structure with a different light type (e.g., 590 yellow light).

Figure 35:
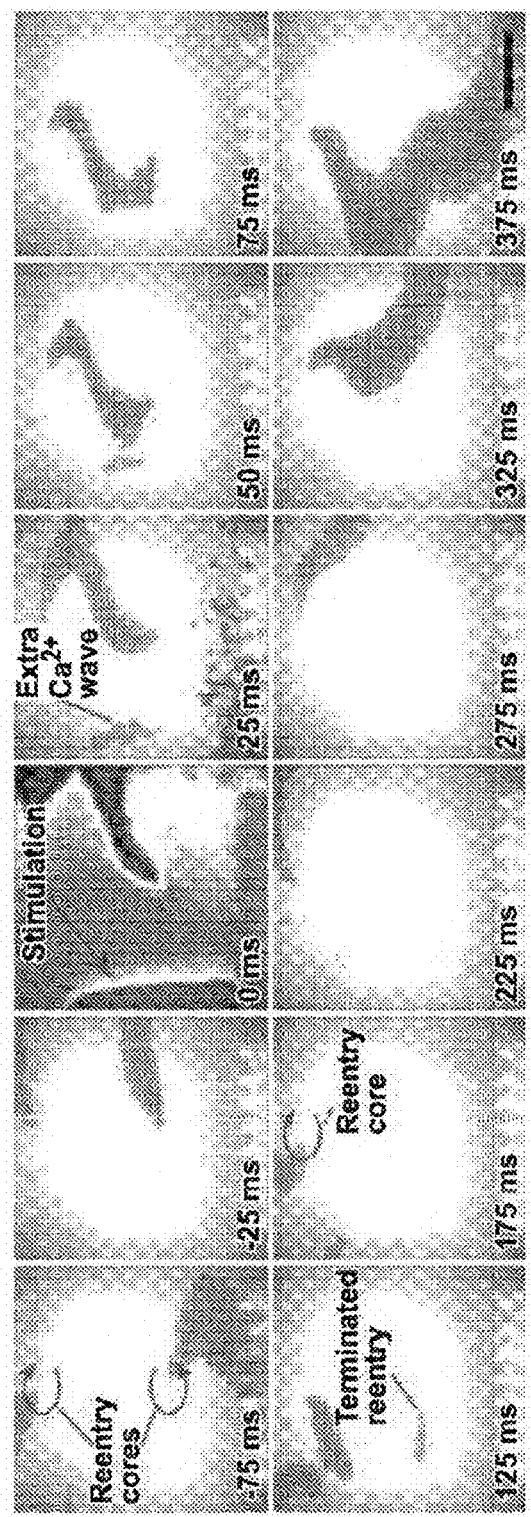
FIG. 35 illustrates optical excitation for an exemplary contractile function measuring system of FIG. 29.

Locally activated cardiac tissue stimulated by patterned light can activate tissue with different time and generates reentry of action potential. With respect to FIG. 35, termination of a reentrant arrhythmia circuit by using optical stimulation is shown. In particular, in vitro reentrant arrhythmia was terminated by activating an optical excitation ion channel (ChR2) as shown in the third frame from the left in the top row of FIG. 35.

Figure 63:
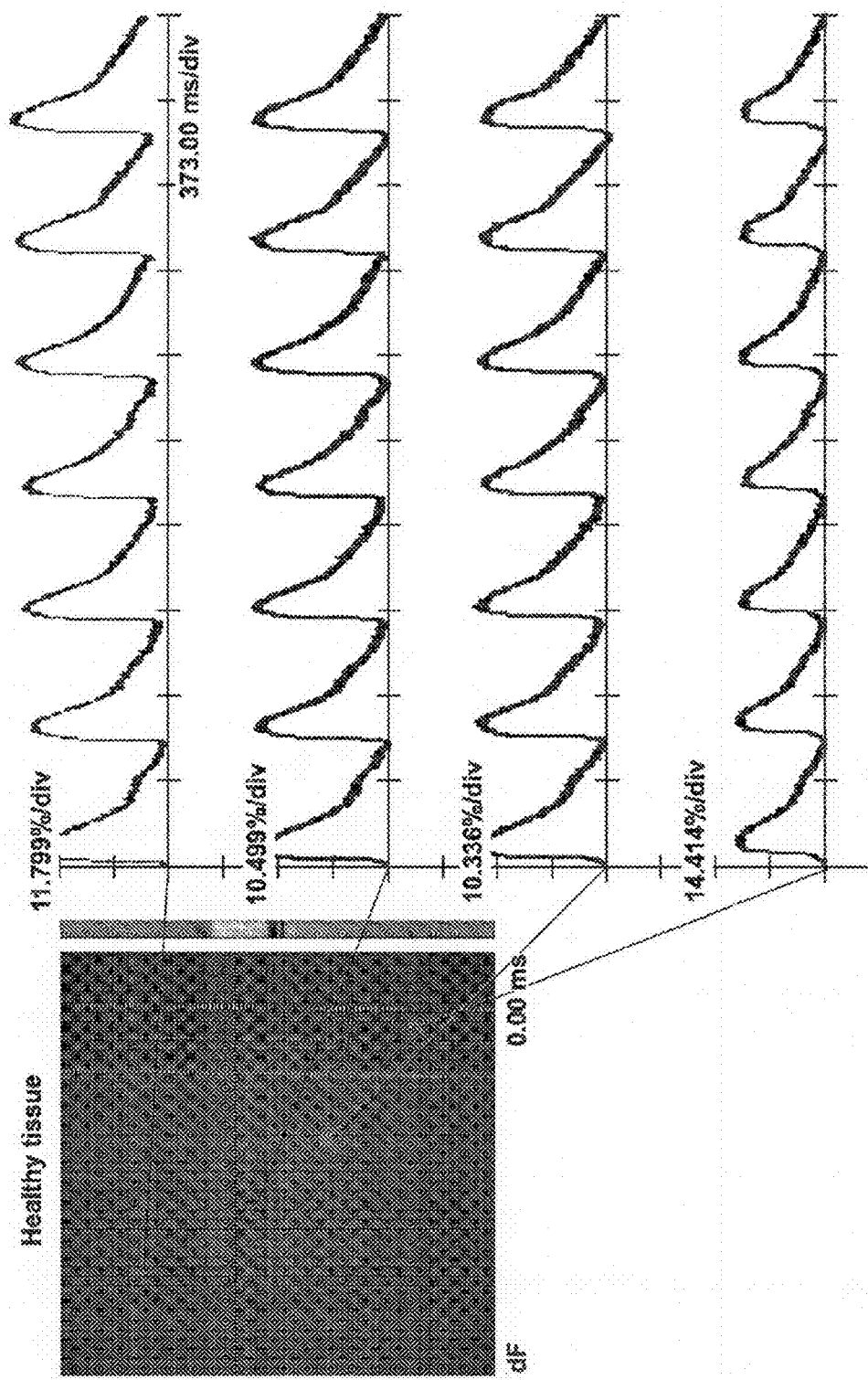
FIG. 63 illustrates calcium propagation across a healthy tissue in accordance with embodiments of the present disclosure.

FIG. 63 shows calcium propagation across healthy tissue as tested by the system 320. In particular, healthy tissue has a substantially uniform calcium propagation across the tissue. The experimental results show a calcium propagation speed of approximately 26 cm/sec.

Figure 36:
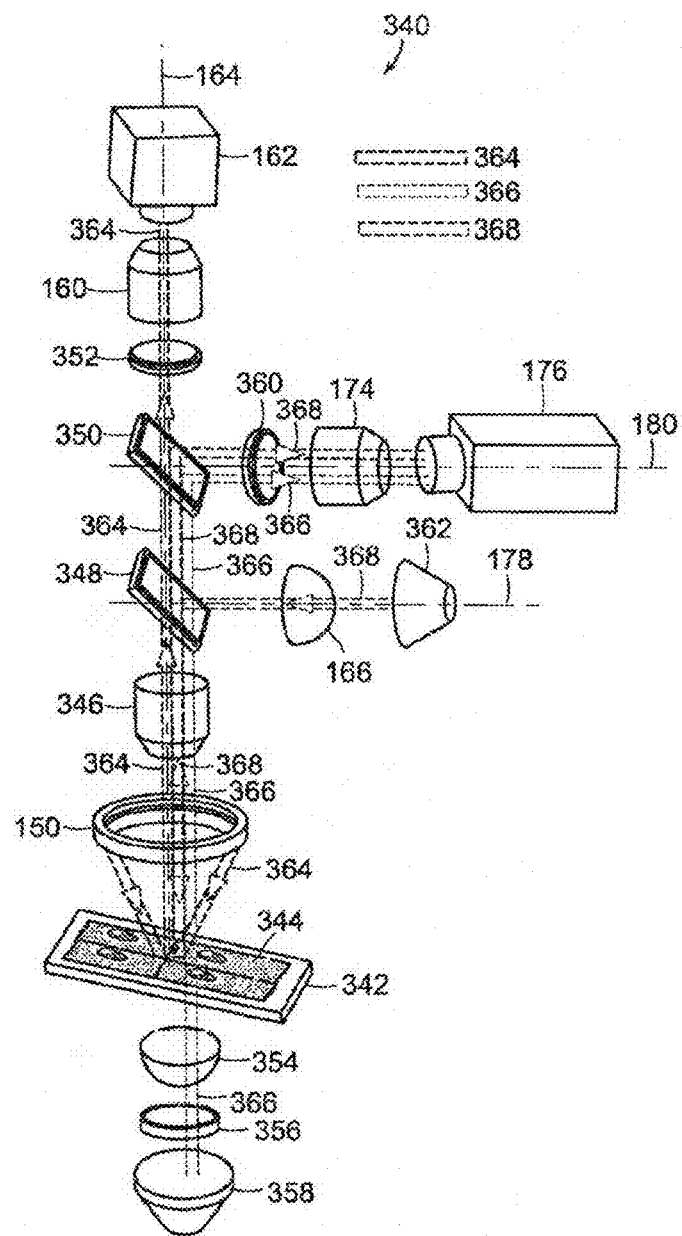
FIG. 36 illustrates an exemplary contractile function measuring system in accordance with embodiments of the present disclosure.

FIG. 36 shows an exemplary setup for a contractile function measuring system 340 (hereinafter "system 340") which can be used for monitoring arrhythmia. Locally activated cardiac tissue stimulated by patterned light can activate tissue with different time and generate reentry of action potential. The system 340 can be used to measure a chance in the calcium handling properties, membrane voltage, and contractility using calcium sensitive dye (e.g., Fura-2, xRhod-1, Rhod-2, or the like), a voltage sensitive dye (e.g., Rh-155, or the like), and ark field imaging (e.g., infrared light). The system 340 can be substantially similar in structure and function to the system 140 discussed with respect to FIG. 4, except for the distinctions noted herein. Therefore, like reference numbers represent like structures.

The system 340 includes a platform 342 with one or more tissue structures 344 positioned on the platform 342. The dark field LED ring light 150 can be disposed above the platform 342. The system 340 includes a plan apochromatic 1× or 0.5× lens 346 disposed above the right light 150. The system 340 includes a DC mirror 348 (e.g., 484) disposed above the lens 346. The system 340 includes a DC mirror 350 (e.g., $Ca^{2+}$: 593) disposed above the mirror 348. The system 340 includes a BP filter (e.g., 650LP) disposed above the mirror 350. The system 340 includes a collimator 354 disposed below the platform 342. The system 340 includes a BP filter 356 (e.g., V: 720/40) disposed below the collimator 354. The system 340 includes a lamp 358 (e.g., a mercury arc lamp) dispose below the filter 356. The components 342-358, 150, 160, 162 can be aligned along the vertical axis 164.

The system 340 includes a BP filter 360 (e.g., $Ca^{2+}$) disposed adjacent to the mirror 350. A lens 174 and a sensor 176 can be disposed adjacent to the filter 360. The components 360, 174, 176 can be aligned along the axis 180 substantially perpendicular to the vertical axis 164. The system 340 includes a collimator 166 dispose adjacent to the mirror 348 and a light source 362 (e.g., a rapid wavelength switching xenon light source, such as 340 nm or 380 nm) adjacent to the collimator 166. The components 166, 362 can be aligned along the axis 178 substantially perpendicular to the vertical axis 164 and parallel to the axis 180.

The beams 364 can be emitted from the right light 150 onto the tissue structure 344, and can be transmitted upward to the sensor 162 (e.g., dark field imaging for measuring the mechanical movement). The beams 366 can be emitted from the lamp 358, pass through the tissue structure 344, and is redirected by the mirror 350 to the sensor 176 (e.g., measurement of the Rh-155 voltage). The beams 368 can be emitted by the light source 362, redirected by the mirror 348 to the tissue structure 344, transmitted back to the mirror 350, and redirected to the sensor 176 (e.g., Fure-2 ratiometric calcium handling measurement). The system 340 can thereby be used to measure the electrophysiological (e.g., voltage and calcium handling properties) and mechanical properties (e.g., mechanical movement) of optically initiated reentrant arrhythmia. As stated above, it should be understood that the system 340 can be used to measure the electrophysiological and mechanical properties of a variety of tissue types.

Figure 37:
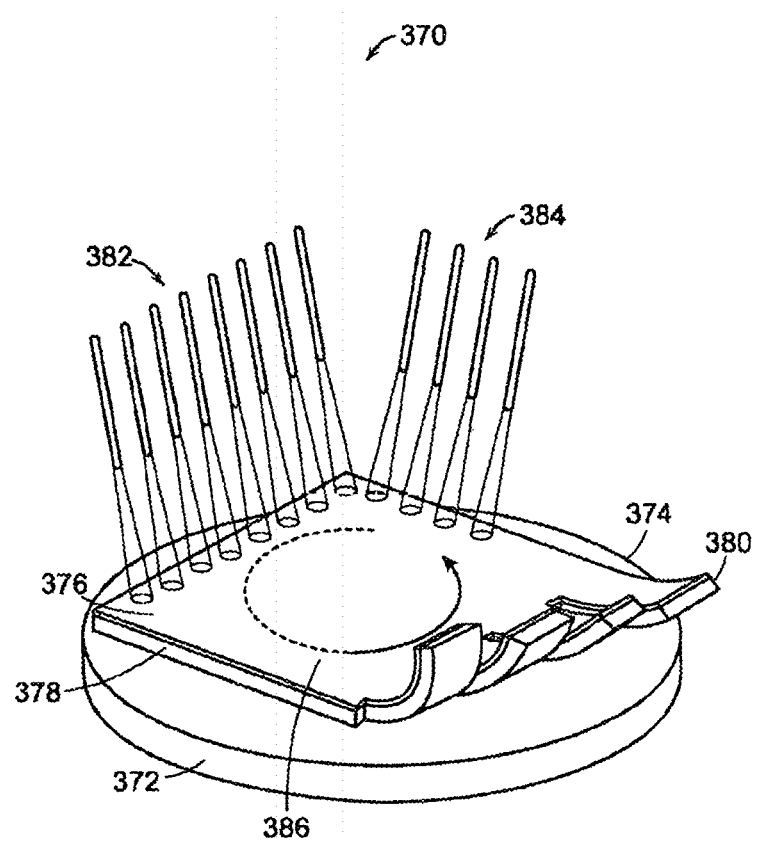
FIG. 37 illustrates an exemplary contractile function measuring system in accordance with embodiments of the present disclosure.

FIG. 37 shows a setup for an exemplary contractile function measuring system 370 (hereinafter "system 370"). The system 370 can include a platform 372 formed from, e.g., a rigid substrate, such as glass. The system 370 includes a tissue structure 374 positioned on the platform 372. The tissue structure 374 can include tissue 376 (e.g., cardiac tissue, or the like) positioned over a membrane 378 (e.g., a thin hydrogel or elastomer membrane). One side of the tissue structure 374 can include a plurality of cantilevered forms 380 extending from the tissue structure 374 that can be stimulated for contraction.

The system 370 further includes a plurality of light sources 382, 384 (e.g., 488 nm LED light guided by fiber optic cables) disposed around the platform 372 and configured to emit light onto the tissue structure 374. The light sources 382, 384 can be disposed on any sides of the tissue structure 374. For example, as shown in FIG. 37, one set of light sources 382 can be positioned along a first edge of the tissue structure 374, while the second set of light sources 384 can be positioned along a second and adjacent edge of the tissue structure 374. In some embodiments, the first set of light sources 382 can be used as a first stimulator (S1) and the second set of light sources 384 can be used as a second stimulator (S2), thereby allowing for creation of patterned pacing of the tissue 376. Stimulation of the tissue 376 results in calcium propagation 386.

As an example, the system 370 can be used to study cardiac arrhythmia and defibrillation. In particular, a spiral wave pattern of the cardiac tissue 376 can be initiated or terminated with a predetermined spatiotemporal pattern using the two stimulator arrays of light sources 382, 384. Simultaneous measurement and recording of the electrophysiological and mechanical properties of the tissue structure 374 enables monitoring of arrhythmia and defibrillation of engineered tissue in vitro.

Figure 38:
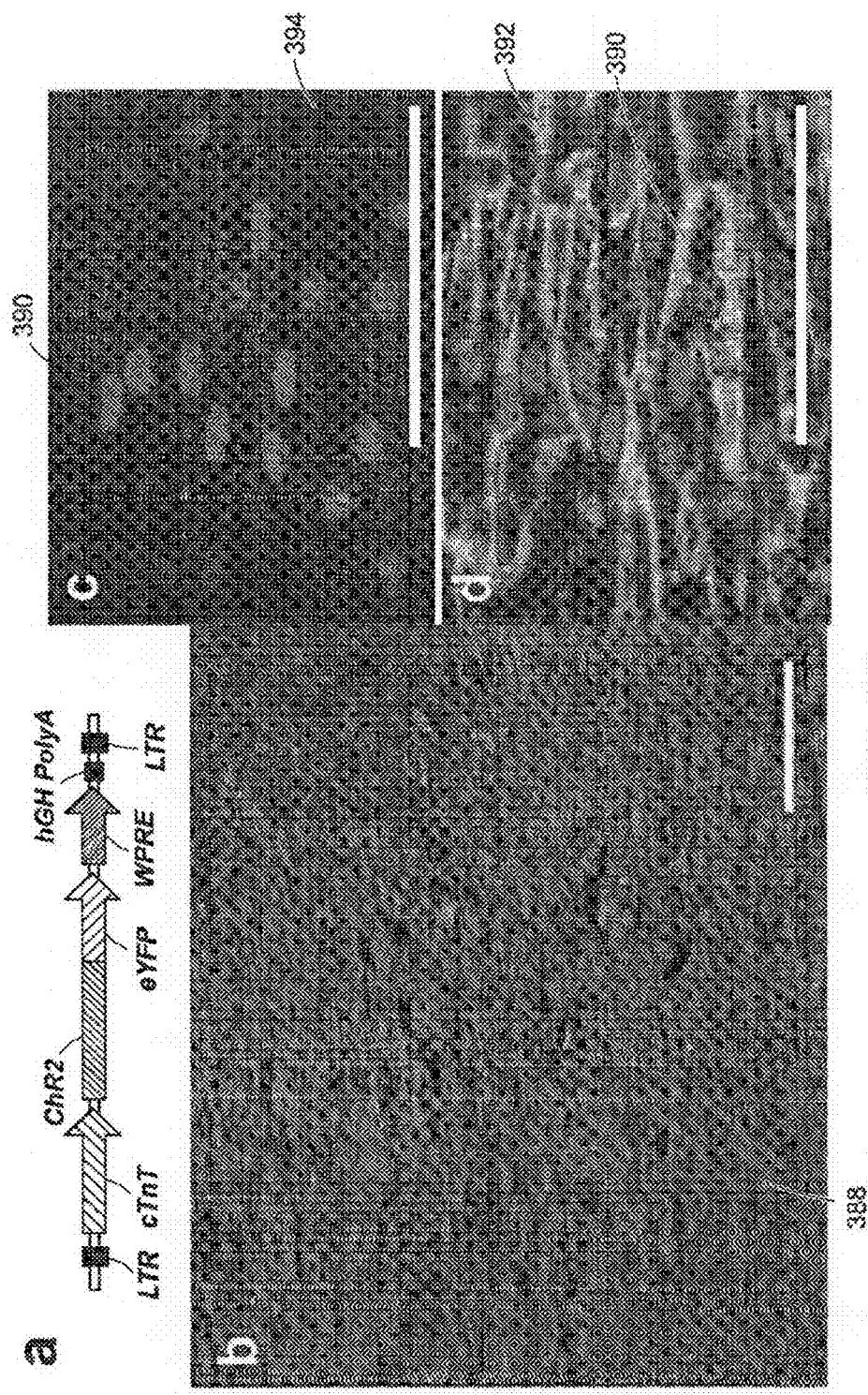
FIG. 38A-D illustrate a lentiviral vector, an engineered cardiac tissue expressing ChR2 uniformly, aligned engineered cardiac tissue in vitro, and staining for sarcomeric α-actinin with immunofluorescence of nuclei, ChR2-eYFP and sarcomeric α-actinin.

FIGS. 38A-D show anisotropic cardiac tissue expressing light sensitive ion channel (e.g., ChR2) on an elastomer substrate (e.g., PDMS). FIG. 38A shows a lentiviral vector for introducing ChR2 genes into the cardiac tissue. FIG. 38B shows the engineered cardiac tissue expressing ChR2 uniformly. Yellow fluorescent protein (eYFP) results in green staining 388 which indicates ChR2 expression. Lentiviral transfection was used to express light sensitive ion channels (ChR2 and NpHR), specifically in NRVM under the control of a cardiac troponin T promoter (cTnT) with greater than 70% efficiency at four days post-infection. FIGS. 38C and D show highly aligned engineered cardiac tissue in vitro and staining for sarcomeric α-actinin revealed uniaxial alignment of sarcomeres. The immunofluorescence of nuclei 390, ChR2-eTFP 392 and the sarcomeric α-actinin 394 are shown.

Figure 39:
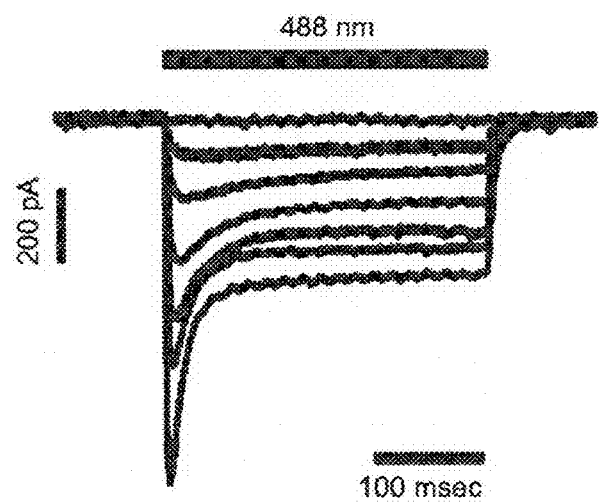
FIG. 39 illustrates a voltage-clamp recording for a tissue structure.
Figure 40:
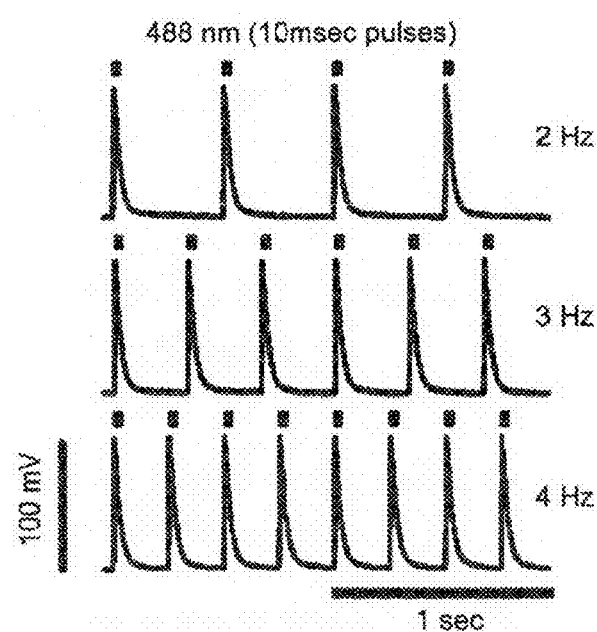
FIG. 40 illustrates a current-clamp recording for a tissue structure.

FIGS. 39 and 40 show that transducted light sensitive ion channels (e.g., ChR2 in cardiac cells) are functional at both the single cell and tissue levels. In particular, for the single cell level, FIGS. 39 and 40 show the voltage-clamp and the current-clamp recordings providing the ChR2 generated photo-sensitive current and ChR2 activation with light elicited action potentials at varying frequencies. For the tissue level, FIGS. 24 and 25 show results for ChR2-expressed muscular thin films that were optically paced using a blue light at varying frequencies.

Figure 41:
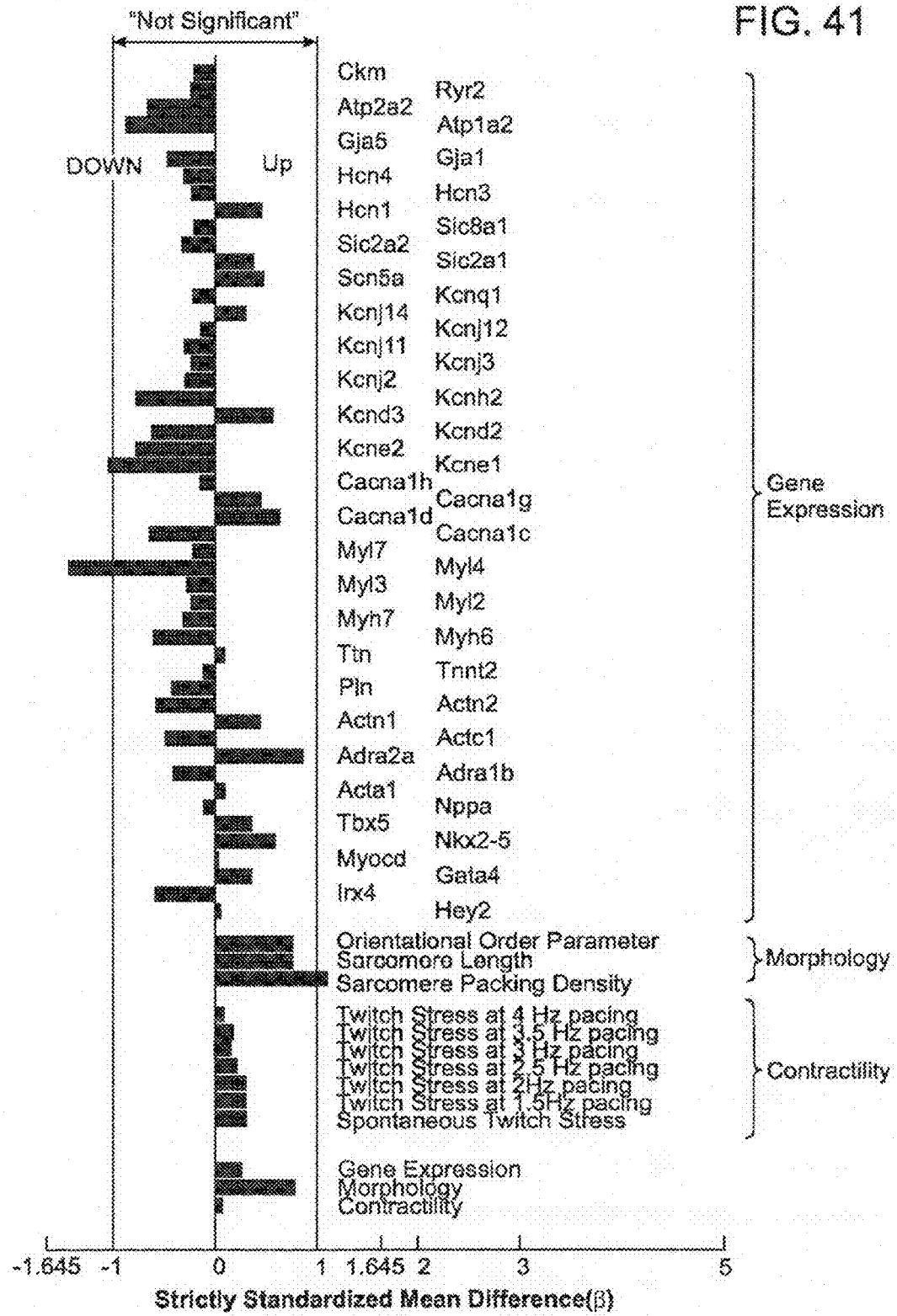
FIG. 41 illustrates a multiparametric quality assessment of ChR2-expressing cardiac tissue.

FIG. 41 shows the multiparametric quality assessment of ChR2-expressing cardiac tissue. The optically controllable cardiac tissue remained identical to naïve engineered tissue. A detailed comparison of gene expression (from qPCR), morphology (COBRA), calcium handling performance (OMS), and contractile performance (MTP) in ChR2 expressing NRVM tissue and naïve tissue using strictly standardized mean difference is provided in FIGS. 41 and 57-60. Based on the comparison, it was determined that the cardiac tissue expressing light sensitive ion channels are optically controllable, but otherwise identical to naïve engineered tissue.

Figure 43:
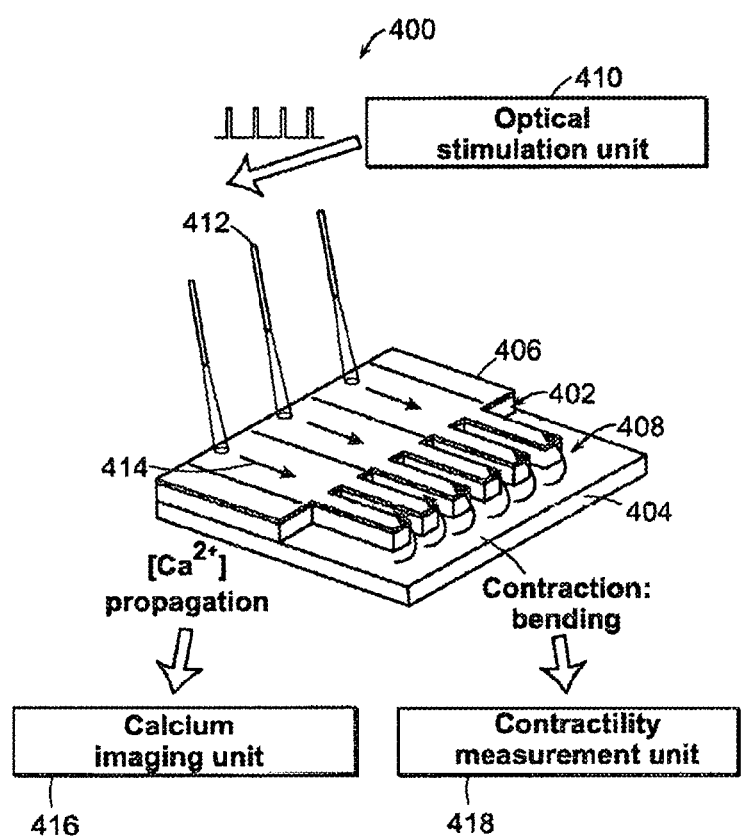
FIG. 43 illustrates an exemplary contractile function measuring system in accordance with embodiments of the present disclosure.

FIG. 43 shows a setup of an exemplary contractile function measuring system 400 (hereinafter "system 400"). The system 400 can be used in combination with, for example, system 140 shown in FIG. 4. The system 400 can include a tissue structure 402 (e.g., a muscle thin film) including a membrane 404 (e.g., PDMS, gelatin, or the like) with tissue 406 (e.g., anisotropic cardiac muscle tissue with ChR2 and calcium indicator, xRhod-1, or the like) disposed on the membrane 404. The tissue structure 402 can include cantilever portions 408 configured to allow for contractile bending during stimulation of the tissue 406. The system 400 includes an optical stimulation unit 410 including a plurality of light sources 412 (e.g., 488 nm light guided by fiber optic cables) configured to impart a light on the photosensitive portions of the tissue 406 to stimulate calcium propagation 414. The calcium propagation 414 can, in turn, actuate contractile bending of the tissue 406. A calcium imaging unit 416 (e.g., an electrophysiological sensor) and a contractility measurement unit 418 (e.g., a mechanical sensor) can simultaneously measure the electrophysiological and mechanical properties during contraction of the tissue 406.

Experimentation of the system 400 in combination with the system 140 was performed to obtain simultaneous calcium and mechanical signal recording. In particular, while optically stimulating the anisotropic engineered cardiac muscle expressing a light sensitive channel (ChR2), the system 400 was utilized to simultaneously measure the spatiotemporal calcium properties and contractility of the tissue 406. The tissue 406 was divided into 3 mm by 10 mm tissues containing two thin film cantilevers and individual light sources 412 for each thin film, such that each thin film could be independently contracted at different optical pacing frequencies.

Figure 44:
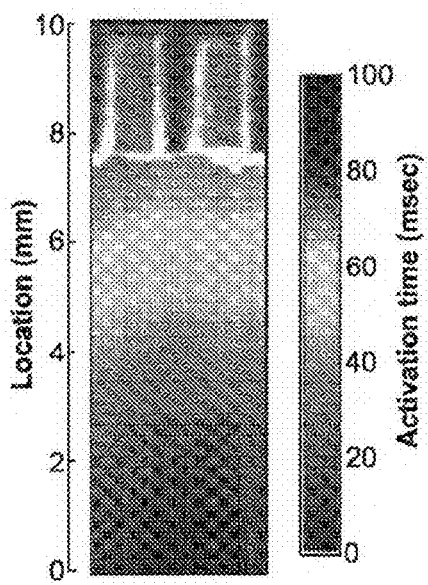
FIG. 44 illustrates activation mapping of a tissue structure tested by an exemplary contractile function measuring system of FIG. 43.
Figure 45:
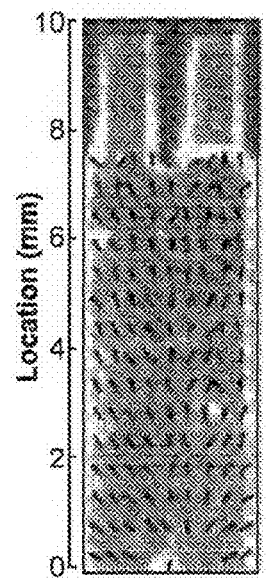
FIG. 45 illustrates vector field of propagation direction of a tissue structure tested by an exemplary contractile function measuring system of FIG. 43.
Figure 46:
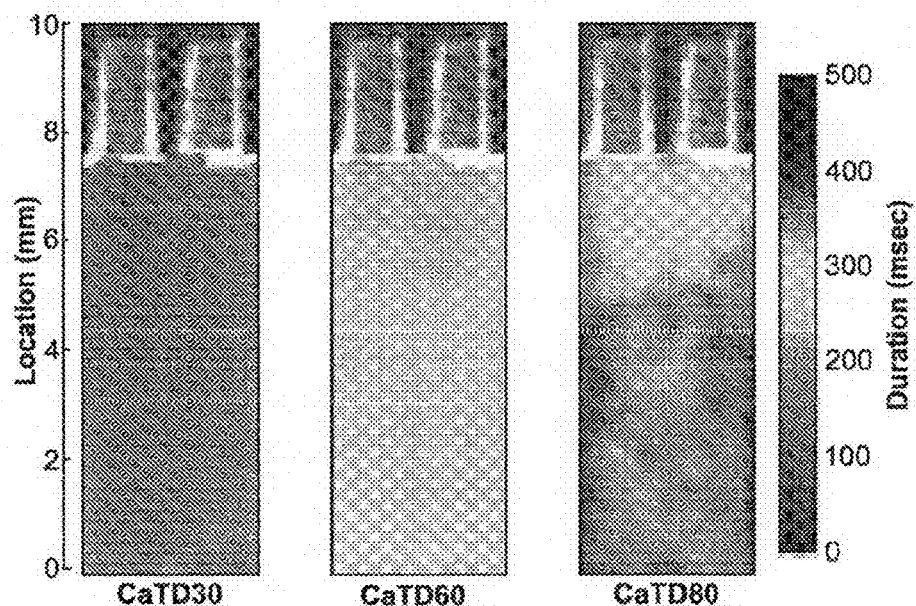
FIG. 46 illustrates calcium transient duration for a tissue structure tested by an exemplary contractile function measuring system of FIG. 43.

FIGS. 7, 8 and 44-46 show the results for this experimentation. In particular, FIG. 7 shows the stress and calcium traces with various locations (e.g., 1, 2, 3, 4, 5, 6 and 7 mm) from the excitation site. Time lapse images and stress and calcium traces show that optical stimulation initiated excitation contraction coupling of the muscle thin films. The calcium wave propagation was followed by contraction of the thin film. FIG. 8 shows time lapse images taken by simultaneous contractility measurements using dark field imaging (top) and calcium transient imaging with a calcium indicator (X-Rhod-1) (bottom) of the optically stimulated muscle thin film. FIG. 44 shows activation mapping and FIG. 45 shows vector field propagation direction during optical stimulation, showing that calcium propagates from the excitation cite to the muscle thin film. FIG. 46 shows a calcium transient duration 30 (left), 60 (middle) and 80 (right) representing heterogeneity of repolarization over the tissue 406.

Figure 47:
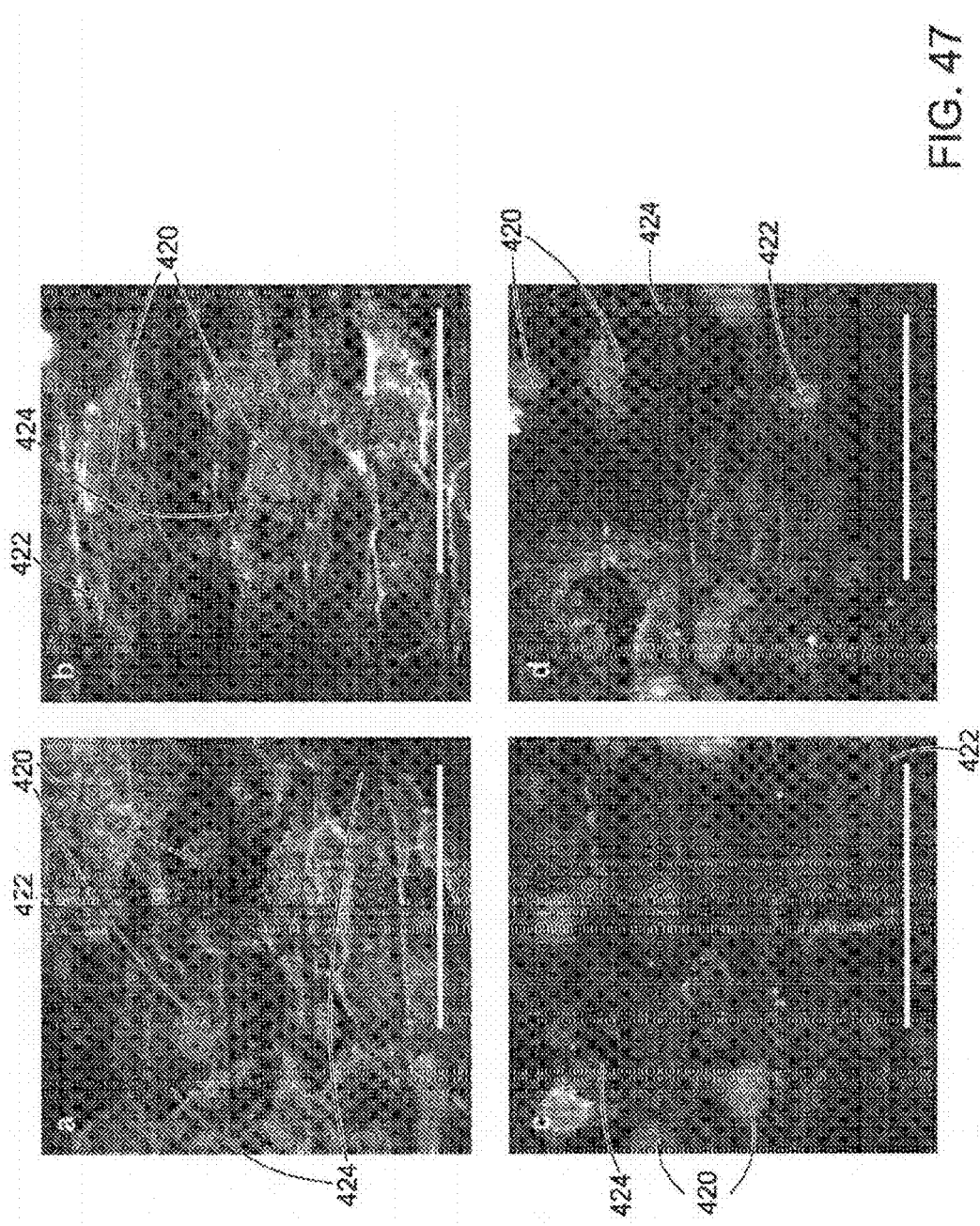
FIGS. 47A-D illustrate an extended culture of human induced pluripotent stem cells (iPSC) derived cardiomyocytes on micromolded gelatin substrates in accordance with embodiments of the present disclosure.

FIGS. 47A-D show extended culture of human induced pluripotent stem cells (iPSC) derived cardiomyocytes on micromolded gelatin substrates. In particular, FIG. 47A shows a wild-type hiPSC-derived cardiomyocytes from a commercial source (Axiogenesis, German), FIG. 47B shows a wild-type hiPSC-derived cardiomyocytes a Harvard research group (Dr. Pu, Boston Children's Hospital, Boston, Mass.), and FIGS. 47C and D show patient iPSC-derived cardiomyocytes with catecholaminergic polymorphic ventricular tachycardia (CPVT). iPSC was generated from patients with CPVT. Immunostainings revealed uniaxial alignment of sarcomeres and high expression of light sensitive ion channel ChR2. Immunofluorescence of nuclei 420, ChR2-eYFP 422, and sarcomeric α-actinin 424 are shown for immunostainings of human cells at a 100 μm scale bar.

Human induced pluripotent stem cell-derived cardiomyocytes (hiPSC-CMs) were used to check species-specific differences on drug responses. Anisotropic tissue structures of hiPSC-CM tissue were provided on micromolded gelatin substrates. Muscle thin films and optical mapping system data showed that hiPSC-CM tissue can be optically paced between 0.8 and 1.5 Hz, and further showed homogeneity in calcium propagation. Thus, the systems can be integrated with human cardiac tissues to provide a means for checking human-specific drug responses at an early stage of drug development.

Figure 48:
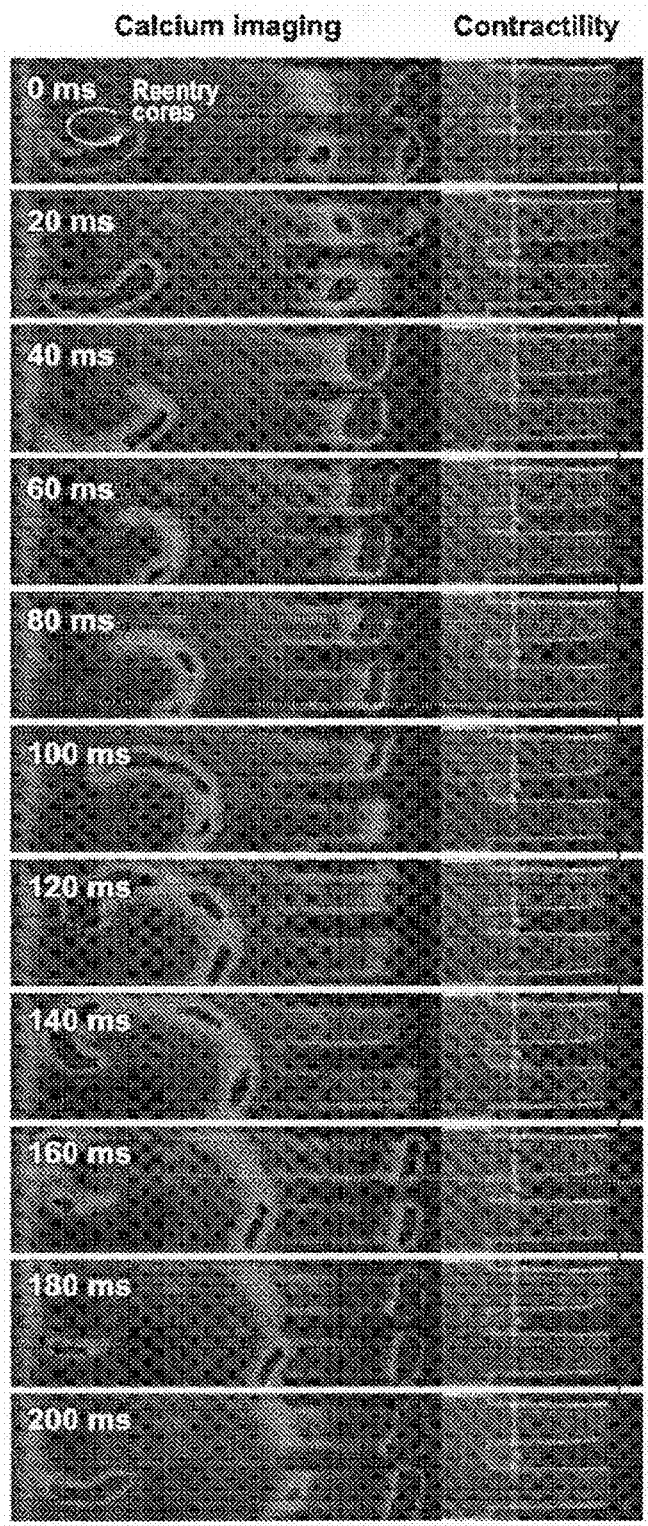
FIG. 48 illustrates an example of a human disease arrhythmia model in accordance with embodiments of the present disclosure.

FIG. 48 shows an example of a human disease arrhythmia model. Pro-arrhythmic events result in a spiral wave formation (e.g., a single rotating wave) and maintenance in CPVT hiPSC-derived cardiac tissues, which is an inherited cardiac disease caused by mutations to calcium handling proteins that, in the presence of b-adrenergic stimulations, result in arrhythmic events, ventricular tachycardia, ventricular fibrillation and ultimately sudden cardiac death in pediatric patients. Patent specific hiPSC-derived cardiomyocytes were genetically engineered to express light sensitive ion channels, and a platform was used to simultaneously measure the calcium handling and contractile properties in the engineered human myocardium while a spiral wave formation was activated.

Figure 51:
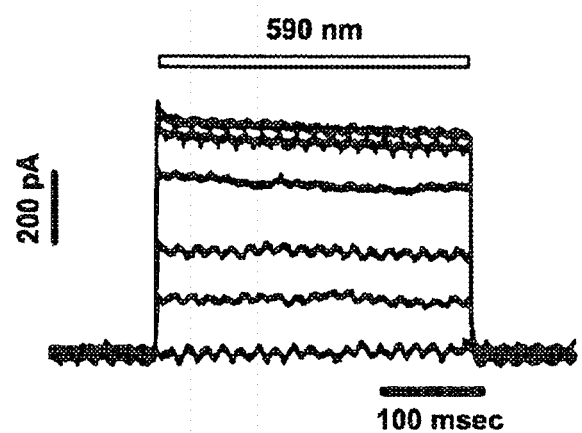
FIG. 51 illustrates hyperpolarization of a tissue structure through a NpHR-mediated outward current in accordance with embodiments of the present disclosure.
Figure 52:
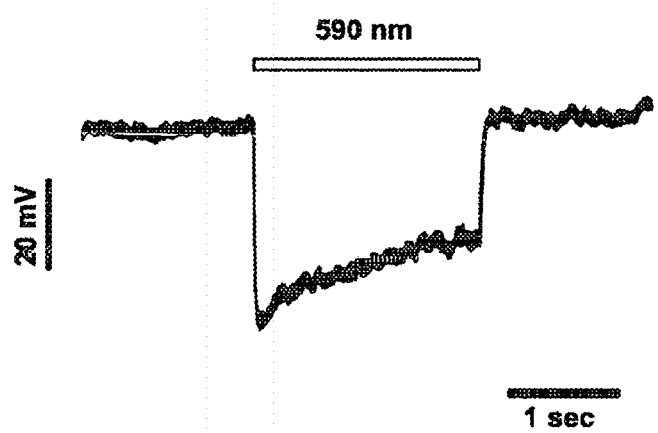
FIG. 52 illustrates hyperpolarization of a tissue structure through a NpHR-mediated outward current in accordance with embodiments of the present disclosure.

As noted above, light sensitive ion channels were transfected to the tissue structure (e.g., cardiomyocytes) for actuating contraction of the tissue structure. Light can activate light-sensitive ion channels, such as ChR2 (cation activator channel) and NpHR (anion inhibitor channel). The viral transduction protocol was integrated with a cell patterning technique to engineer ChR2 (YFP)-expressed anisotropic cardiac tissue. Lentiviral plasmids including cardiac tissue specific promoters increased the transduction efficiency (e.g., approximately 88%). Thus, light sensitive ion channels were functionally integrated into the cell membrane. As shown in FIGS. 39 and 49, a 488 nm LED light elicited action potentials and cell contraction through a ChR2-mediated inward current. As shown in FIGS. 50-52, a 590 nm LED light induced membrane hyperpolarization is shown through a NpHR-mediated outward current, thus preventing electrical activation. The light sensitive ion channels provide control over mechanical contraction.

Figure 53:
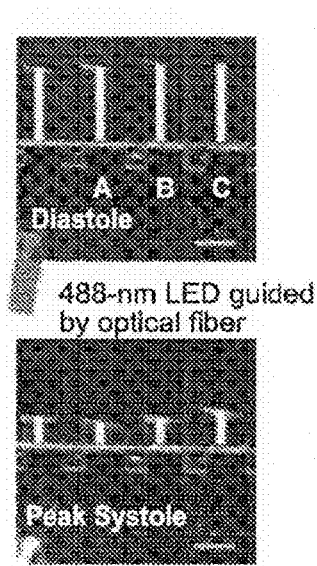
FIG. 53 illustrates diastole and peak systole of a tissue structure for 488 nm LED light stimulation in accordance with embodiments of the present disclosure.
Figure 54:
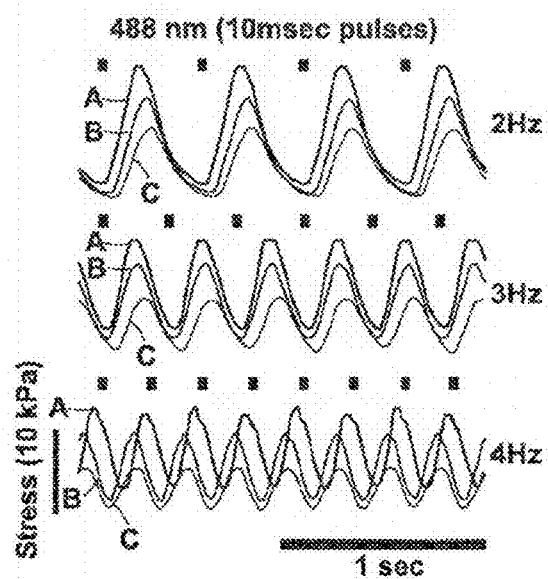
FIG. 54 illustrates contractile stress of a tissue structure for 488 nm LED light stimulation in accordance with embodiments of the present disclosure.
Figure 55:
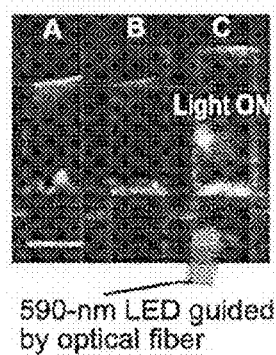
FIG. 55 illustrates a tissue structure for 590 nm LED light stimulation in accordance with embodiments of the present disclosure.
Figure 56:
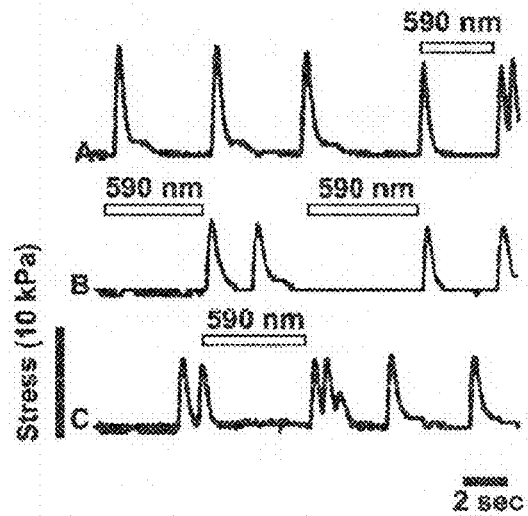
FIG. 56 illustrates contractile stress of a tissue structure for 590 nm LED light stimulation in accordance with embodiments of the present disclosure.

FIGS. 53 and 54 show 488 nm blue light stimulation, and FIGS. 55 and 56 show 590 nm yellow light stimulation. Blue light stimulation (e.g., 12 mW) elicited contractile stress of ChR2 expressing cardiac tissue at pacing frequencies of 2, 3 and 4 Hz. Yellow light (e.g., 11 mW) prevented spontaneous contraction of NpHR expressing cardiac tissue.

Figure 64:
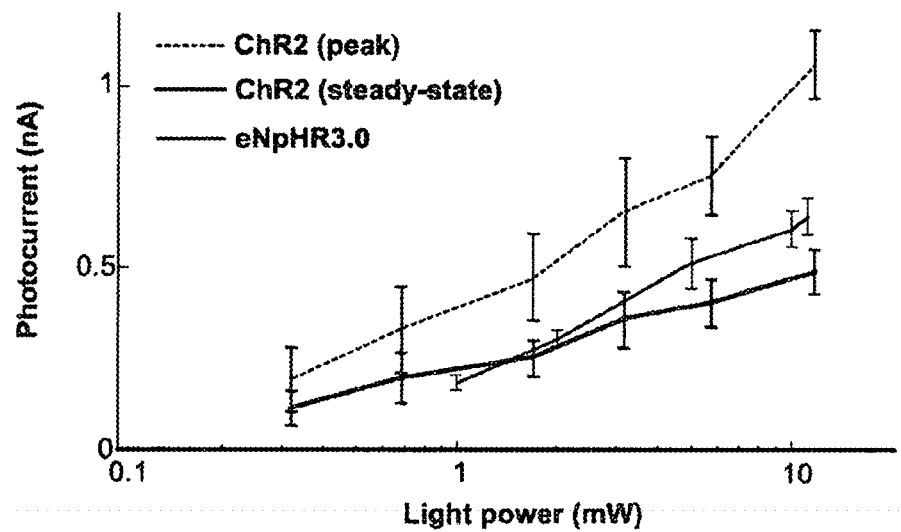
FIG. 64 illustrates data of a ChR2 and NpHR3.0 transfected rat cardiomyocyte transducted with a lentivirus in accordance with embodiments of the present disclosure.

FIG. 64 shows experimental patch-clamp data of a ChR2 and NpHR3.0 transfected rat cardiomyocytes that was transducted with a lentivirus. FIG. 64 shows the light power used for various photocurrent levels. In particular, FIG. 64 further shows that the photosensitive ion channel currents for ChR2 and NpHR expressing cardiac tissue increase with an increase in light power. Approximately 2 mW (or higher) light power was generally used for ChR2 expressing tissue, because 2 mW of light power generated an approximately 0.5 nA current, which is enough to generate action potential of cardiac tissue. Approximately 10 mW (or higher) light power was generally used for NpHR expressing tissue, because 10 mW of light power generated a strong 0.5 nA current, which is enough to hyperpolarize tissue.

Figure 65:
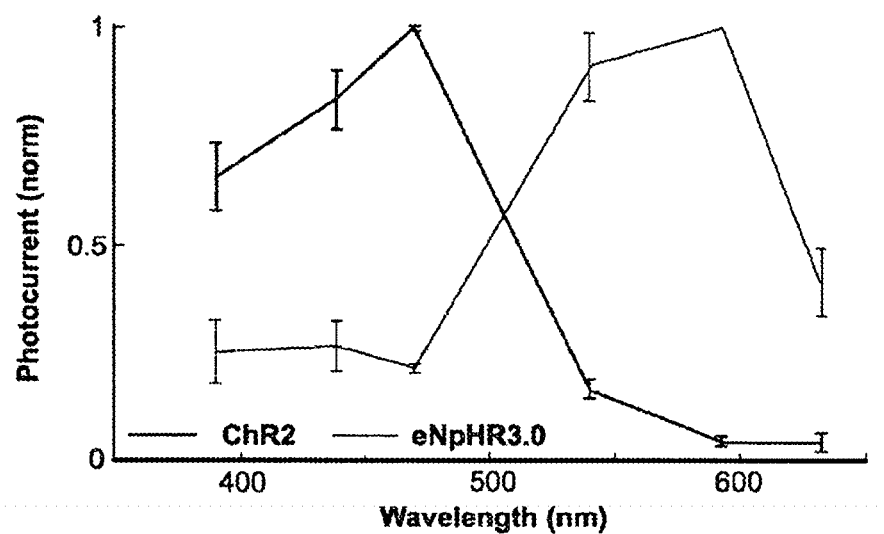
FIG. 65 illustrates wavelengths for ChR2 and NpHR3.0 stimulation in accordance with embodiments of the present disclosure.

FIG. 65 shows the wavelengths used for stimulating the ChR2 and NpHR3.0. In particular, FIG. 65 shows that ChR2 is sensitive to the wavelength of approximately 400 nm to approximately 590 nm, and a wavelength of approximately 470 nm induces a peak photocurrent. Therefore, a wavelength of approximately 470 nm was implemented to stimulate the ChR2 during experimentation. FIG. 65 further shows that NpHR is sensitive to the wavelength of approximately 460 nm to approximately 650 nm, and a wavelength of approximately 590 nm generated a peak current. Therefore, a wavelength of approximately 590 nm was used for stimulating NpHR expressing cardiac tissue.

Figure 66:
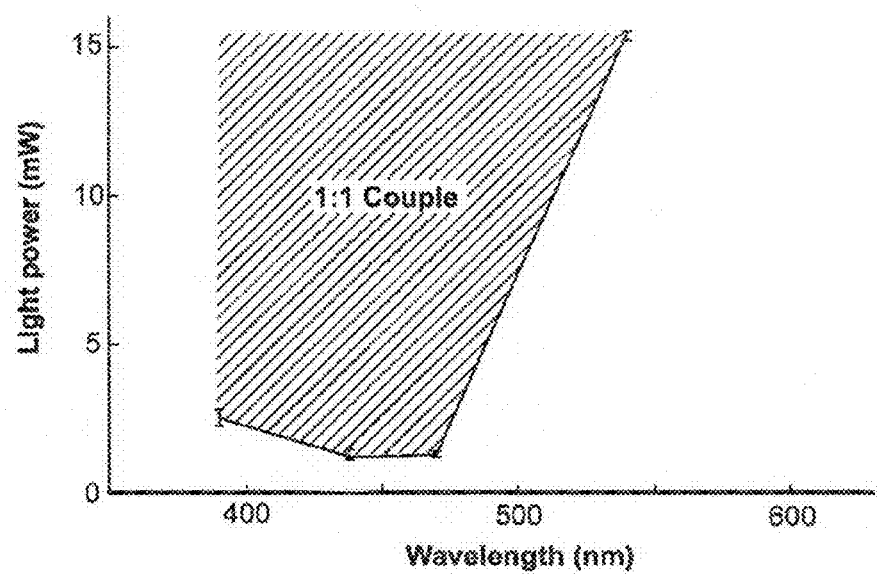
FIG. 66 illustrates a minimum light power for generating a 1:1 couple response of a tissue structure in accordance with embodiments of the present disclosure.

FIG. 66 shows a minimum light power used to generate a 1:1 couple response of tissue structures (e.g., muscle thin films, or the like) with various wavelengths. A 1:1 couple response generally indicates that the tissue structure can respond to all optical pulses (e.g., 1.5 Hz pulses). If the tissue structure is stimulated with a weaker intensity than a minimum light power, the tissue structure cannot respond to all optical pulses, thereby only responding to a limited number of pulses (e.g., one out of two pulses, three out of four pulses, one out of five pulses, or the like. At an approximately 470 nm stimulation, the minimum light power is approximately 1 mW. Therefore, during testing, approximately 2 mW or higher of light power was used to stimulate the tissue structure to ensure that the tissue structure responded to all optical pulses.

Figure 71:
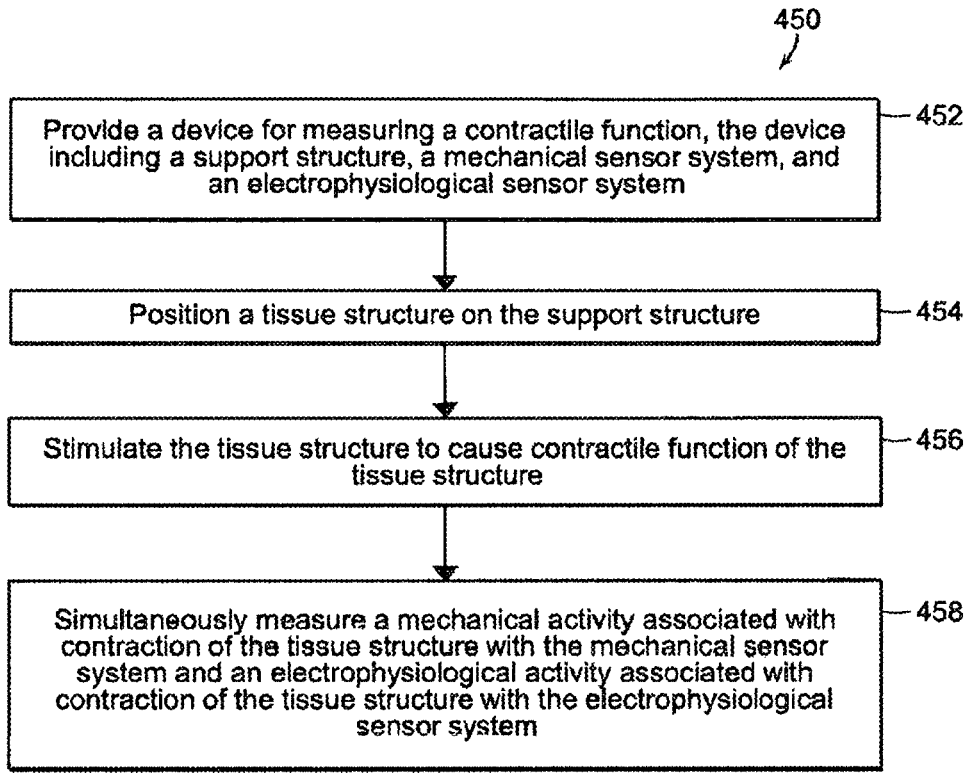
FIG. 71 illustrates an exemplary method of implementing a contractile imaging measurement system in accordance with embodiments of the present disclosure.

FIG. 71 shows an exemplary method 450 of implementing one of the systems discussed herein. At step 452, a device for measuring a contractile function is provided. The device can include a support structure, a mechanical sensor system, and an electrophysiological sensor system. At step 454, a tissue structure can be positioned on the support structure. At step 456, the tissue structure can be stimulated to cause contractile function of the tissue structure. At step 458, a mechanical activity and an electrophysiological activity associated with contraction of the tissue structure can be simultaneously measured by the mechanical and electrophysiological sensor systems, respectively.

Figure 72:
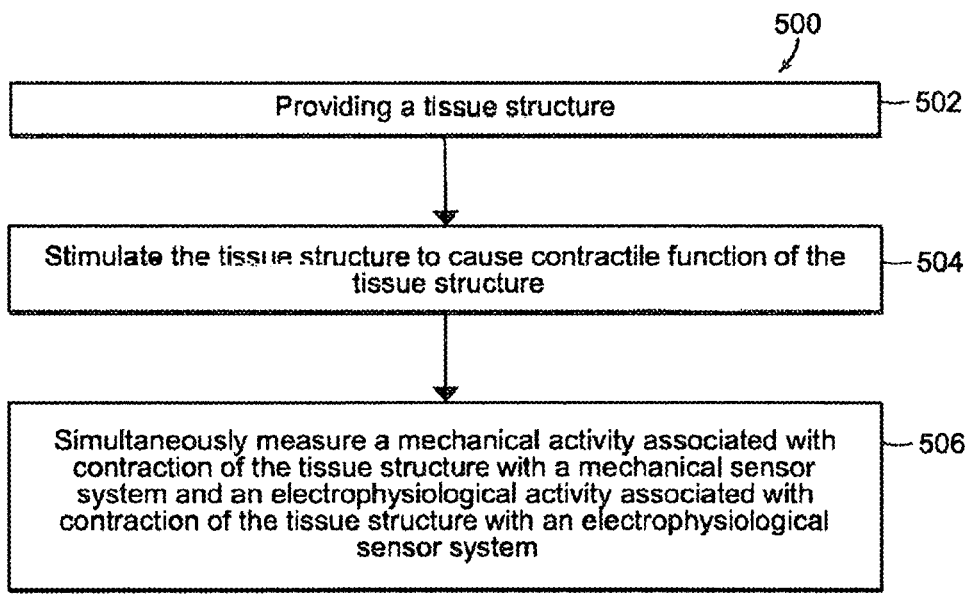
FIG. 72 illustrates an exemplary method of implementing a contractile imaging measurement system in accordance with embodiments of the present disclosure.

FIG. 72 shows an exemplary method 500 of implementing one of the systems discussed herein. At step 502, a tissue structure can be provided. At step 504, the tissue structure can be stimulated to cause contractile function of the tissue structure. At step 506, a mechanical activity and an electrophysiological activity associated with contraction of the tissue structure can be simultaneously measured by the mechanical and electrophysiological sensor systems, respectively.

The exemplary systems and methods discussed herein allow for simultaneous measurement of mechanical and electrophysiological properties of contractile function related to tissues, resulting in more efficient and accurate testing of tissue structures. The systems provide an in vitro, tissue-level cardiotoxicity assay with higher throughput and higher content. The experimentation results demonstrate that optogenetic modification enables optically-controllable cardiac tissue that remains otherwise identical to native tissue. The experimental results also demonstrate that the high spatial resolution of optical stimulation enables measurement of frequency and dose-dependent mechanical and electrophysiological effects on a single platform or chip. The experimental results also demonstrate that reproducible, reentrant cardiac arrhythmias can be initiated using high spatiotemporal resolution optical stimulation. Integration of disease specific hiPSC-CMs into the optogenetic systems may further be used to provide a personalized cardiotoxicity assay to measure different susceptibilities of individuals to candidate drugs.

Equivalents

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by 1/20, 1/10, 1/5, 1/3, 1/2, etc., or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

INCORPORATION BY REFERENCE

The contents of all references, including patents and patent applications, cited throughout this application are hereby incorporated herein by reference in their entirety. The appropriate components and methods of those references may be selected for the invention and embodiments thereof. Still further, the components and methods identified in the Background section are integral to this disclosure and can be used in conjunction with or substituted for components and methods described elsewhere in the disclosure within the scope of the invention.

We claim:

1. A method of measuring a contractile function, comprising:
   providing a device comprising (i) a support structure, (ii) a mechanical sensor system, and (iii) an electrophysiological sensor system;
   positioning a tissue structure on the support structure, said tissue structure comprising one or more intracellular electrodes and/or extracellular electrodes;
   electrically stimulating the tissue structure to cause contractile function of the tissue structure; and
   simultaneously measuring a mechanical activity associated with contraction of the tissue structure with the mechanical sensor system and an electrophysiological activity associated with contraction of the tissue structure with the electrophysiological sensor system.

2. The method of claim 1, wherein the tissue structure comprises at least one of a flexible polymer layer or a hydrogel layer, and a population of isolated muscle cells expressing a photosensitive membrane transport mechanism seeded on at least one of the flexible polymer layer or the hydrogel layer in a predetermined pattern.

3. The method of claim 1, further comprising stimulating the tissue structure with a light source providing photostimulation to the tissue structure, the photostimulation resulting in a contractile function of the tissue structure.

4. The method of claim 3, wherein the photostimulation is provided to the tissue structure at specific wavelengths of light and specific optical pacing frequencies to control contraction of the tissue structure to mimic normal tissue or diseased tissue.

5. The method of claim 3, wherein stimulating the tissue structure with the light source providing the photostimulation to the tissue structure comprises providing the photostimulation to the tissue structure in a predetermined spatiotemporal pattern of light with the light source.

6. The method of claim 5, wherein providing the photostimulation to the tissue structure in the predetermined spatiotemporal pattern of light with the light source comprises:
   illuminating a first portion of the tissue structure with a first set of optical pulses at a substantially constant frequency; and
   illuminating a second portion of the tissue structure with an additional optical pulse for cross-field stimulation, a temporal interval between a pulse in the first set of optical pulses and the additional optical pulse resulting in a spiral wave pattern of contraction.

7. The method of claim 5, wherein providing the photostimulation to the tissue structure in the predetermined spatiotemporal pattern of light with the light source comprises:
   illuminating a first portion of the tissue structure along a line with a first set of optical pulses at a substantially constant frequency;
   illuminating a second portion of the tissue structure with a first additional optical pulse for cross-field stimulation with a first temporal interval between a pulse in the first set of optical pulses and the first additional optical pulse; and
   illuminating the second portion of the tissue structure with a second additional optical pulse for cross-field stimulation with a second temporal interval between a pulse in the first set of optical pulses and the first additional optical pulse.

8. The method of claim 7, further comprising determining a temporal interval vulnerability window based on whether each additional optical pulse resulted in a spiral wave pattern of contraction.

9. The method of claim 8, wherein providing the photostimulation to the tissue structure in the predetermined spatiotemporal pattern of light with the light source comprises:
   illuminating a first portion of the tissue structure along a line with sets of optical pulses at a substantially constant frequency; and
   illuminating a second portion of the tissue structure with additional optical pulses for cross-field stimulation, a temporal interval between a pulse in the sets of optical pulses and the subsequent additional optical pulse varying for each subsequent additional optical pulse.

10. The method of claim 1, wherein simultaneously measuring the electrophysiological activity associated with contraction of the tissue structure with the electrophysiological sensor system comprises optically measuring an intensity or spectrum of (i) a synthetic indicator or (ii) a genetically encoded fluorescent protein indicator due to change in membrane voltage and in ion concentration of tissue in the tissue structure with the electrophysiological sensor system.

* * * * *